US011596803B2

(12) United States Patent
Rogachefsky et al.

(10) Patent No.: US 11,596,803 B2
(45) Date of Patent: Mar. 7, 2023

(54) ORTHOPEDIC TREATMENT DEVICE WITH ELECTROMAGNETIC FIELD GENERATOR

(71) Applicant: Richard Rogachefsky, San Pedro, CA (US)

(72) Inventors: Richard A. Rogachefsky, San Pedro, CA (US); James Seal, Boca Raton, FL (US); Larry Blenke, St. Pete Beach, FL (US); Charles Mondello, Irmo, SC (US)

(73) Assignee: Richard A. Rogachefsky, San Pedro (CA)

( * ) Notice: Subject to any disclaimer, the term of this patent is extended or adjusted under 35 U.S.C. 154(b) by 570 days.

(21) Appl. No.: 16/529,459

(22) Filed: Aug. 1, 2019

(65) Prior Publication Data

US 2020/0038676 A1 Feb. 6, 2020

Related U.S. Application Data

(60) Provisional application No. 62/713,693, filed on Aug. 2, 2018.

(51) Int. Cl.
*A61N 2/02* (2006.01)
*A61N 1/40* (2006.01)
(Continued)

(52) U.S. Cl.
CPC .............. *A61N 2/02* (2013.01); *A61N 1/326* (2013.01); *A61N 1/40* (2013.01); *A61L 2430/02* (2013.01); *A61N 2/008* (2013.01)

(58) Field of Classification Search
CPC . A61N 2/02; A61N 1/326; A61N 1/40; A61N 2/008; A61L 2430/02
(Continued)

(56) References Cited

U.S. PATENT DOCUMENTS 3,745,995 A 7/1973 Kraus
3,820,534 A 6/1974 Kraus
(Continued)

FOREIGN PATENT DOCUMENTS

EP 0 501 048 A1 2/1991
GB 1466337 A 3/1977
(Continued)

OTHER PUBLICATIONS

PCT International Search Report, dated Apr. 5, 2013 (4 pages).
(Continued)

*Primary Examiner* — Sunita Reddy
(74) *Attorney, Agent, or Firm* — Knobbe, Martens, Olson & Bear, LLP

(57) ABSTRACT

Certain aspects relate to systems and techniques for an orthopedic treatment system. In one aspect, the system includes a body unit configured to attach to an orthopedic bone plate, an electromagnetic field emitter positioned within the body unit, the electromagnetic field emitter configured to project an electromagnetic field at a therapeutic frequency for a therapeutic duration. The system may further include an internal power source positioned within the body unit, the internal power source configured to provide electrical current to the electromagnetic field emitter. The system may also include a receiving coil positioned within the body unit, the receiving coil configured to receive power from an external power source, the external power source positioned outside the body unit.

14 Claims, 55 Drawing Sheets

(51) Int. Cl.
*A61N 1/32* (2006.01)
*A61N 2/00* (2006.01)

(58) Field of Classification Search
USPC .................................................. 600/9–15
See application file for complete search history.

(56) References Cited

U.S. PATENT DOCUMENTS

| | | | |
|---|---|---|---|
| 5,411,503 | A | 5/1995 | Hollstien |
| 6,778,861 | B1 | 8/2004 | Liebrecht et al. |
| 10,004,916 | B2 | 6/2018 | Rogachefsky et al. |
| 2002/0032484 | A1* | 3/2002 | Hyde, Jr. ............... A61N 2/06 623/18.12 |
| 2004/0138663 | A1 | 7/2004 | Kosashvili et al. |
| 2005/0070916 | A1 | 3/2005 | Hollstien et al. |
| 2005/0075562 | A1 | 4/2005 | Szakelyhidi, Jr. et al. |
| 2006/0079897 | A1 | 4/2006 | Harrison et al. |
| 2007/0265628 | A1 | 11/2007 | Kraus et al. |
| 2008/0255556 | A1 | 10/2008 | Berger |
| 2009/0062886 | A1* | 3/2009 | O'Handley ............ G01R 33/18 607/51 |
| 2009/0099404 | A1 | 4/2009 | Kraus et al. |
| 2010/0131024 | A1 | 5/2010 | Lathrop et al. |
| 2010/0145337 | A1 | 6/2010 | Janna et al. |
| 2014/0343350 | A1* | 11/2014 | Martinson .......... A61N 1/37235 604/20 |
| 2015/0080636 | A1* | 3/2015 | Rogachefsky ......... A61B 17/72 600/13 |
| 2018/0110550 | A1* | 4/2018 | Pengo ................... A61N 2/002 |
| 2019/0290925 | A1* | 9/2019 | Gellman ............... A61N 2/004 |

FOREIGN PATENT DOCUMENTS

| | | |
|---|---|---|
| JP | 2007-283110 A | 11/2007 |
| JP | 2011-507643 A | 3/2011 |
| WO | WO 95/00085 A1 | 1/1995 |
| WO | WO 2011/051947 A1 | 5/2011 |

OTHER PUBLICATIONS

PCT Notification of Transmittal of the International Search Report and the Written Opinion of the International Searching Authority, or the Declaration, dated Apr. 5, 2013 (2 pages).

PCT Written Opinion of the International Searching Authority, dated Apr. 5, 2013 (6 pages).

Amar et al., "Power Approaches for Implantable Medical Devices". Sensors 2015, 15, published Nov. 13, 2015, pp. 28889-28914.

Shih et al., "Acoustic Polarization for Optimized Implantable Power Transimittion". Department of Mechanical Engineering, National Taiwan University, Taipei, Taiwan. Institute of Applied Mechanics, National Taiwan University, Taipei, Taiwan. MEMS 2007, Kobe, Japan, Jan. 21-25, 2007, pp. 879-882.

Basaeri, et al. "A review of acoustic power transfer for bio-medical implants". Department of Mechanical Engineering, University of Utah, Salt Lake City, UT, USA. Smart Mater, Struct. 25 (2016) 123001, pp. 1-23.

\* cited by examiner

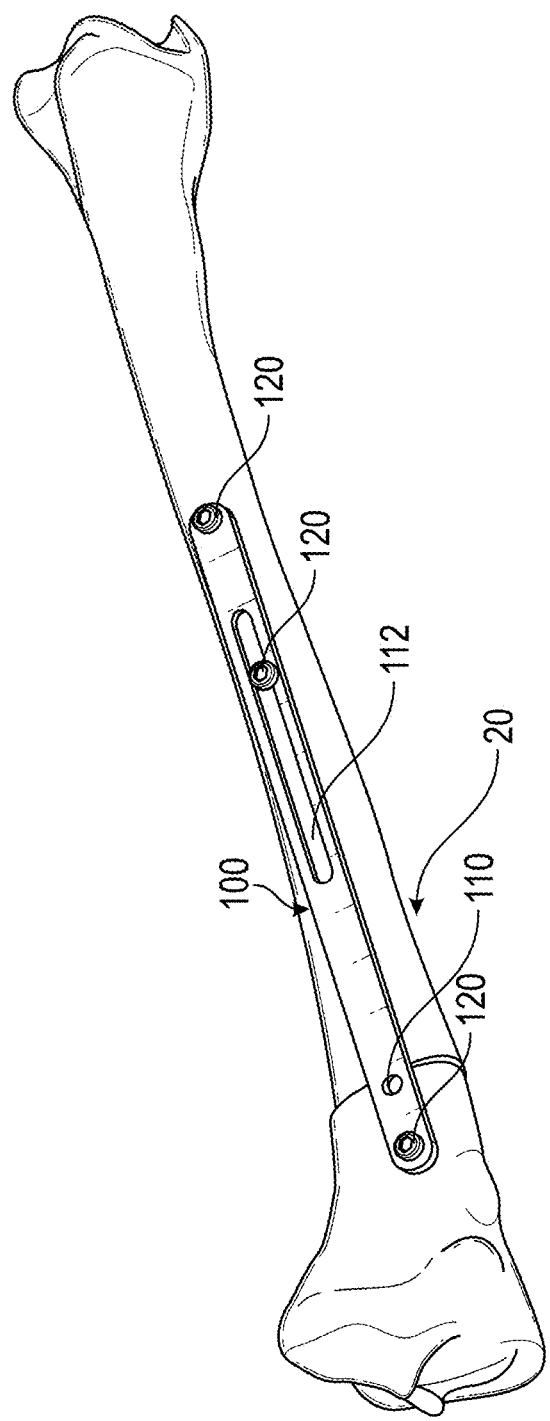

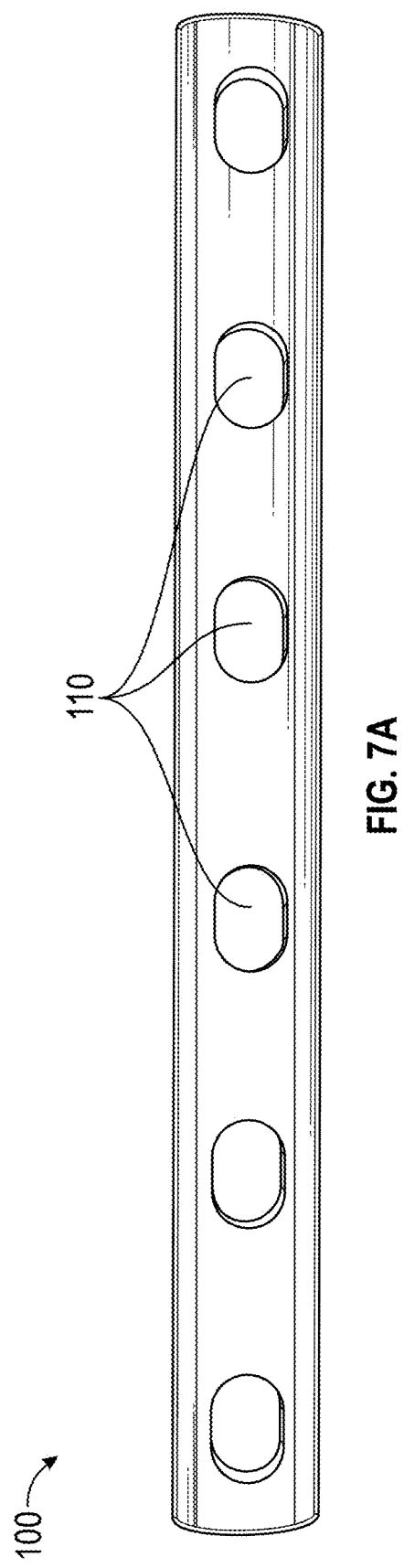

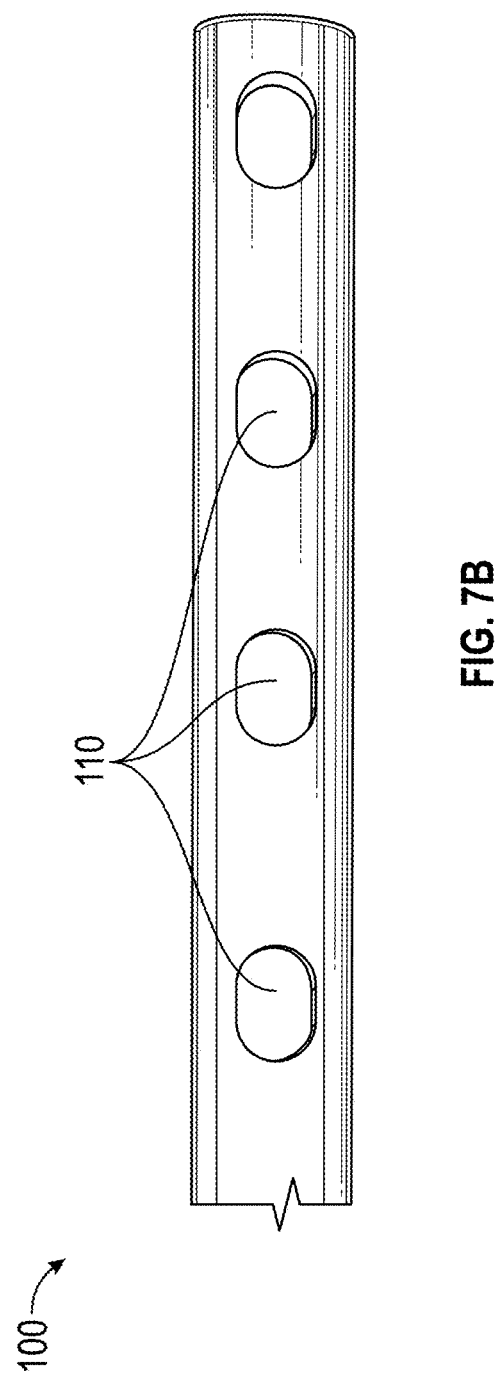

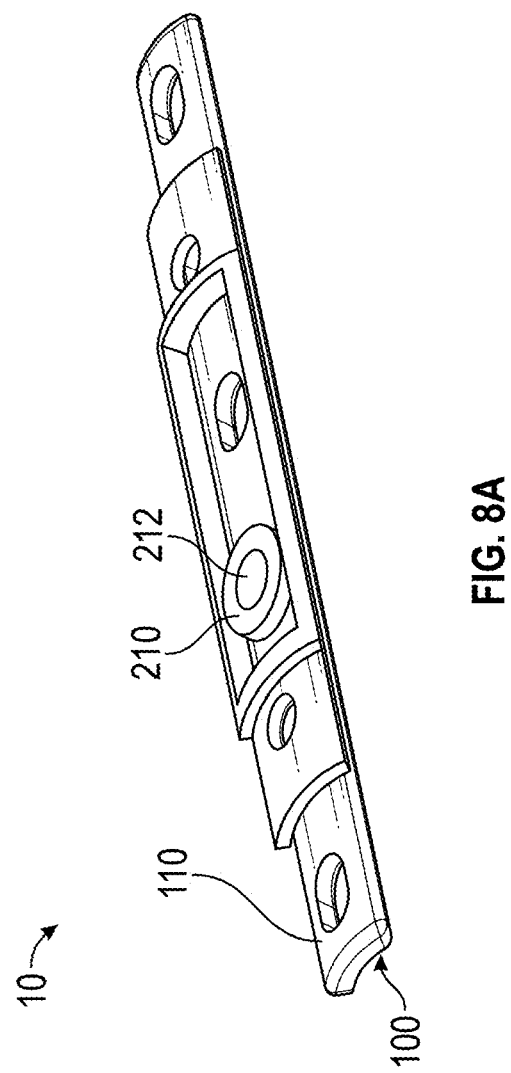

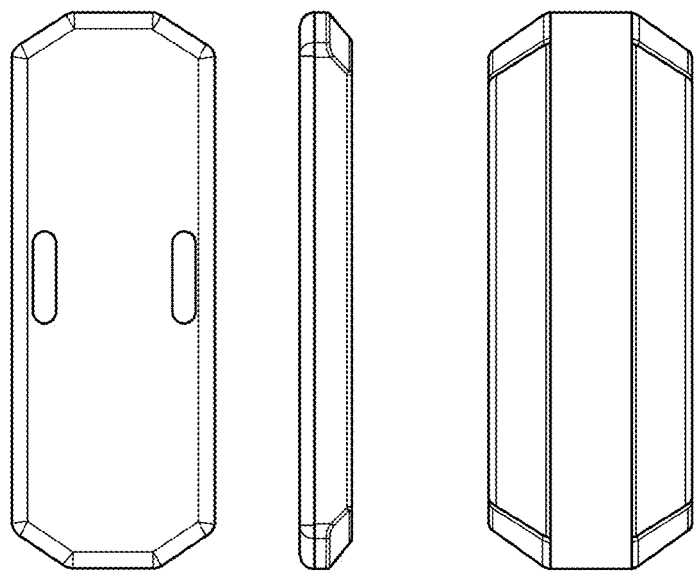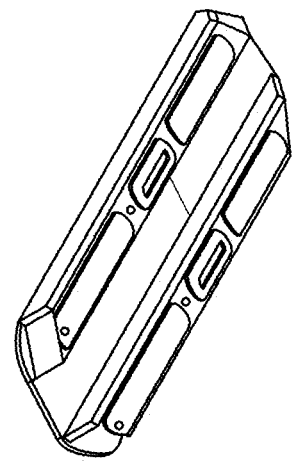
FIG. 9D

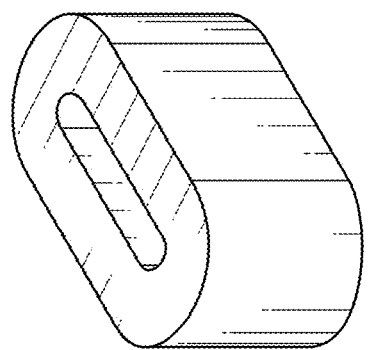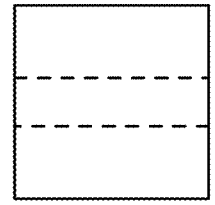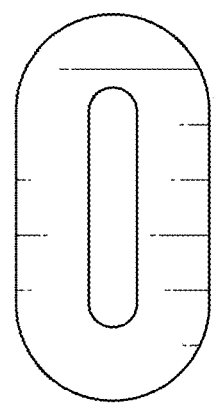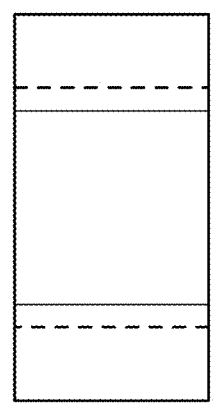
FIG. 9E

ORTHOPEDIC TREATMENT DEVICE WITH ELECTROMAGNETIC FIELD GENERATOR

INCORPORATION BY REFERENCE TO ANY PRIORITY APPLICATIONS

This application claims the benefit of U.S. Provisional Application No. 62/713,693, filed Aug. 2, 2018, which is hereby incorporated by reference in its entirety. Any and all applications for which a foreign or domestic priority claim is identified in the Application Data Sheet filed with the present application are hereby incorporated by reference under 37 CFR 1.57.

BACKGROUND

Fractures occur frequently within the general population from a number of mechanisms including high energy mechanisms such as falls from heights, motor vehicle accidents, and penetrating trauma, in addition to lower energy mechanisms such as ground level falls. Fractures may also result from patient factors such as osteoporosis, being within an elderly age group, or metabolic bone disease. As technology has advanced, the treatment of bone fractures has evolved and improved over the last two decades. Presently, acute long bone fractures that are unstable and are misaligned are treated with open reduction and internal fixation. This treatment methodology has the advantage of correcting the alignment and stabilizing the fractures with a plate and screws applied on the external surface of the bone. This construct allows for more rapid healing and correction of alignment to anatomic so that patients can reach a faster functional recovery.

Unfortunately for the patient, approximately 8% of fractures that undergo open reduction and internal fixation do not fully heal and eventually become non-unions. A non-union can occur when a fracture does not heal properly. Even significantly higher rates of fractures that have internal fixation heal slowly and become delayed unions. There are multiple potential causes for non-unions and delayed unions including biological factors such as: severe fractures in which the blood supply is disrupted, patients with co-morbidities that delay healing such as diabetes, excessive movement by the patient, advanced age, poor nutrition, infection, fracture location (for example, the tibia heals more slowly), and technical factors such as poor fixation.

Electromagnetic fields have been proposed for use for therapeutic purposes for many years. Heretofore, fields have been generated externally and oriented so as to pass through the tissue or bone to be treated. The systems, while effective, have the disadvantage that they require bulky signal generating apparatus and electromagnetic field generating coils to be worn by the patient. This is a particular problem for patients who are ambulatory and a lesser but still significant problem for patients confined to bed. Another disadvantage is potential loss of electromagnetic field strength.

When complications of delayed union and non-union occur, patient function is compromised, and potentially multiple surgeries are needed to obtain healing over a prolonged treatment course. Occasionally fracture healing cannot be accomplished, and amputation is necessary. During the standard recovery after an acute fracture and open reduction and internal fixation, the patient sustains significant time off work, lost wages, and loss of activity and function until healing. The increasing incidence of fractures and the increasing need for fracture care has placed a great strain on the national health care system. There is a need for a method or device that can significantly accelerate the fracture healing time, and significantly lower the rate of non-unions and delayed unions that greatly improve patient recover and function, decreases morbidity, and makes a great impact and advancement of the field of orthopedic surgery.

Presently, external bone stimulators are used to heal fracture delayed unions and non-unions. They have had significant success historically, but are not widely accepted due to inconsistent results. They have the disadvantage of being cumbersome and must be worn for extended periods of time resulting in compliance issues.

There is a need for orthopedic treatment devices that are useful for assisting in fracture and wound healing, treating infection, reducing pain, and for other therapeutic purposes. There is also a need for orthopedic treatment device that can incorporate a bone stimulator to emit electromagnetic fields. There is a need for an embedded bone stimulator that is not cumbersome for ease of installation, use, and to improve compliance. There is also a need for an embedded bone stimulator that can be positioned closely to the fracture to promote healing.

SUMMARY OF THE INVENTION

The present disclosure remedies the foregoing shortcomings of the prior art by providing an improved medical device for implanting in a patient.

In embodiments, a method for treating an injury may comprise: positioning an orthopedic treatment device on a bone fracture in a mammal, the orthopedic treatment device comprising an electromagnetic field emitter; and activating the electromagnetic field emitter to deliver an electromagnetic field proximate the bone fracture, the electromagnetic field delivered according to a treatment regimen. In some embodiments, the treatment regimen may include one or more predetermined electromagnetic frequencies and durations. The method may include powering the electromagnetic field emitter from a power supply positioned external to the mammal.

In embodiments, an orthopedic treatment system may comprise: a body unit configured to attach to an orthopedic bone plate; an electromagnetic field emitter positioned within the body unit, the electromagnetic field emitter configured to project an electromagnetic field at a therapeutic frequency for a therapeutic duration; an internal power source positioned within the body unit, the internal power source configured to provide electrical current to the electromagnetic field emitter; and a receiving coil positioned within the body unit, the receiving coil configured to receive power from an external power source, the external power source positioned outside the body unit.

In some embodiments of the orthopedic treatment system, the external power source may comprise a delivery coil, the delivery coil configured to inductively charge the receiving coil. The receiving coil may be configured to provide electrical current to the internal power source. A microprocessor may be contained within the body unit, the microprocessor in electrical communication with the electromagnetic field emitter, the internal power source, and the receiving coil. The microprocessor may be configured to modify an electrical current delivered from the receiving coil to the internal power source such that the electrical current is in a usable form for the internal power source. In some embodiments, the electromagnetic field emitter may comprise a coil wrapped around a ferrite core. The body unit may be configured to be attached to the orthopedic bone plate by a fastening device. The fastening device may be selected from the group of a clip, a screw, and an adhesive. The electromagnetic field emitter may be configured to project the electromagnetic field at an orthopedic fracture site. In some embodiments, the electromagnetic field emitter may be positioned adjacent the orthopedic bone plate, such that the electromagnetic field is not projected through the orthopedic bone site. The system may further comprise an antenna positioned within the body unit, the antenna configured to communicate with an external remote control receiver. In embodiments, the system may further comprise a sensor positioned within the body unit in communication with the antenna, the sensor configured to measure an internal characteristic within an implant site. The sensor may be configured to measure electromagnetic field strength. The sensor may be configured to measure a stress exerted on the orthopedic bone plate. In some embodiments, the external power source may be positioned on the skin of a mammal, the mammal implanted with the orthopedic bone plate. In certain embodiments, the microprocessor may be configured to direct the electromagnetic field emitter to deliver a therapy regimen. In embodiments, the system may further comprise a second electromagnetic field emitter, the electromagnetic field emitters configured to project opposing electromagnetic fields, the opposing magnetic fields configured to create a Hemholtz effect such that the magnetic field strength at an orthopedic fracture site is increased. In some embodiments, the body unit can be a sleeve. The sensor can be a strain gauge. In certain aspects, the system may further include an external energy source, the external energy source configured to inductively provide energy to the power supply through skin. In some aspects, the system may include a second body unit configured to attach to an orthopedic bone plate. In some embodiments, the electromagnetic field emitter, the power source, and the receiving coil are contained within the orthopedic bone plate.

In some embodiments, an orthopedic treatment system may include a body unit configured to attach to an orthopedic bone plate, the orthopedic bone plate configured to be positioned on a bone fracture of a patient; and a permanent magnet field generator comprising a permanent magnet. The permanent magnet field generator may have a weight differential configured to move the permanent magnet field generator with motion of the patient and generate a magnetic field at a therapeutic frequency for a therapeutic duration. In some embodiments, an orthopedic treatment system may include a body unit configured to attach to an orthopedic bone plate, the orthopedic bone plate configured to be positioned on a bone fracture of a patient; and a permanent magnet field generator comprising a permanent magnet, the permanent magnet configured to move to generate a magnetic field at a therapeutic frequency for a therapeutic duration. The permanent magnet field generator can have a weight differential configured to move the permanent magnet with motion of the patient. The permanent magnet field generator can include an actuator configured to rotate the permanent magnet.

An understanding of these and other aspects, features, and benefits of the invention may be had with reference to the attached figures and following disclosure, in which preferred embodiments of the invention are illustrated and described.

BRIEF DESCRIPTION OF THE DRAWINGS

Throughout the drawings, reference numbers are used to indicate correspondence between referenced elements. The drawings are provided to illustrate embodiments of the features described herein and not to limit the scope thereof.

FIG. 5A illustrates an embodiment of a bone plate configured for implantation on a fractured bone.

FIG. 7A illustrates an embodiment of a bone plate for implantation on a fractured bone.

FIG. 7B illustrates a close up view of the bone plate of FIG. 7A.

FIG. 8A illustrates an embodiment of an orthopedic treatment device configured for implantation on a fractured bone.

FIG. 9D illustrates an embodiment of the body unit of the orthopedic treatment device of FIGS. 9A-9C.

FIG. 9E illustrates an embodiment of the electromagnetic field emitter of the orthopedic treatment device of FIGS. 9A-9C.

DETAILED DESCRIPTION

The devices, methods, and systems disclosed herein relate generally to fixation devices. More specifically, the invention relates to fixation devices that are useful for assisting in fracture and wound healing, treating infection, reducing pain, and for other therapeutic purposes. Preferred embodiments now will be described with reference to the figures.

Figure 1A:
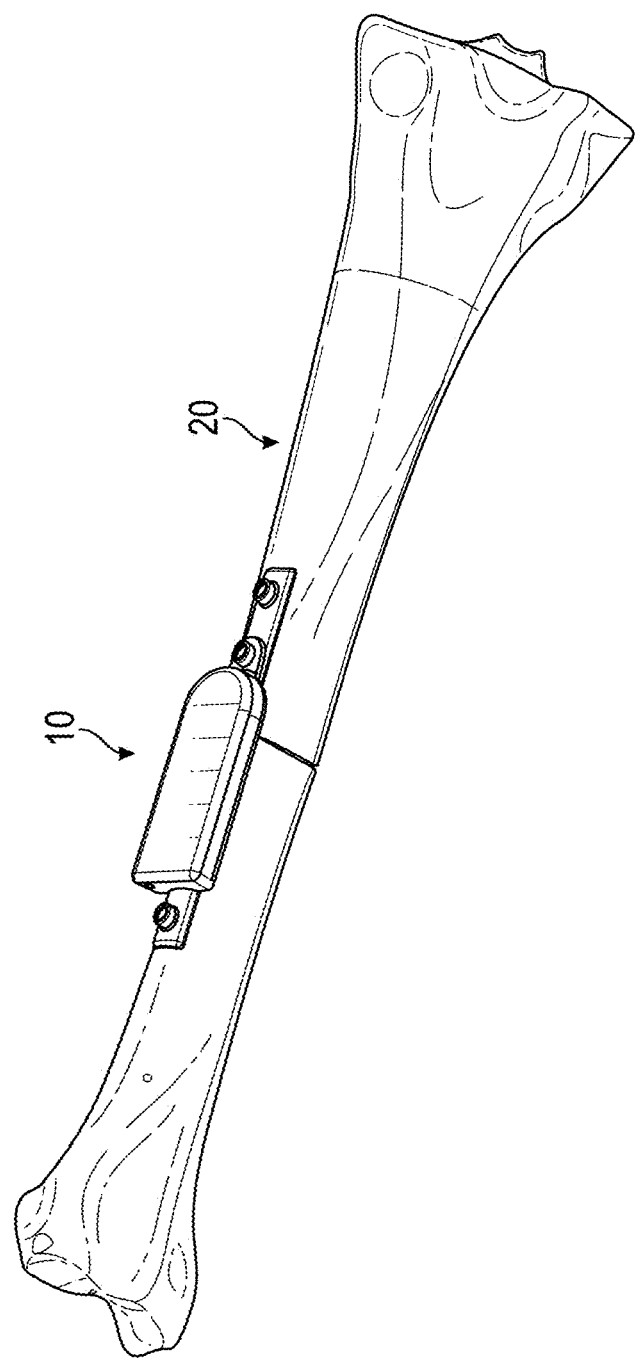
FIG. 1A illustrates an embodiment of an orthopedic treatment device for implantation on a fractured bone.
Figure 1B:
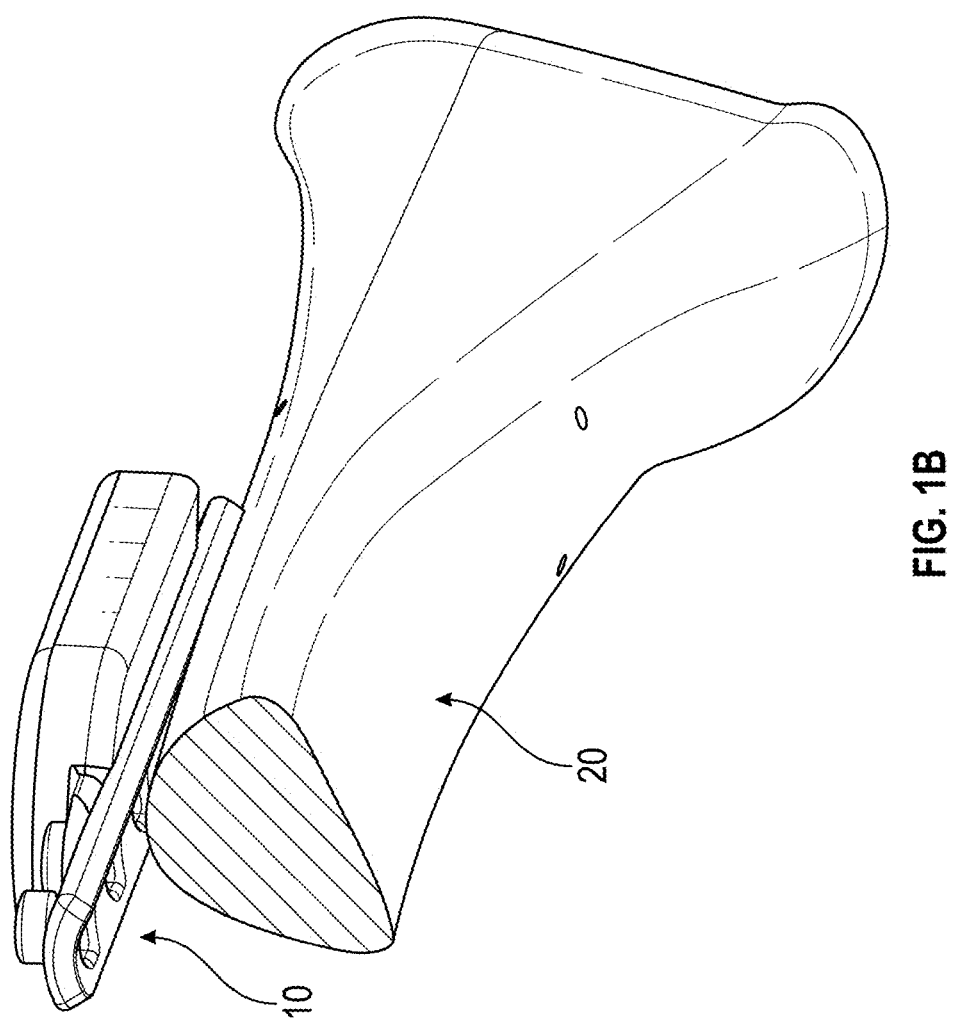
FIG. 1B illustrates a side view of an embodiment of the orthopedic treatment device for implantation on a fractured bone.

FIG. 1A illustrates an embodiment of an orthopedic treatment device 10 designed to be implanted on a fractured bone 20. FIG. 1B illustrates a cross-sectional view of the fractured bone 20 and the orthopedic treatment device 10 of FIG. 1A. The orthopedic treatment device 10 can include a bone plate 100 and a body unit 200.

Figure 2:
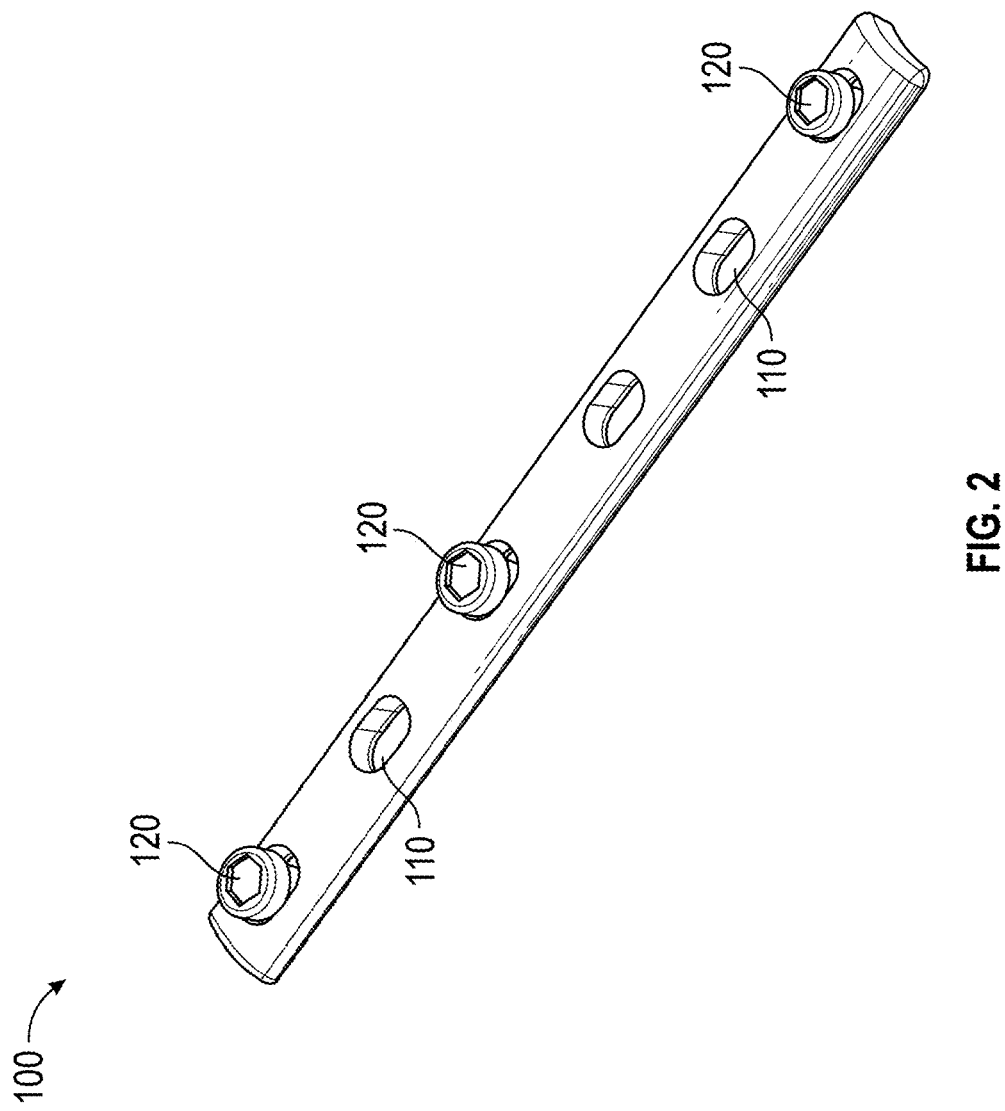
FIG. 2 illustrates an embodiment of a bone plate for implantation on a fractured bone.

As shown in FIG. 2, in embodiments the bone plate 100 can include a thin metal plate. The bone plate 100 can include one or more screw holes 110 along the length of the bone plate 100. As shown in FIGS. 1A-1B, the bone plate 100 can be affixed to a fractured bone 20. Such bone plates 100 are known for placement on a bone 20 to aid, immobilize and properly realign the bone 20 having a fracture. The bone plate 100 can be held in place and affixed to the fractured bone 20 with screws 120 through the screw holes 110 of the bone plate 100. The bone plate 100 can be used to immobilize the fractured bone 20 to properly align the fractured bone 20 and aid in the healing process. The fractured bone 20 is opened in the standard approach. Once the fractured bone 20 is exposed, it is reduced in the correct alignment. The bone plate 100 and multiple screws 120 are applied to stabilize and rigidly maintain the fractured bone 20 in the correct alignment. Once the fractured bone 20 is fixated with the bone plate 100, the body unit 200 is fixated to the bone plate 100 in close approximation to the fracture of the bone 20. Once the body unit 200 is fixated to the bone plate 100, the soft tissues are closed with the body unit 200 maintained internally fixated to the bone plate 100 positioned closely to the fracture of the bone 20.

In some embodiments, the bone plate 100 may be a surgical or orthopedic plate. The bone plate 100 may be any known plate or plate-like structure, for example, such as used to maintain position of a fractured bone 20 for healing that bone 20 or for fusion of bones, as in spinal surgery. The bone plate 100 may be fabricated in a size and shape that give it sufficient strength to stabilize the fracture of the bone 20 during healing. The bone plate 100 may be fabricated from a material that permits an electromagnetic field to pass therethrough. The bone plate 100 may be made of material that is non-ferrous, such that the emitted electromagnetic field will readily pass through the bone plate 100 to the treatment area. The bone plate 100 may be made from a material that will not distort the field generated by the electromagnetic field emitter 210, but the electromagnetic field emitter 210 and the bone plate 100 may be designed to cooperate in creating a field that will effectively intersect with a fracture or wound. In some embodiments, the body unit 200 may be made of titanium or stainless steel.

In certain embodiments, the bone plate 100 can be 4 mm, 5 mm, 10 mm, 11 mm, 13.5 mm, 17.5 mm, or any other appropriate sized bone plate, approximately sized to treat and stabilize the size, position, location, and nature of the fracture of the bone 20.

As shown in FIG. 2, not all screw holes are utilized to fixate the bone plate 100. For example, a screw 120 may not be inserted into the screw hole 110 nearest the fracture on the bone 20 as that can further damage the fractured bone 20. Further, the screw holes 110 can remain unused without screws 120 to allow the body unit 200 to be installed without physical interference of the screw 120. In other embodiments, the screws 120 can be installed flush with the body plate 100 such that the head of the screw 120 is not positioned above the bone plate 100. This can reduce interference with the body unit 200 and allow more screws 120 to be installed to stabilize the bone plate 100. Furthermore, the screw hole 110 can be used to install other components, such as a ferrite core 212, as discussed more below. In certain embodiments, all screw holes may be utilized for a screw or only some of the screw holes may be utilized for a screw.

In addition to the screw holes 110 being used to affix the bone plate 100 to the fractured bone 20, the screw holes 110 can be used to affix the body unit 200 to the bone plate 100. This can be seen in FIGS. 1A-1B. The screws 120 may be locking screws, plate screws, cancellous screws, cortex crews, and any other appropriate screws.

As shown in FIG. 1B, in embodiments the body unit 200 can extend past the bone plate 100 such that the sides of the body unit 200 will extend past the bone plate 100 so that contact between the body unit 200 and the bone 20 can be obtained. The electromagnetic emitter coils 210 within the body unit 200 can be positioned past the bone plate 100 so that the emitted electromagnetic field will not have to transverse the bone plate 100, which would result in deterioration of the electromagnetic field. In embodiments, the body unit 200 may not extend appreciably past the bone 20 to minimize soft tissue impingement. In addition, the body unit 200 extending minimally past the bone plate 100 may also create an open area to allow soft tissue blood flow to the bone 20.

Once the body unit 200 is fixated to the bone plate 100, the soft tissues may be closed with the body unit 200 maintained internally fixated to the bone plate 100 close to the fracture of the bone 20. The orthopedic treatment device 10 can be implanted on the bone 20 such that there is soft tissue under the body unit 200 to allow blood circulation to the fractured bone 20.

In embodiments, the body unit 200 can have a length of approximately 1 inch to approximately 10 inches. The body unit 200 can have a height of approximately 0.1 inches to approximately 1 inch. The body unit 200 can have a width of approximately 0.5 inches to approximately 3 inches. In some embodiments, the length of the body unit 200 can be approximately 3 inches to approximately 3.25 inches. In other embodiments, the body unit 200 can have a longer length based on the size of the bone plate 100 being used and bone fracture 20 being fixated.

Figure 3B:
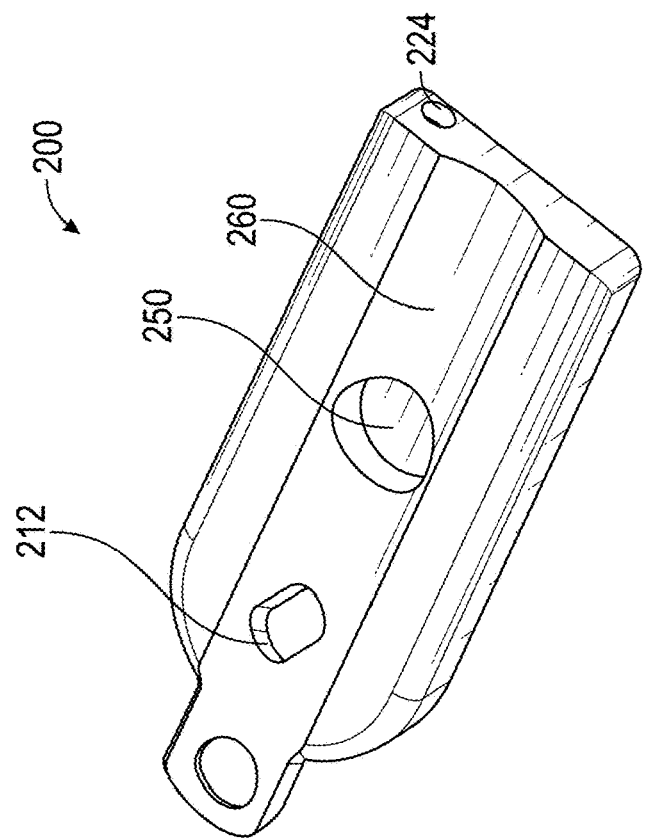
FIG. 3B illustrates the bottom side of an embodiment of the body unit.
Figure 3A:
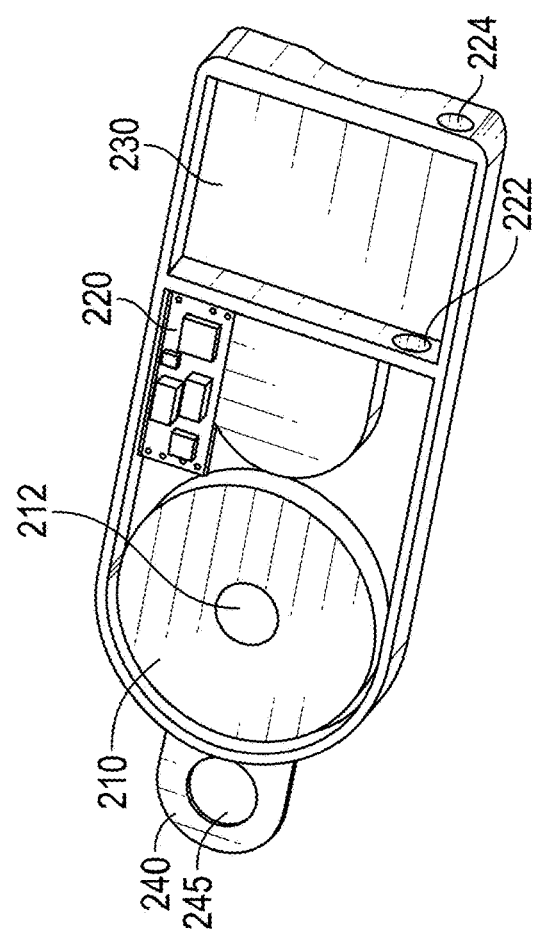
FIG. 3A illustrates the internal components of an embodiment of the body unit.

FIG. 3A illustrates the internal components of the body unit 200. FIG. 3B illustrates the bottom side of the body unit 200. The body unit 200 can be self-contained and implanted into the patient. The body unit 200 can be attached to the body plate 100 that is used for open reduction and internal fixation of a fracture of a bone 20. The internal components of the body unit 200 can include an electromagnetic field emitter 210, a controller 220, and a power source (not shown). The body unit 200 can include a compartment 230 for the power source, such as a battery.

The orthopedic treatment device 10 according to the illustrated embodiments includes an electromagnetic field emitter 210 disposed in the cavity of the body unit 200. The electromagnetic field emitter 210 may take any conventional shape, and preferably includes an electromagnetic field emitter coil 210 such as a solenoid coil through which a current is passed to create an electromagnetic field. Other embodiments may include coils 210 that are wrapped tightly that are raised or flat pancake type coils 210 for more low profile. The electromagnetic field emitter 210 may include an air coil, axial coil, flat or pancake coil, or other types of coils. In one embodiment, each of the electromagnetic field emitters 210 is a wound coil. The electromagnetic field emitter coil 210, also referred to as an air coil 210, may include a wire wound continuously along an axis in multiple layers to form a cylindrical coil 210 defining an open middle. In some embodiments, the air coil 210 may be wrapped a ferrite core 212. In addition, the electromagnetic field emitter coils 210 can have a ferrite core 212 to increase the electromagnetic field strength or have electromagnetic field emitter coils 210 that do not have a ferrite core 212.

The electromagnetic field emitter coils 210 may have a diameter ranging from approximately 0.1 inch to approximately 1 inch. The electromagnetic field emitter coils 210 may have a thickness of approximately 0.01 inches to approximately 0.1 inches.

The electromagnetic field emitter 210 generally is a conventional structure that will emit an electromagnetic field at a frequency of between about 1 and about 100 Hz, between about 5 Hz and about 30 MHz, for example between about 50 Hz to 25 MHz, 100 Hz to 20 MHz, 1 MHz to 15 MHz, or 5 to 10 MHz. In certain embodiments, the magnetic flux density, may range from approximately 10 Gauss to approximately 400 Gauss within a treatment volume, for example between about 20 to 350 Gauss, 30 to 300 Gauss, 60 to 250 Gauss, or from about 100 to 200 Gauss. As a result, the electromagnetic field emitter 210 can be placed in close proximity to a fracture in a bone 20 and/or proximate nearby afflicted muscle or other tissue. In some embodiments, the electromagnetic field emitter 210 can emit an electromagnetic field range from 50 to 100 Gauss with a repetition rate from 10 to 20 Hz. The range of electromagnetic field parameters can be approximately 1 Gauss to approximately 1000 Gauss and approximately 1 Hz to approximately 30 MHz. The desired voltage from the power source can be approximately 1 Volt to approximately 40 Volts.

As discussed above, the body unit 200 can also include a ferrite core 212. The ferrite core 212 can be retained with and/or protrude through the unused screw hole 110 of the bone plate 100. The ferrite core 212 may have a diameter of approximately 0.04 inch to approximately 0.1 inch. The ferrite core 212 may have a thickness of approximately 0.01 inch to approximately 0.1 inch.

The electromagnetic field emitter 210 may include multiple emitter coils 210. The electromagnetic field emitter 210 may be positioned at the fracture of the bone 20 so that the emitted electromagnetic field is at high strength at the fracture of the bone 20 creates a greater biological effect and accelerated fracture healing. Within the body unit 200 is a power source such as a battery, which provides power to the controller 220 and circuitry. The electromagnetic field emitter 210 may be mounted in any position within the body unit 200, to ensure maximum exposure of the fracture of the bone 20 to the generated field. The electromagnetic field emitter 210 may be fixed to the body unit 200 in any number of ways, including fasteners and adhesives. The electromagnetic field emitter 210 may also be retained within the body unit by means of encapsulating the electromagnetic field emitter 210 and other components within the body unit 200. In some embodiments, the electromagnetic field emitter 210 may be aligned with the fracture of the bone 20.

As discussed above, the orthopedic treatment device 10 may include a series of electromagnetic field emitters 210. Using appropriate controls, the electromagnetic field emitter coils 210 may be selectively energized at desired frequencies and for preferred durations. For example, when body unit 200 with multiple electromagnetic field emitters 210 is implanted, the electromagnetic field emitter coil or coils 210 closest to the fracture site 20 will be energized according to a first treatment methodology. Other electromagnetic field emitter coils 210 may be energized differently or not at all.

As described above, orthopedic plates 100 generally have a plurality of holes 110, to allow a surgeon maximum flexibility for affixation of the bone plate 100 to the bone 20. The plurality of holes 110 also are used as screw holes 110 to affix the bone plate 100 to the bone 20. In embodiments, a hole or holes 110 aligning with the fracture of the bone 20 is not used, because a screw 120 is rarely used at the fracture of the bone 20. In certain embodiments, a screw may be utilized at the fracture, depending on the nature of the break.

A controller 220 and/or a power source may be included with the electromagnetic field emitter 210 or may be positioned anywhere on or spaced from the bone plate 100. The controller 220 and circuitry connect the power source to the electromagnetic field emitter coils 210 and modify the power and electrical current for powering the electromagnetic field emitter coils 210. Wires can be used to connect the power source, the controller 220 and the electromagnetic field emitter coils 210.

A controller 220 which may be fabricated on a printed circuit board and/or as an integrated circuit is provided in communication with the electromagnetic coil of the electromagnetic field emitter 210 for generating a signal to energize the electromagnetic field emitter 210. The controller 220 also modifies and changes the treatment regimen thereby changing the characteristics of the applied field emitted from the emitter coils 210.

The control circuitry may be provided to allow for user selection of strength and duration of currents applied to the electromagnetic emitters 210. The controller 220 may be programmable, i.e., via remote control through an input device external to the patient, to allow for custom treatment of each patient. In other embodiments, the controller 220 could be pre-programmed with a treatment methodology and merely turned on to run through that pre-determined treatment regimen. The control circuitry may further include wake-up circuitry or the like, to allow for delayed operation. For example, an orthopedist may determine that they would prefer not to use the electromagnetic field therapy until some amount of time after surgery. Thus, the electromagnetic field emitter 210 should not be energized until that time, if at all.

A microprocessor circuit board will be incorporated in the body unit 200 to control and modify the electrical current and power from the power source to the emitter coils 210. The body unit 200 can include a hole 222 for internal cabling to the power source compartment 230. The body unit 200 can also include a cable port 224 for cabling of the power source for external charging.

Generally speaking, the controller 220 is energized by the power source to generate the signal that when applied to the electromagnetic field emitter 210 creates an electromagnetic field. In some embodiments, the generated electromagnetic field may include a varying electromagnetic field that intersects the wound or fracture 20.

In one example, the controller 220 is programmed with a series of instructions for controlling the electromagnetic field emitted by the electromagnetic field emitter 210. More specifically, the controller 220 may be programmed with a routine such as a series of intensity and/or time dependent instructions. Depending upon the program routine, the controller 220 will manipulate the power from the power source to supply a current to the electromagnetic field emitter 210, which in turn will create an electromagnetic field corresponding to the applied current. By varying the current and the time, any number of routines may be used, as required by the patient. The controller 220 may be preprogrammed with a number of routines for application of varied electromagnetic fields to the injury site. For example, routines may be included that depend upon the location and/or severity of a fracture or accompanying wounds to nearby tissue and/or muscle.

Treatment regimens may be approximately 2 hours for approximately 2 to 3 times per day. In embodiments, treatment sessions may be for about 1, 2, 4, 6, or more hours and may occur for about 1, 2, 3, 4, 5, 6, 7, 8, or more times per day. The number of emitter coils 210 can be more than one to up to multiple coils 210. The coils 210 can be fired to emit the treating magnetic field in series. For example, one of a group of multiple coils 210 are activated then the second coil 210, third coil 210 and then the other coils 210 in series and then back to the activation of the first coil 210 so that different areas of the fracture 20 are stimulated and so that there is not as much power requirement from the power source. The activation of the electromagnetic field emitter coils 210 in series also decreases the chance that the emitted magnetic fields cancel each other. In some embodiments, electromagnetic field emitter coils 210 in pairs may be positioned on opposite sides of the internal orthopedic treatment device 10 and can be activated simultaneously. The pairs of coils 210 can provide opposing magnetic fields to create a Hemholtz effect to increase the magnetic field strength at the fracture 20. This positioning of the electromagnetic field emitter coils 210 also provides greater stimulation of the fracture 20, less power requirements and since the electromagnetic field emitter coils 210 are on opposite sides of the internal orthopedic treatment device 10 less possibility that the fields will cancel each other. The series activation of the electromagnetic field emitter coils 210 allow the unstimulated area of the fracture 20 to rest. This series activation of the coils 10 also allows the fracture 20 to be stimulated in more of a pulsating effect allowing different areas of the fracture 20 to have stress and relaxation. In some embodiments, all electromagnetic field emitter coils 210 can be activated simultaneously to provide a large burst of magnetic field towards the fracture 20 for greater stimulation. This difference in electromagnetic field emitter coil 210 activation and treatment regimen will be controller by the controller 220 and the PC board circuitry.

In some embodiments, the controller 220 may be programmable before implantation into the patient, or after being inserted into the patient. The treatment regimen can be preprogrammed so that the internal orthopedic treatment device 10 runs automatically through a series of treatments pre-determined based on the stage of fracture healing. In another embodiment, the internal orthopedic treatment device 10 can have direct communication with an external remote control to allow the surgeon and other operators to remotely change the treatment regimen if desired.

One lead may be accessible through the port 224 of the body unit 200 and through the skin to allow tethering to a computer or the like useable in programming the controller 220. The controller 220 may include a wireless receiver configured to receive programming instructions wirelessly from a computer or the like equipped with a transmitter. Further, the controller 220 may include a wireless transmitter for transmitting data corresponding to the signal generated by the controller 220.

Although not illustrated in FIG. 3A, a power source, such as a battery, may also be provided within the body unit 200, in communication with the electromagnetic field emitter 210 and the controller 220. In certain embodiments, within each self-contained unit is a power source such as one or multiple batteries that are implantable and re-chargeable for example, lithium ion batteries or batteries of similar construct. Leads or wires may also be provided in the body unit 200 through an internal passageway 222 to interconnect the electromagnetic field emitter 210, the controller 220, and the power source (not shown). The power source may be any known or developed power source sufficient to power the electromagnetic field emitter coils 210. Batteries have been conventionally implanted into the human body, e.g., in pace makers, and such powering technology may be applicable.

In addition to a battery, signal generating electronics and an electromagnetic coil 210, the orthopedic treatment device 10 may further include a receiver and a transmitter, allowing the orthopedic treatment device 10 to communicate with an external device. Such an arrangement would allow for downloading to the implanted orthopedic treatment device 10 signal patterns and schedules, e.g., for specific treatments, as well as updates, and for receiving information from the orthopedic treatment device 10, for example, about the treatment, such as accumulated dosimetry and/or other treatment characteristics.

In some embodiments, the power source can provide power for a 30 minute treatment per charge. In some embodiments, the power source can provide power for more than 30 minutes of treatment per charge. The number of treatments/day will vary depending on the physician's prescription or treatment plan. In some embodiments, the charge time can be in the range of about 15, 30, 45, 60, 120, or more minutes. In other embodiments, the charge time can be less than 30 minutes. In some embodiments, the maximum number of treatments would be one treatment per hour. In some embodiments, the internal power source such as lithium ion batteries would provide power so that the internal invention device 10 can provide treatments for 2-3 days. The internal orthopedic treatment device 10 may be able to be re-charged by an external magnetic generator through induction. Once the batteries are re-charged, the internal orthopedic treatment device 10 can run independently. The internal orthopedic treatment device 10 may give treatments that can be intermittent for a pulsing sequence for at least about 1, 2, 3, 6, 8 or more hours, up to about 1, 2, 3, 4, 6, 8 or more times per day. The internal orthopedic treatment device 10 can run continuously emitting a pulsed electromagnetic field for multiple days stimulating the fracture 20 to heal.

In embodiments, the power source and controller 220 are disposed within the body unit 200 with the electromagnetic field emitter 210. In other embodiments, the power source and/or the controller 220 may be disposed in the body unit 200, but remote from the electromagnetic field emitter 210. In such an arrangement, the wires or leads may extend outside of the body unit 200 through the cable port 224 and connect to the remotely disposed controller 220 and/or power supply.

In certain embodiments, the body unit 200 can also include a secure tab 240 that includes a screw hole 242. The screws 120 can be used to secure the body unit 200 to the bone plate 100 and bone 20. The body unit 200 can also include a clearance pocket 250 for the screw 120 of the bone plate 100. This can allow for the screw 120 to be inserted into the bone plate 100 and fractured bone 20. The clearance pocket 250 on the bottom side of the body unit 200 allows for the body unit 200 to be secured flush to the bone plate 100 such that the body unit 200 can be installed without gaps between the body unit 200 and the bone plate 100. Similarly, the bottom side of the body unit 200 can include a curvature 260 such that the body unit 200 mates to the shape and size of the bone plate 100. The curvature 260 on the bottom side of the body unit 200 allows for the body unit 200 to be secured flush to the body plate 100 such that the body unit 200 can be installed without gaps between the body unit 200 and the bone plate 100.

The components of the invention will be in a hermetically sealed case so that all battery components and any other electronics are confined within the body unit 200.

In some embodiments, the emitter coils 210 are position in close proximity to the fracture of the bone 20 to maximize the electromagnetic field density through the fracture increasing fracture stimulation and enhancing the biological effect. To enhance the electromagnetic field strength and penetration, the emitter coils 210 can be wrapped multiple times around a ferrite core 212. Multiple emitter coils 210 may be positioned in series or have moving coils that can be placed in the optimal location close to the fracture sight of the bone 20. The emitter coils 210 can be positioned parallel to the bone plate 100 or positioned slightly angled so that they are optimally directed towards the surface of the fracture of the bone 20. In another embodiment, the body unit 200 can be shaped with flat surfaces. In other embodiments, the body unit 200 can be shaped with somewhat curved at the undersurface to contour to the geometry of the bone 20. Also, the complete internal orthopedic treatment device 10 can be gradually curved to contour to the surface of the bone 20 for better surface contact.

Figure 4A:
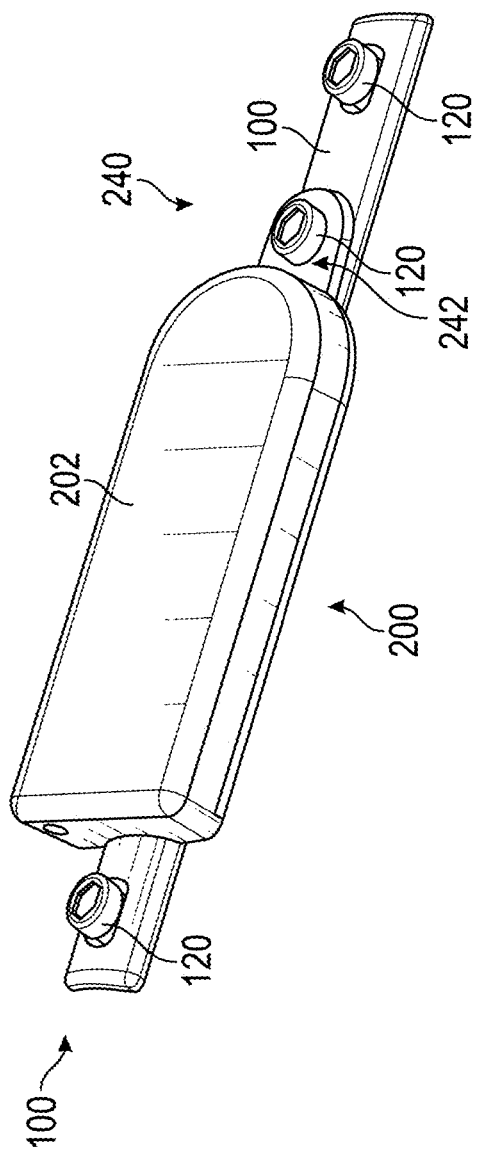
FIGS. 4A-4E illustrate embodiments of the body unit connected to the bone plate.
Figure 4B:
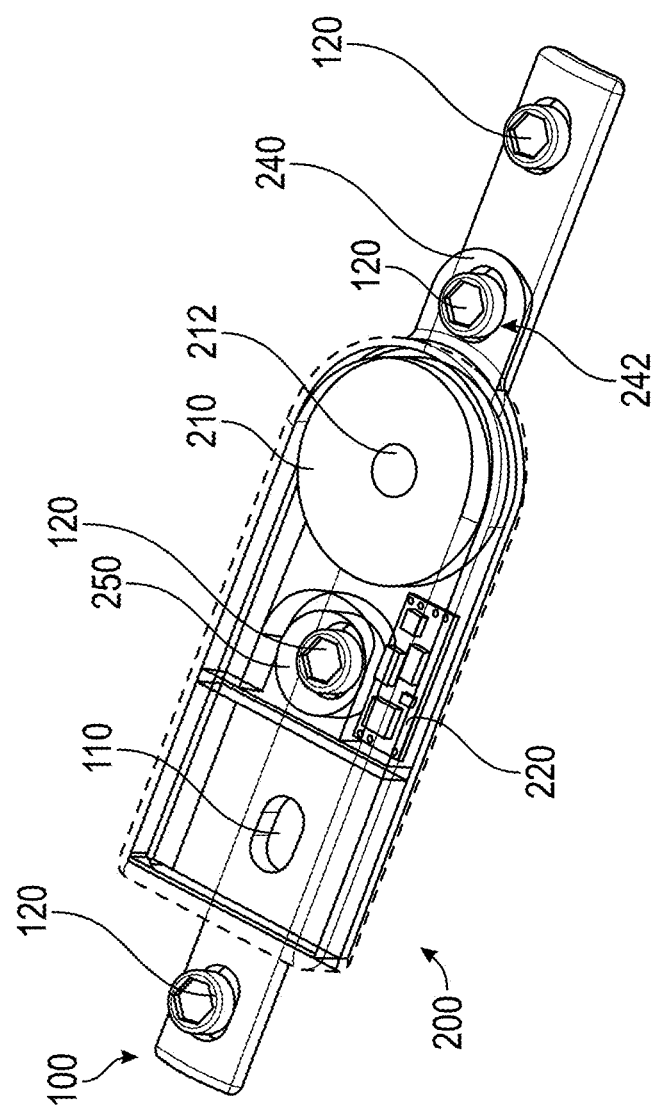

FIG. 4A illustrates the body unit 200 connected to the bone plate 100. The screw 120 can be used to attach the body unit 200 to the bone plate 100. The screw 120 can be installed through the screw hole 242 of the secure tab 240. The body 200 can be enclosed by a cover 202. The cover 202 can be laser welded to seal the body unit 200 and hermetically seal the components contained within the body unit 200 including the battery, the electromagnetic field emitter 210, the controller 220, cabling, and any other components of the body unit 200. The body unit can be fixated to the plate also by 2 or more screws or two or more secure tabs FIG. 4B illustrates the body unit 200 connected to the bone plate 100. FIG. 4B illustrates a transparent cover of the body unit 200 to illustrate the contents of the body unit 200 including the electromagnetic field emitter 210, the controller 220, and the ferrite core 212. As shown in FIG. 4B, not all screw holes 110 must be utilized to fixate the bone plate 100. For example, a screw 120 may not be inserted into the screw hole 110 nearest the fracture on the bone 20 as that can further damage the fractured bone 20. Further, the screw holes 110 can remain unused without screws 120 to allow the body unit 200 to be installed on the bone plate 100 without physical interference of the screw 120. In certain embodiments all screw holes may be filled, while in some embodiment snot all screw holes are filled with screws. In other embodiments, the screws 120 can be installed flush with the body plate 100 such that the heads of the screws 120 are not positioned above the bone plate 100. This can reduce interference with the body unit 200 and allow more screws 120 to be installed to stabilize the bone plate 100. The bone screws 120 can be installed to attach the orthopedic treatment device 10 to the bone 20. Furthermore, the screw hole 110 can be used to install other components, such as a ferrite core 212. The screw holes 110 being used to affix the bone plate 100 to the fractured bone 20. The screw holes 110 can also be used to affix the body unit 200 to the bone plate 100.

In some embodiments, the body unit 200 can also include a ferrite core 212. The ferrite core 212 can be retained with and/or protrude through the unused screw hole 110 of the bone plate 100. The body unit 200 can also include a secure tab 240 that includes a screw hole 242. The screws 120 can be used to secure the body unit 200 to the bone plate 100 and bone 20. The body unit 200 can also include a clearance pocket 250 for the screw 120 of the bone plate 100. The clearance pocket 250 on the bottom side of the body unit 200 allows for the body unit 200 to be positioned over the screw 120. The clearance pocket 250 also allows the body unit 200 to be secured flush to the body plate 100 such that the body unit 200 can be installed without gaps between the body unit 200 and the body plate 100.

Figure 4C:
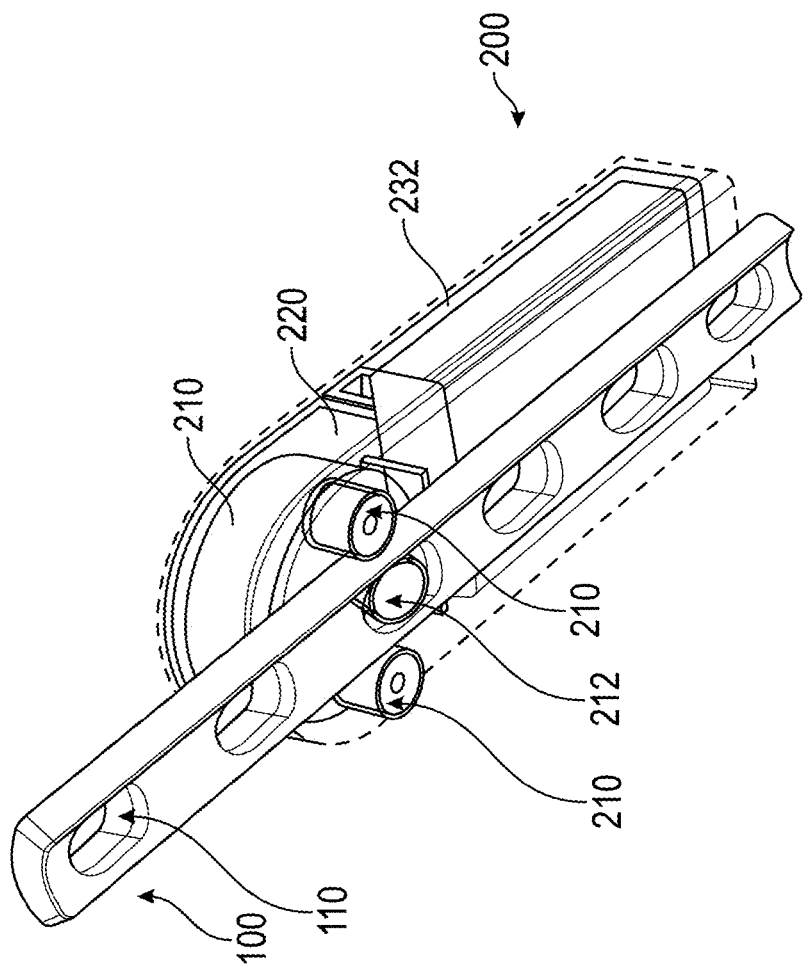

FIG. 4C illustrates another view of the body unit 200 connected to the bone plate 100 of FIG. 4A-B. FIG. 4C illustrates a transparent cover of the body unit 200 to illustrate the contents of the body unit 200 including the electromagnetic field emitter 210, the controller 220, and the ferrite core 212. As shown in FIG. 4C, multiple electromagnetic field emitters 210 of different strengths and sizes may be provided. Additional, smaller electromagnetic field emitters 210 may be included on either side of the bone plate 100 within the body unit.

Figure 4D:
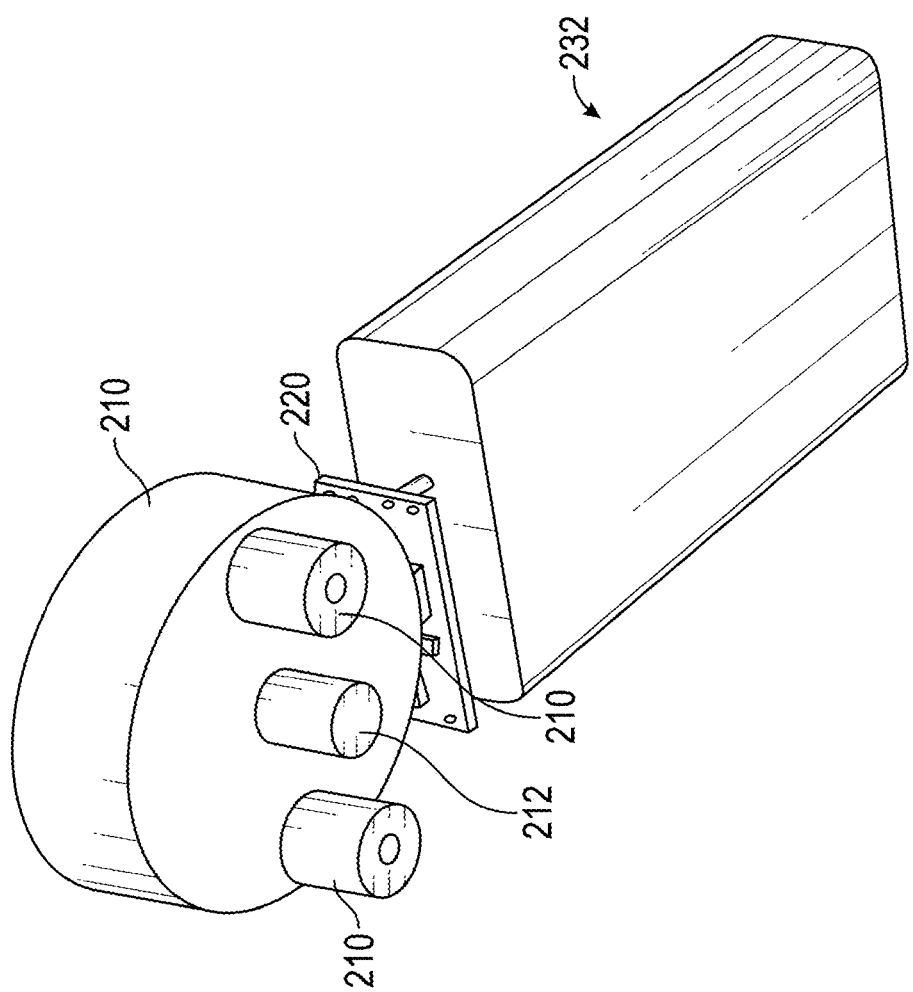

FIG. 4D illustrates a view of the contents of the body unit 200 without the body unit 200 including the electromagnetic field emitters 210, the controller 220, the ferrite core 212, and a power source 232 such as a battery.

Figure 4E:
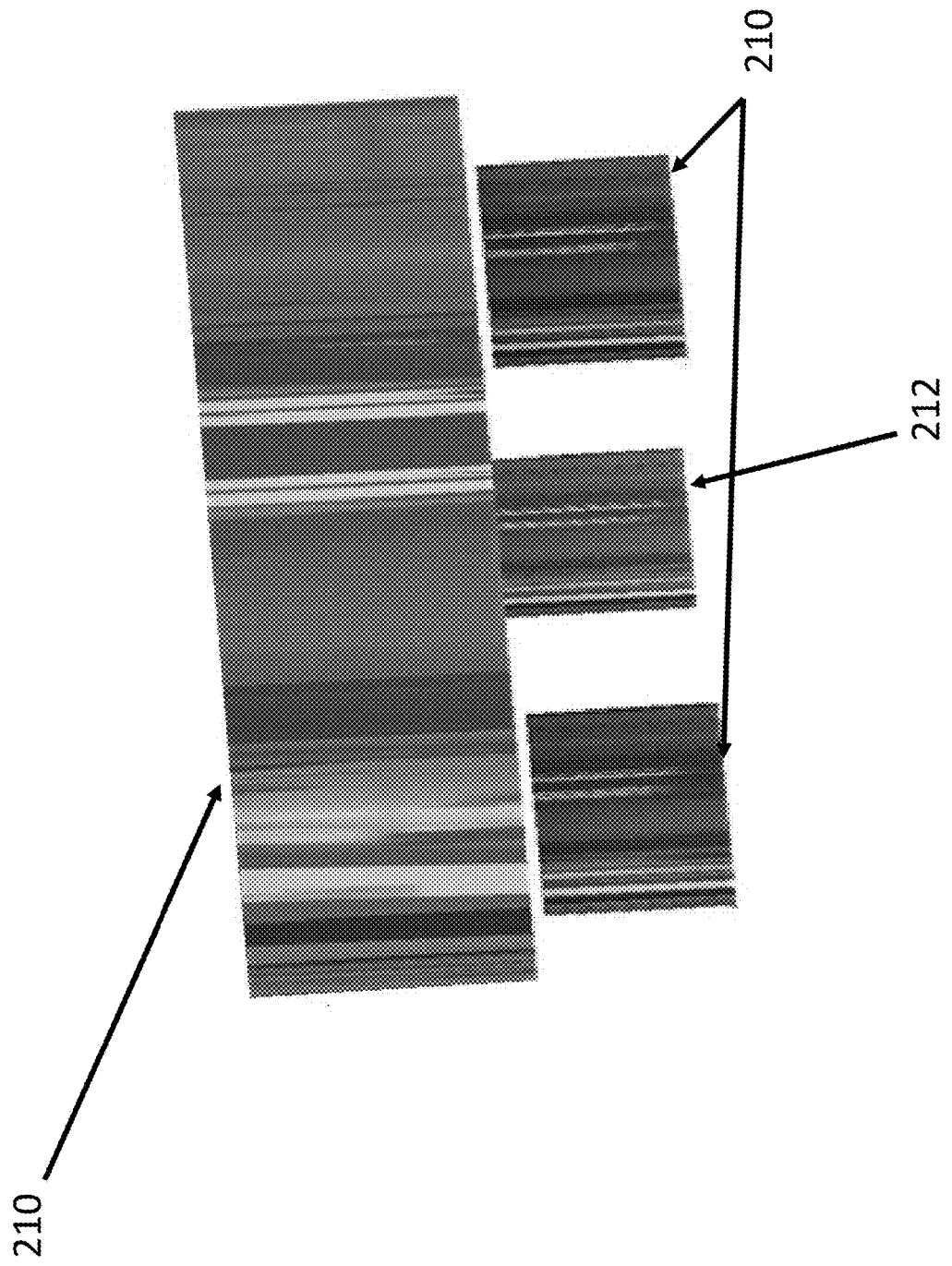

FIG. 4E illustrates the multiple electromagnetic field emitters 210 used in FIGS. 4C-4D. As described above, additional, smaller electromagnetic field emitters 210 may be included. FIG. 4E also illustrates a ferrite core 212 positioned at the center of the electromagnetic field emitter 210.

In some embodiments, the main electromagnetic field emitter 210 may have an outer diameter of approximately 1.0 inches. The electromagnetic field emitter coils 210 may have an outer diameter ranging from approximately 0.1 inch to approximately 1 inch. The electromagnetic field emitter coils 210 may have a thickness of approximately 0.01 inches to approximately 0.1 inches. In some embodiments, the main electromagnetic field emitter 210 may have an inner diameter of 0.2 inches. The electromagnetic field emitter coils 210 may have an inner diameter ranging from approximately 0.1 inches to approximately 1 inch. In some embodiments, the electromagnetic field emitter coils 210 may have a coil length of 0.23 inches. The electromagnetic field emitter coils 210 may have a ferrite length ranging from approximately 0.1 inches to approximately 1 inch.

In some embodiments, the additional electromagnetic field emitters 210 may have an outer diameter of approximately 0.3 inches. The electromagnetic field emitter coils 210 may have an outer diameter ranging from approximately 0.1 inch to approximately 1 inch. The electromagnetic field emitter coils 210 may have a thickness of approximately 0.01 inches to approximately 0.1 inches. In some embodiments, the main electromagnetic field emitter 210 may have an inner diameter of 0.05 inches. The electromagnetic field emitter coils 210 may have an inner diameter ranging from approximately 0.01 inches to approximately 1 inch. In some embodiments, the electromagnetic field emitter coils 210 may have a coil length of 0.15 inches. The electromagnetic field emitter coils 210 may have a coil length ranging from approximately 0.1 inches to approximately 1 inch. In some embodiments, additional ferrite cores (not shown) may be included in the additional electromagnetic field emitter coils 210 as described above.

In some embodiments, the ferrite core 212 may have a diameter of 0.2 inches. In some embodiments, the ferrite core 212 may have a diameter of 0.05 inches. The ferrite core 212 may have a diameter ranging from approximately 0.01 inches to approximately 1 inch. In some embodiments, the ferrite core 212 may have a length of 0.3 inches. In some embodiments, the ferrite core 212 may have a length of 0.15 inches. The ferrite core 212 may have a length ranging from approximately 0.1 inches to approximately 1 inch.

As shown in FIGS. 4A-4B, the body unit 200 can extend past the bone plate 100 such that the sides of the body unit 200 will extend past the bone plate 100 so that contact between the body unit 200 and the bone 20 can be obtained. The electromagnetic emitter coils 210 within the body unit 200 will be positioned past the bone plate 100 so that the emitted electromagnetic field will not have to transverse the plate, which would result in deterioration of the electromagnetic field. The body unit 200 will not extend appreciably past the bone 20 to minimize soft tissue impingement. In addition, the body unit 200 extending minimally past the bone plate 100 also creates an open area to allow soft tissue blood flow to the bone 20.

Once the body unit 200 is fixated to the bone plate 100, the soft tissues may be closed with the body unit 200 maintained internally fixated to the body plate 100 close to the fracture of the bone 20. The orthopedic treatment device 10 can be implanted on the bone 20 such that there is soft tissue under the body unit 200 to allow blood circulation to the fractured bone 20.

FIG. 5A illustrates an embodiment of a bone plate 100 configured for implantation on a fractured bone 20. As shown in FIG. 5A, the bone plate 100 can include a thin metal plate. The bone plate 100 can include one or more screw holes 110 along the length of the bone plate 100. As shown in FIG. 5A, the bone plate 100 can be affixed to a fractured bone 20. Such bone plates 100 are known for placement on a bone 20 to aid, immobilize and properly realign the bone 20 having a fracture. The bone plate 100 can be held in place and affixed to the fractured bone 20 with screws 120 through the screw holes 110 of the bone plate 100. The bone plate 100 can be used to immobilize the fractured bone 20 to properly align the fractured bone 20 and aid in the healing process. The fractured bone 20 is opened in the standard approach. Once the fractured bone 20 is exposed, it is reduced in the correct alignment. The bone plate 100 and multiple screws 120 are applied to stabilize and rigidly maintain the fractured bone 20 in the correct alignment. Once the fractured bone 20 is fixated with the bone plate 100, the body unit 200 is fixated to the bone plate 100 in close approximation to the fracture of the bone 20. Once the body unit 200 is fixated to the bone plate 100, the soft tissues are closed with the body unit 200 maintained internally fixated to the bone plate 100 positioned closely to the fracture of the bone 20.

All screw holes may have screws placed for rigid fixation, however as shown in FIG. 5A, in embodiments not all screw holes 110 have to be utilized to fixate the bone plate 100. For example, a screw 120 may not be inserted into the screw hole 110 nearest the fracture on the bone 20 as that can further damage the fracture site of the bone 20. Further, the screw holes 110 can remain unused without screws 120 to allow the body unit 200 to be installed without physical interference of the screw 120. In some embodiments, the bone plate 100 can include a slotted hole or an elongated hole 112 with round or square ends as shown in FIG. 5A. The slotted hole 112 can allow the screw 120 can be positioned at any point along the slotted hole 112. The slotted hole 112 can also allow the body unit 200 to be positioned at any point along the slotted hole 112. In other embodiments, the screws 120 can be installed flush with the bone plate 100 such that the head of the screw 120 is not positioned above the bone plate 100. This can reduce interference with the body unit 200 and allow more screws 120 to be installed to stabilize the bone plate 100. Furthermore, the screw hole 110 can be used to install other components, such as a ferrite core 212, as discussed more below.

Figure 5B:
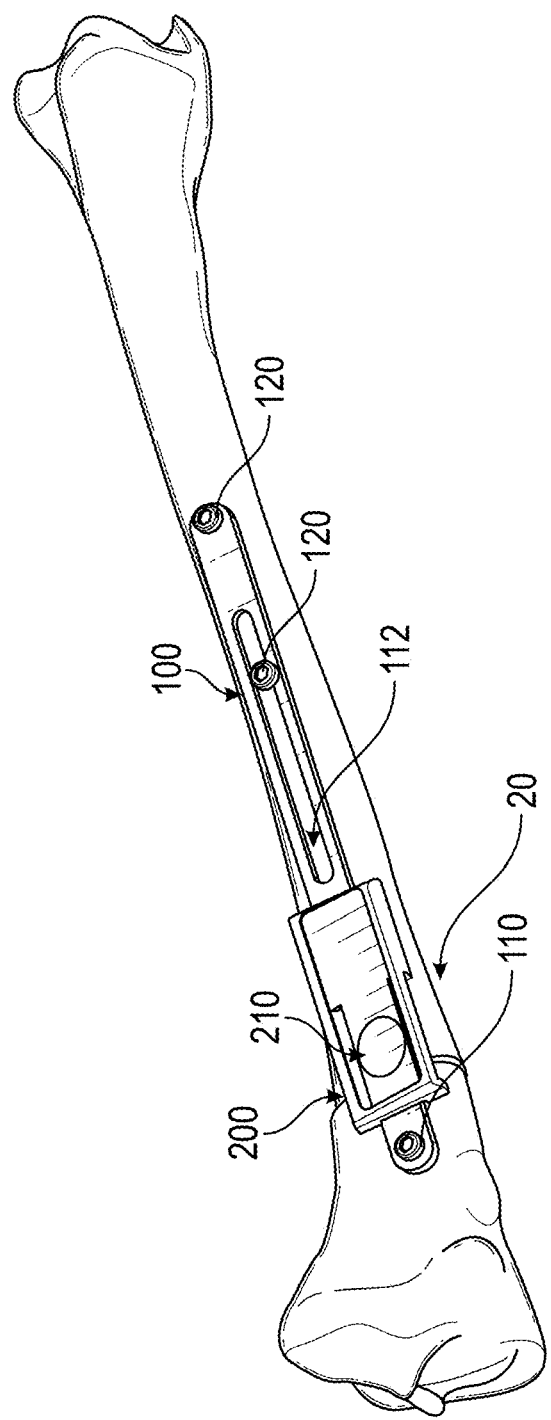
FIGS. 5B-F illustrate embodiments of a body unit.

In other embodiments, all the screws may be placed and the body unit attached to the plate. In addition, the screw holes 110 being used to affix the bone plate 100 to the fractured bone 20, the screw holes 110 can be used to affix the body unit 200 to the bone plate 100 as shown in FIG. 5B. FIG. 5B illustrates an embodiment of a body unit 200 affixed to a bone plate 100 implanted on a fractured bone 20. FIG. 5B illustrates the body unit 200 without the cover 202 to illustrate the components of the body unit 200. The body unit 200 can include an electronics bay, which can contain an electromagnetic field emitter 210, a controller 220, a power source, and any other component. As shown in FIG. 5B, the body unit 200 can be positioned on the bone plate 100 such that the electromagnetic field emitter 210 can be positioned in close proximity to the fracture of the bone 20. The body unit 200 can be located anywhere along the bone plate 100.

Figure 5C:
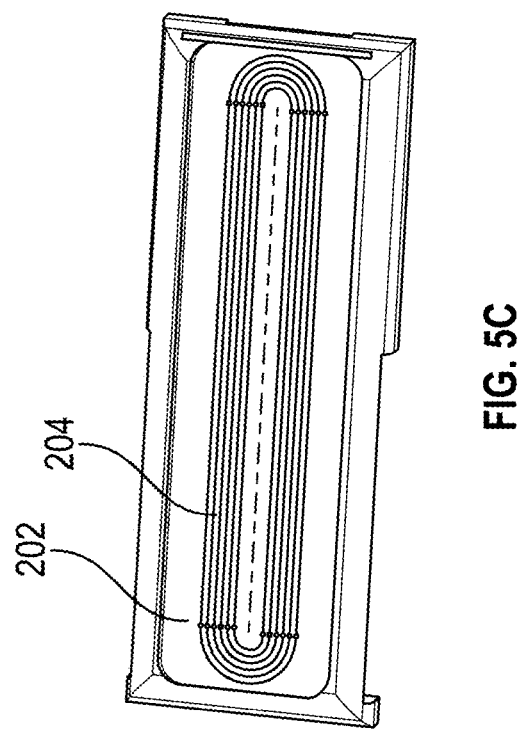

In some embodiments, the controller 220 and/or the power source may be disposed completely outside of the body unit 200. For example, as shown in FIG. 5C, the power source may be a field emitter disposed outside the body unit 200 that emits an electromagnetic field and when placed in proximity to an induction coil 204 disposed in the patient, will charge the coil 204 to power the electromagnetic field emitter 210. The field emitter used as the power supply emits a field that is different from the field generated by the electromagnetic field emitter 210, and which will not adversely affect the wound healing sought to be accomplished by the electromagnetic field emitter 210.

FIG. 5C illustrates an embodiment of a cover 202 with a charging coil 204. Although many of the foregoing embodiments entail implanting a battery as a power source, in some applications a battery may not be the best power source. For example, it may be impractical to use a conventional battery, for example, because the battery may not last long enough. When chronic pain is being treated using an orthopedic treatment device 10, the orthopedic treatment device 10 may need to be able to function as long as the patient requires for an extended period of time. Thus, the orthopedic treatment device 10 may further include an induction coil 204 as a rechargeable power source. More specifically, the induction coil 204 is implanted in the patient and an induction device, such as an induction wand, is used external to the patient to charge the device. The charging wand may take any known form including being provided in a wearable device that could charge the internal orthopedic treatment device 10, for example, when the user is sleeping.

As shown in FIG. 5C, in embodiments, at the surface of the body unit 200 facing the outside environment, opposite the surface of the fractured bone 20, an electromagnetic receiving coil 204 may be positioned for receiving power from an external source through induction. An outside electromagnetic generator will be closely positioned to the skin surface in close proximity to the internal receiving coil 204. The external generator may emit an electromagnetic field inductively charging the internal receiving coil 204 attached to the surface of the body unit 200. The internal receiving coil 204 may be connected to the battery power source to re-charge the internal power source. The internal receiving induction coil 204 may be connected to a microprocessor controller 220 that will modify the electrical current from the internal induction coil 204 so that the current can be utilized by the batteries for re-charging. Once the internal power source is re-charged, the orthopedic treatment device 10 will be able to generate a series of treatment regimens over a specific length of time independently on its internal power source, improving patient compliance.

In embodiments, the external generator or charger wand may be applied externally at the charge location. In some embodiments, during the charging process, the treatment parameters may be set. The orthopedic treatment device 10 may then start the treatment based on the timing parameters. These timing parameters may be spaced over a longer than one hour interval. In some embodiments, after a predetermined time interval as set by the treatment parameters, the external generator or charger wand may then be applied again to recharge the internal orthopedic treatment device 10 and initiate the treatment. In some embodiments, the external generator or charger wand may be applied at selected times of the day or week or predetermined interval.

In some embodiments, the internal orthopedic treatment device 10 can also be run by the external magnetic generator independently through the pick-up coil with a direct connection to the PC boards, controller 220 and emitter coils 210. The internal power source can be bypassed if necessary and the internal orthopedic treatment device 10 can be run solely by the external magnetic generator. The external magnetic generator will be power by a cord and connected to a standard socket to provide electricity to the external generator.

In some embodiments, sensors located on the internal induction coil 204 and external generator may communicate when the internal induction coil 204 and external generator are lined up for induction charging to proceed. This communication can be provided by Bluetooth or any other communication device. When the internal batteries must be charged, the external generator can be placed on the patient in the proximity of the internal receiving coil 204. In some embodiments, the external generator can be placed in a different location externally oriented towards the fracture 20. In some embodiments, this external charging process may occur at night, when the patient is sleeping, or any other time of the day to re-charge the internal batteries. In some embodiments, the external generator may treat the bone fracture 20 at the same time that it is re-charging the internal power source. In some embodiments, the external generator may simultaneously treat the fractured bone 20 as the internal emitter coils 210 provide treatment thereby creating a Hemholtz effect across the fracture 20 and increase the magnetic field strength across the fracture 20 for greater bioeffect.

In some embodiments, the external generator may be stabilized to the external skin in proximity to the internal device by adhesive, straps or alternative fastening devices. In some embodiments, the external generator may be held in close proximity to the internal orthopedic treatment device 10 with a stand, so the external generator does not make contact with the surgically repaired area, which may be sensitive until further healing.

Figure 5D:
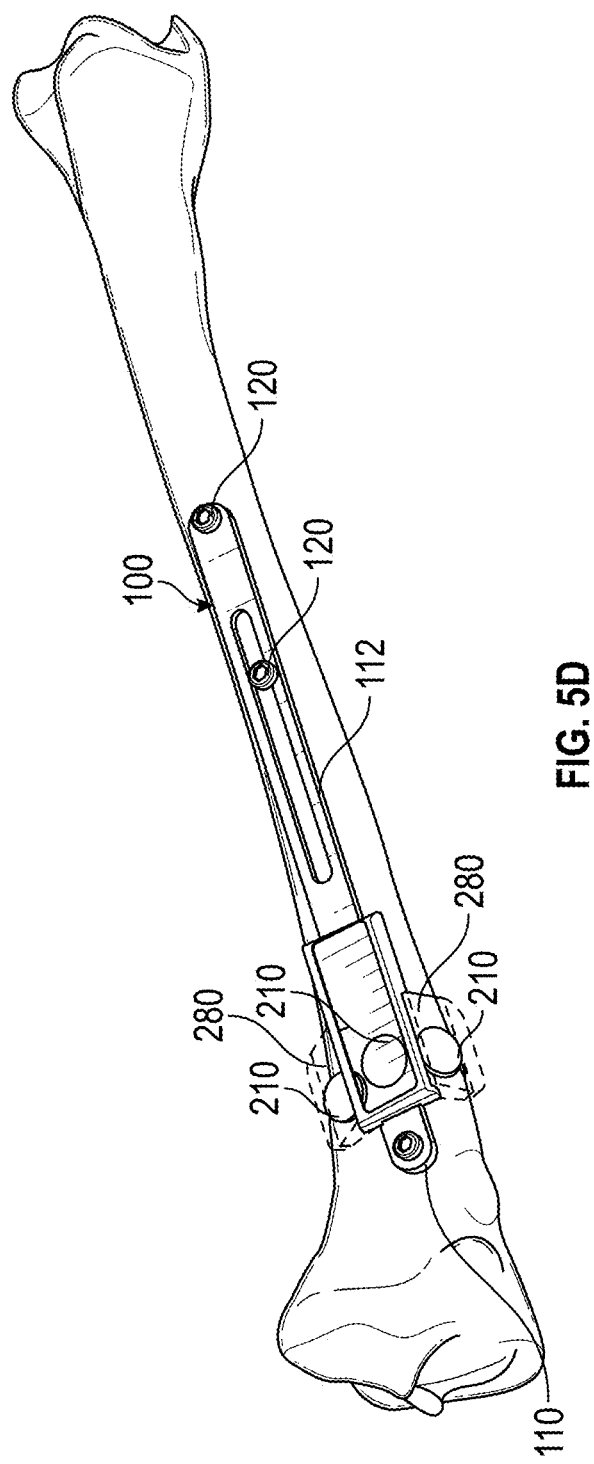
Figure 5E:
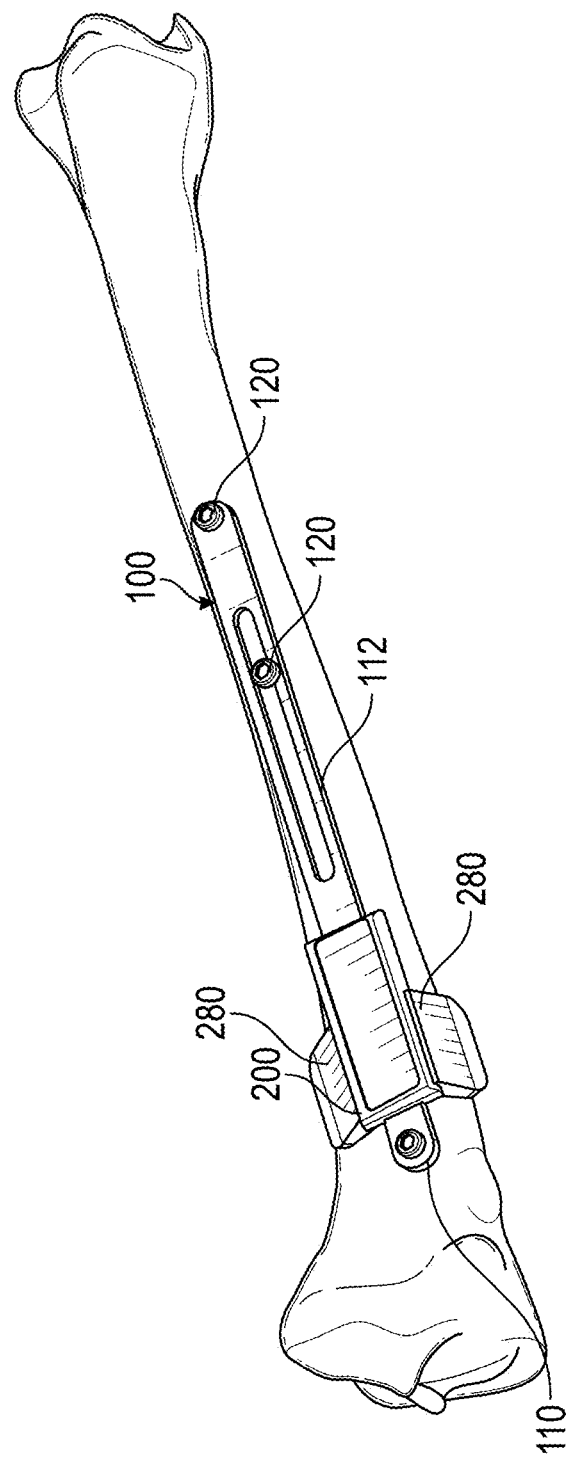
Figure 5F:
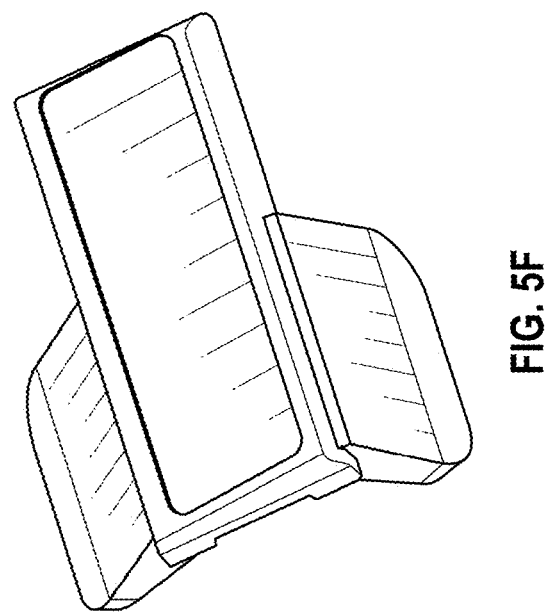

FIG. 5D illustrates another embodiment of a body unit 200 affixed to a bone plate 100 implanted on a fractured bone 20. FIG. 5D illustrates the body unit 200 without the cover 202 to illustrate the components of the body unit 200. The body unit 200 can include an electronics bay, which can contain an electromagnetic field emitter 210, a controller 220, a power source, and any other component. As shown in FIG. 5D, the body unit 200 can be positioned on the bone plate 100 such that the electromagnetic field emitter 210 can be positioned in close proximity to the fracture of the bone 20. The body unit 200 can be located anywhere along the bone plate 100. As shown in FIG. 5D, the body unit 200 may include two extension portions 280 that extends on either side of the body unit 200. FIG. 5D illustrates the body unit 200 without the cover 202 to illustrate the components of the body unit 200. FIG. 5E illustrates the embodiment of the body unit 200 of FIG. 5D. FIG. 5F illustrates the embodiment of the body unit 200 of FIGS. 5D-5E. FIG. 5F illustrates the embodiment of the body unit 200 not affixed to the bone plate 100 implanted on a fractured bone 20.

In some embodiments, these extensions portions 280 can be tabs, wings, flaps, or extensions. In some embodiments, there may be a single wing portion 280, two wing portions 280 or more than two extension portions 280. The wing portions 280 may include an electromagnetic field emitters 210. In some embodiments, the wing portions 280 may be rotated towards the bone to minimize the space between the wing portions 280 and the fractured bone 20. In some embodiments, the electromagnetic field emitters 210 may surround the fracture 20 may surround ranging from 45 degrees to 180 degrees. This range may increase depending on the number, size, and orientation of the wing portions 280 and electromagnetic field emitters 210 enclosed therein.

Figure 6:
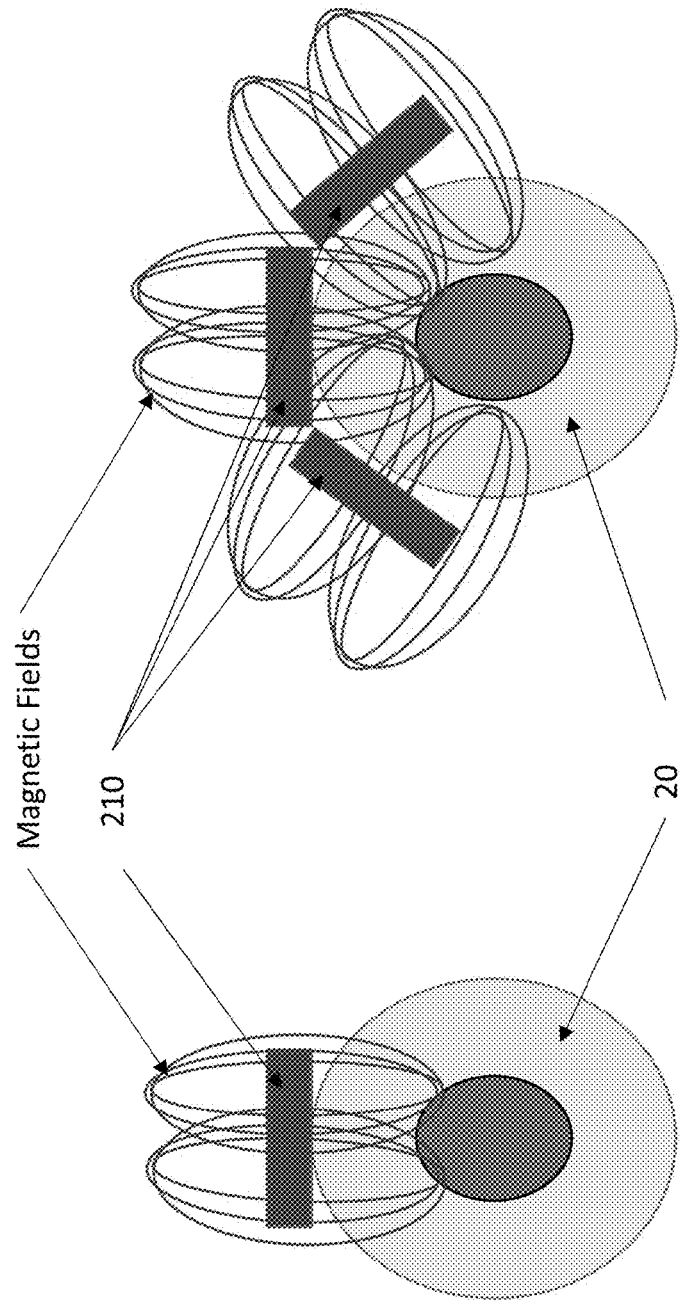
FIG. 6 illustrates an embodiment of multiple coils.

FIG. 6 illustrates the advantage of multiple electromagnetic field emitters 210 implanted on the fractured bone 20. FIG. 5G illustrates magnetic fields created by the electromagnetic field emitters 210. Multiple electromagnetic field emitters 210 implanted on the fractured bone 20 creates a larger range of coverage of the magnetic field than a single electromagnetic field emitter 210.

FIG. 7A illustrates an embodiment of a bone plate 100. As shown in FIG. 7A, the bone plate 100 can include a thin metal plate, similar to the bone plate 100 shown in FIG. 2. The bone plate 100 can include one or more screw holes 110 along the length of the bone plate 100. Such bone plates 100 are known for placement on a bone 20 to aid, immobilize and properly realign the bone 20 having a fracture. The bone plate 100 can be held in place and affixed to the fractured bone 20 with screws (not shown) through the screw holes 110 of the bone plate 100. The bone plate 100 can be used to immobilize a fractured bone (not shown) to properly align the fractured bone (not shown) and aid in the healing process. The fractured bone is opened in the standard approach. Once the fractured bone is exposed, it is reduced in the correct alignment. The bone plate 100 and multiple screws are applied to stabilize and rigidly maintain the fractured bone 20 in the correct alignment.

In embodiments, the bone plate 100 may be a surgical or orthopedic plate. The bone plate 100 may be any known plate or plate-like structure, for example, such as used to maintain position of a fractured bone for healing that bone or for fusion of bones, as in spinal surgery. The bone plate 100 may be fabricated in a size and shape that give it sufficient strength to stabilize the fracture of the bone during healing. The bone plate 100 may be fabricated from a material that permits an electromagnetic field to pass therethrough. The bone plate 100 may be made of material that is non-ferrous, such that the emitted electromagnetic field will readily pass through the bone plate 100 to the treatment area.

The bone plate 100 may be made from a material that will not distort the field generated by the electromagnetic field emitter 210, but the electromagnetic field emitter 210 and the bone plate 100 may be designed to cooperate in creating a field that will effectively intersect with a fracture or wound. In some embodiments, the body unit 200 may be made of titanium or stainless steel.

FIG. 7B illustrates a close up view of the bone plate 100 of FIG. 7A. As shown in FIG. 7B, the bone plate 100 may have a diameter of approximately 10 mm. As shown in FIG. 7B, the screw holes 110 of the bone plate 100 may have a short diameter of approximately 2.5 mm. As shown in FIG. 7B, the screw holes 110 of the bone plate 100 may have a long diameter of approximately 7.5 mm. As shown in FIG. 7B, the screw holes 110 of the bone plate 100 may be spaced at approximately 17.5 mm from center to center of each screw hole 110.

One of skill in the art will understand that in some examples or embodiments, the bone plate may have a diameter of approximately 4 mm, 5 mm, 10 mm, 11 mm, 13.5 mm, or 17.5 mm. In some embodiments, the screw holes 110 of the bone plate 100 may have a short diameter of approximately 1 mm, 2 mm, 3 mm, 4 mm or 5 mm. In some embodiments, the screw holes 110 of the bone plate 100 may have a long diameter of approximately 5 mm, 6 mm, 7 mm, 8 mm, 9 mm or 10 mm. In some embodiments, the screw holes 110 of the bone plate 100 may be spaced at approximately 15 mm, 16 mm, 17 mm, 18 mm, 19 mm, or 20 mm from center to center of each screw hole 110.

In some embodiments, the dimensions of the bone plate 100 may be approximately sized to treat and stabilize the size, position, location, and nature of the fracture of the bone 20.

As shown in FIG. 8A, in embodiments the body unit 200 can have an approximate dimension similar to the bone plate 100 such that the body unit 200 does not extend past the bone plate 100 to minimize the amount of space the body unit 200 occupies once implanted into the patient. Once the body unit 200 is fixated to the bone plate 100, the soft tissues are closed with the body unit 200 maintained internally fixated to the body plate 100 close to the fracture of the bone. The body unit 200 will not extend appreciably past the fractured bone to minimize soft tissue impingement. In addition, the body unit 200 extending minimally past the bone plate 100 also creates an open area to allow soft tissue blood flow to the bone 20.

FIG. 8A illustrates the body unit 200 without the cover to illustrate the internal components of the body unit 200. The body unit 200 can be self-contained and implanted into the patient. As shown in FIG. 8A, the body unit 200 can be attached to the body plate 100 that is used for open reduction and internal fixation of a fracture of a bone 20. The internal components of the body unit 200 can include an electromagnetic field emitter 210. The body unit 200 may also include a ferrite core 212 positioned within the electromagnetic field emitter 210. The ferrite core 212 may also be positioned within the electromagnetic field emitter and extend through the screw holes 110 of the bone plate 100. The ferrite core 212 can be retained with and/or protrude through the unused screw hole 110 of the bone plate 100.

Figure 8B:
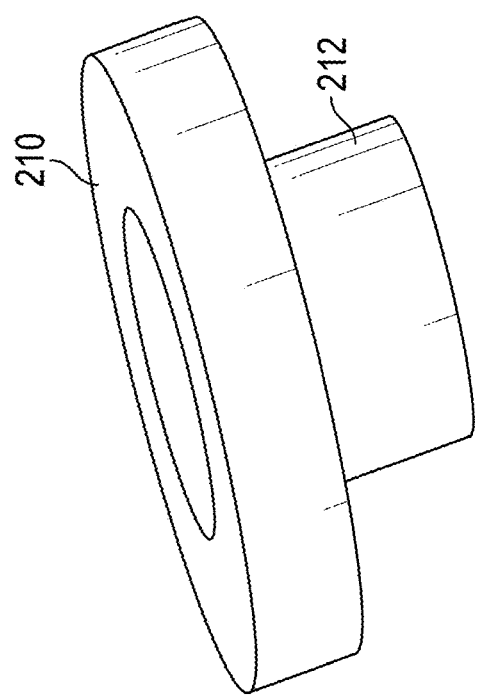
FIG. 8B illustrates an embodiment of the electromagnetic field emitter and ferrite core.

FIG. 8B illustrates the electromagnetic field emitter 210 and the ferrite core 212 that fits within the center of the electromagnetic field emitter 210. FIG. 8B illustrates the electromagnetic field emitter 210 used in FIG. 8A. FIG. 8B also illustrates a ferrite core 212 positioned at the center of the electromagnetic field emitter 210.

In some embodiments, the electromagnetic field emitter 210 may have an outer diameter of approximately 8 to 10 mm. In some embodiments, the electromagnetic field emitter coils 210 may have an outer diameter ranging from approximately 0.1 inch to approximately 1 inch. The ferrite core 212 may have an outer long diameter of approximately 2.5 mm. In some embodiments, the ferrite core 212 may have a diameter of approximately 1 mm to approximately 5 mm.

Figure 9A:
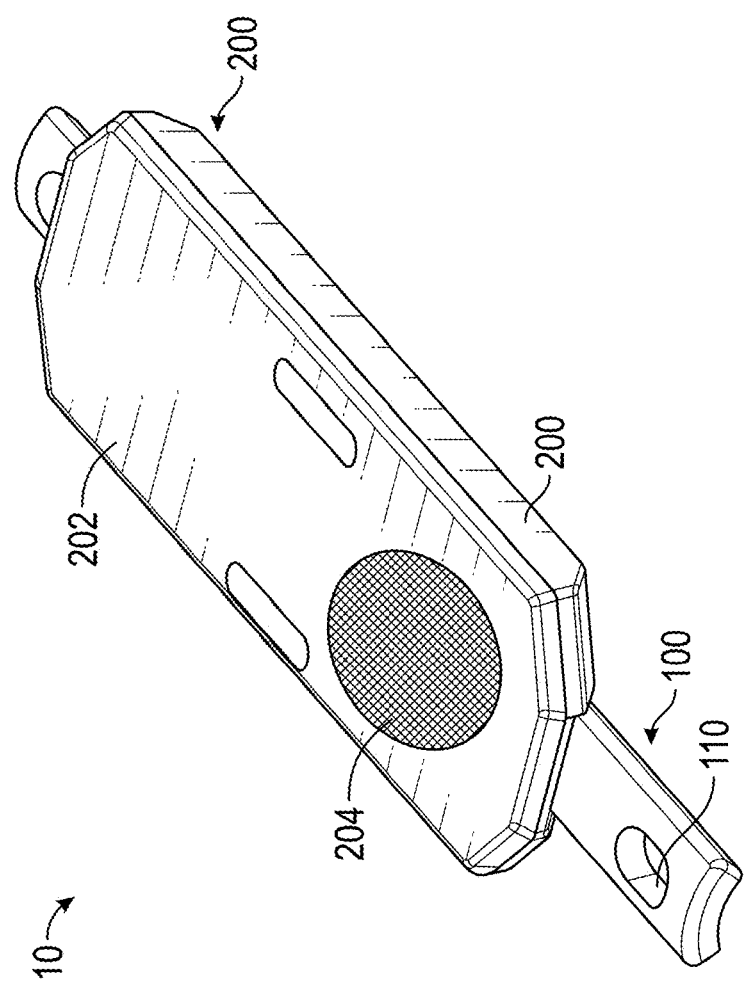
FIG. 9A illustrates another embodiment of an orthopedic treatment device configured for implantation on a fractured bone.

FIG. 9A illustrates another embodiment of an orthopedic treatment device 10 including a bone plate 100 and body unit 200 configured for implantation on a fractured bone 20. FIG. 9A illustrates the body unit 200 with a cover 202 with a charging coil 204. At the surface of the body unit 200 facing the outside environment, an electromagnetic receiving coil 204 may be positioned for receiving power from an external source through induction. As shown in FIG. 9A, the receiving coil 204 can be positioned on a portion of the cover 202. The receiving coil 204 can be positioned near the battery or the internal power source of the body unit 200. An outside electromagnetic generator will be closely positioned to the skin surface in close proximity to the internal receiving coil 204. The external generator may emit an electromagnetic field inductively charging the internal receiving coil 204 attached to the surface of the body unit 200. The internal coil 204 may be connected to the battery power source to re-charge the internal power source. The internal receiving induction coil 204 may be connected to a microprocessor controller 220 that will modify the electrical current from the internal induction coil 204 so that the current can be utilized by the batteries for re-charging. Once the internal power source is re-charged, the body unit 200 can generate a series of treatment regimens over a specific length of time independently on its internal power source, improving patient compliance.

Figure 9B:
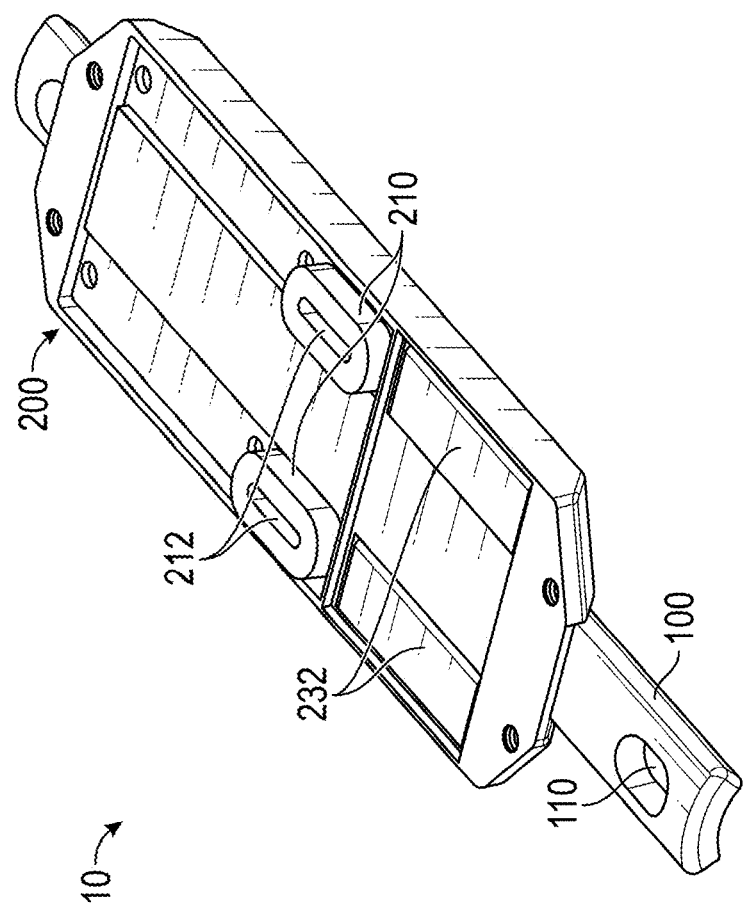
FIG. 9B illustrates the orthopedic treatment device of FIG. 9A with the cover removed.

FIG. 9B illustrates an embodiment of the orthopedic treatment device 10 of FIG. 9A including a bone plate 100 and the body unit 200 with the cover 202 removed. The body unit 200 can include an internal power source 232. The internal power source 232 can include one or more lithium ion batteries 232. In some embodiments 2, 4, 6, 8, 10 or more batteries may be used. The body unit 200 can include two coil emitters 210 as shown in FIG. 6B. The body unit 200 can also include two ferrite cores 212 within the coil emitters 210. As shown in FIG. 9B, the body unit 200 may be constructed so that its mid portion is positioned over the bone plate 100. The body unit 200 may extend past the bone plate 100 to rest on the bone 20. The body unit 210 may rest or come into contact with the surface of the bone 20 on either side of the bone plate 100. Each of the two extensions are positioned so that they rest on the surface of the bone in close proximity to the fracture 20. Each extension may be a contained unit that has one or more electromagnetic emitter coils 210. The electromagnetic emitter coils 210 may be positioned on either side of the bone plate 100 in close proximity to the surface of the fractured bone 20.

In some embodiments, the electromagnetic emitter coils 210 may be positioned at the longitudinal mid-line of the body unit 200 facing the fracture 20 such that the fracture 20 is exposed to the greatest electromagnetic fields possible to obtain greater bioeffect and accelerated healing.

Figure 9C:
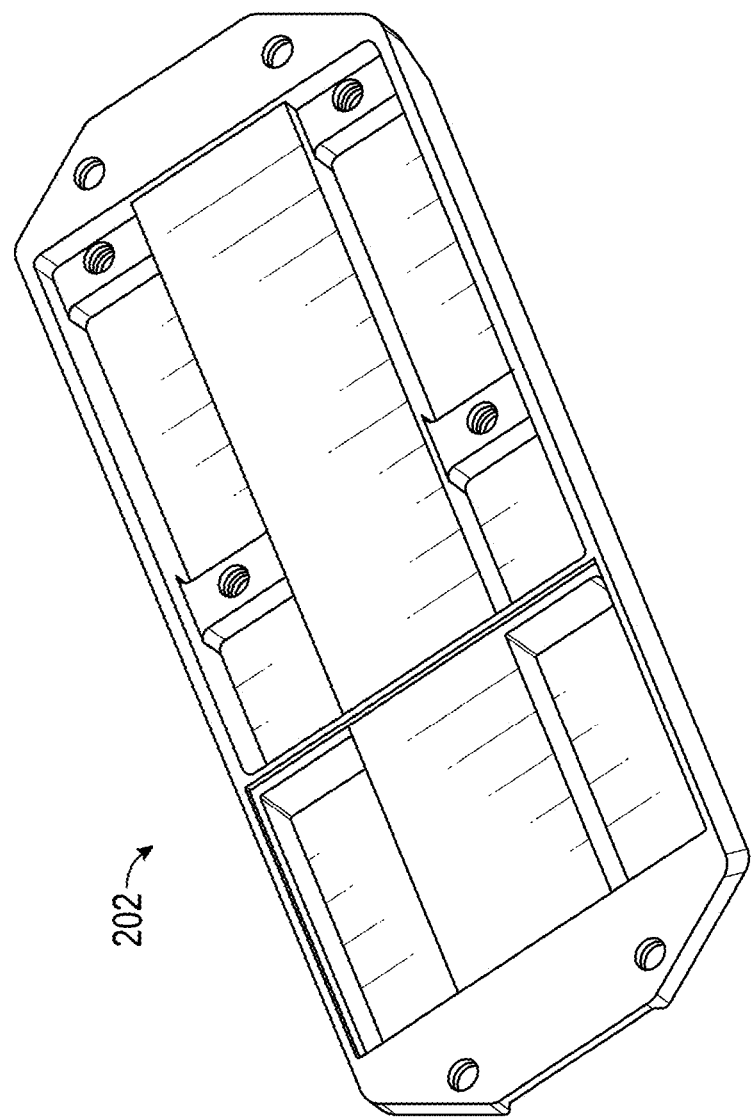
FIG. 9C illustrates the cover of the body unit of the orthopedic treatment device of FIGS. 9A-9B.

FIG. 9C illustrates the cover 202 of the body unit 200 as shown in FIGS. 9A-9B. The cover 202 may be made of titanium or any other medical grade material suitable for implants. The cover 202 may be appropriately sized and shaped to cover the body unit 200 and receive around the components within the body unit 200. As shown in FIG. 9C, the cover 202 may contain clearance pockets and compartments to receive the components within the body unit 200. The components of the body unit 200 may be completely encapsulated within the body unit 200. The clearance pockets and compartments may be laser welded after installation to seal the components within the body unit 200. The body unit 200 including the cover 202 may have machined channels to accommodate internal wiring between the components of the body unit 200. After installation of wires, the channels may be potted to hermetically sealed enclosures within the device.

FIG. 9D illustrates an embodiment of the body unit 200 configured for implantation on a fractured bone 20 as shown in FIGS. 9A-9C. FIG. 9D illustrates the engineering drawings of the body unit 200. In some embodiments, the body unit 200 may have a length of approximately 3 inches and a width of approximately 1 inch. In some embodiments, the body unit 200 may have a height ranging approximately 0.2 inches to approximately 0.5 inches. In certain embodiments the length may be from about 0.1-20 inches, 1-15 inches, 2-10 inches, 3-8 inches, 4-6 inches, or about 5 inches. In certain embodiments, the width may be from 0.05 to 5 inches, 0.5 to 4 inches, 1 to 3 inches, or about 2 inches. In some embodiments, the height may be from approximately about 0.01 to 2 inches, about 0.1 to 1 inches, or about 0.2 to 0.5 inches.

FIG. 9E illustrates an embodiment of an electromagnetic field emitter 210 as shown in FIG. 9B. FIG. 9B illustrates the engineering drawings of the body unit 200. In some embodiments, the electromagnetic field emitter 210 may be an oval shape coil. In some embodiments, the electromagnetic field emitter 210 may have a long diameter of approximately 0.5 inches. In some embodiments, the electromagnetic field emitter 210 may have an outer short diameter of approximately 0.25 inches. In some embodiments, the electromagnetic field emitter 210 may have inner long diameter of approximately 0.25 inches. In some embodiments, the electromagnetic field emitter 210 may have an inner short diameter of 0.06 inches. In some embodiments, the electromagnetic field emitter 210 may have a height of approximately 0.25 inches.

In embodiments, the body unit 200 can extend past the bone plate 100 such that the sides of the body unit 200 will extend past the bone plate 100 so that contact between the body unit 200 and the bone 20 can be obtained. The electromagnetic emitter coils 210 within the body unit 200 will be positioned past the bone plate 100 so that the emitted electromagnetic field will not have to transverse the plate, thereby enhancing the magnetic field at the fixation site. The body unit 200 will not extend appreciably past the bone 20 to minimize soft tissue impingement. In addition, the body unit 200 extending minimally past the bone plate 100 also creates an open area to allow soft tissue blood flow to the bone 20.

Although one electromagnetic field emitter 210 is illustrated in FIG. 3A, FIG. 5B, more than one electromagnetic field emitter 210 may be provided.

Figure 10A:
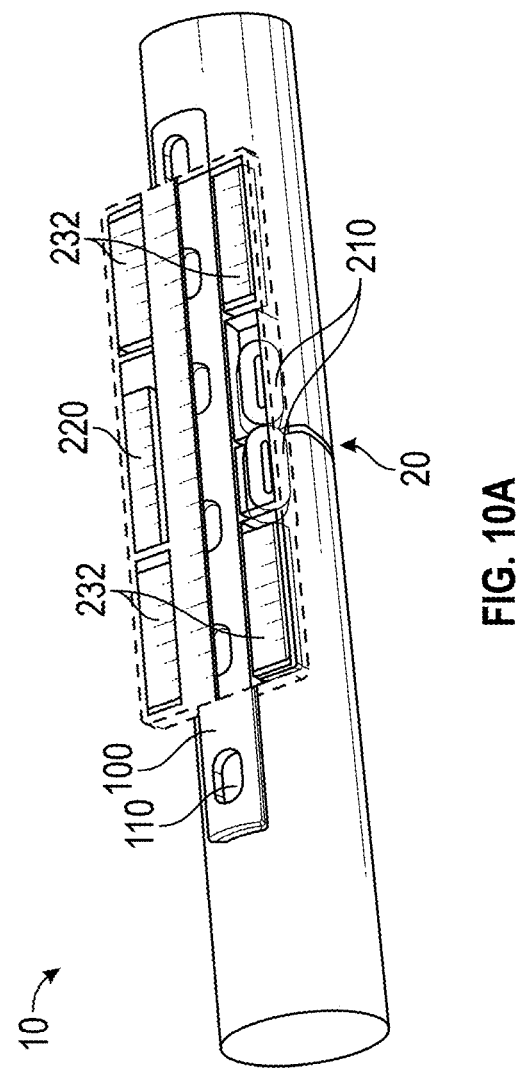
FIG. 10A illustrates another embodiment of an orthopedic treatment device implanted on a fractured bone.

For example, as shown in FIG. 9B, two electromagnetic field emitters 210 may be positioned on each side of the body unit 200. As shown in FIG. 10A, four electromagnetic field emitters 210 may be positioned, two per side of the body unit 200. In embodiments, there may be 2, 4, 6, 8, 10 or more emitters, positioned 1 to a side, 2 to a side, 3 to a side, 4 to a side, or more than 4 to a side. The electromagnetic field emitter 210 may be at fixed positions inside the body unit 200. The position of the electromagnetic field emitter 210 within the body unit 200 may be dictated by the position of the body unit 200 and the bone plate 100 relative to the position of the fracture of the bone 20. When the bone plate 100 is placed on the bone 20, the electromagnetic field emitter 210 will closely align with the position of the fracture to expose the fracture to the electromagnetic field. The electromagnetic field emitter 210 may be affixed to the inside of the body unit 200 using any known fastener, such as a physical fastener like a set screw 120, or an implant grade adhesive.

As will be appreciated by those of ordinary skill in the art, in embodiments, known electromagnetic field emitters 210 produce electromagnetic fields having a known size and shape. An electromagnetic field emitter 210 may include a conductive wire, such as copper, wound along an axis to form a coil 210. When an electrical current is passed through the coil 210, an electromagnetic field is created. Although not required, the electromagnetic field emitter coil 210 may be wrapped around a cylindrical core 212, which may be a ferrous core 212, to intensify the electromagnetic field.

In use, the electromagnetic field emitter coil 210 should be positioned such that the bone fracture 20 and/or any other tissue to be healed is disposed in the electromagnetic field. The electromagnetic field emitters 210 can generate a field very near to the fracture 20 or other wound to be treated so that the high flux portion of the field can intersect the wound or fracture 20. This close positioning allows for a lower power requirement, because the electromagnetic field need not be as strong as it would need to be if it were generated farther from the fracture 20. An increased biological healing response may be created because the electromagnetic field is not interfered with by passing through surrounding tissue.

In some embodiments, a series of electromagnetic field emitters 210 may be disposed along the length of the an orthopedic treatment device 100, such that the electromagnetic fields overlap along the length of the orthopedic treatment device 100. In this embodiment, any position along the bone plate 100 will be affected by an electromagnetic field. While the caregiver could opt to energize all coils 210 to provide a field along the full length of the bone plate 100, the controller 220 could alternatively be configured to allow for selective energizing of the coils 210. In other embodiments, fewer emitters 210 may be provided that are positioned specifically for affecting the fracture 20 or wound. One or more electromagnetic field emitters 210 may be provided that are moveable within the orthopedic treatment device 100 prior to placement of the orthopedic treatment device 100, to allow the electromagnetic field emitters 210 to be placed at positions that will best promote healing. In yet another embodiment, the electromagnetic field emitters 210 may be placed at predetermined positions within different bone plates 100, with the orthopedic surgeon choosing a bone plate 100 that will align the electromagnetic field emitter 210 with the fracture 20 or wound for healing promotion.

Once in position, screws 120 may be inserted transversely through the fractured bone 20 and into the bone plate 100, to lock the bone plate 100 in place.

In embodiments, because the orthopedic treatment device 10 is generally intended to be left in the patient permanently, the components may be implant grade. Moreover, the body unit 200 and bone plate 100 may be made of a non-ferrous material, such as a polymer or titanium so as not to affect the electromagnetic field emitted by the electromagnetic field emitter 210. The components should be chosen such that the electromagnetic field emitted by the electromagnetic field emitter 210 will pass freely through the orthopedic treatment device 10 to the fractured bone 20 and/or the damaged tissue.

In some embodiments, the internal orthopedic treatment device 10 may position the PC boards and controller 220 on each end of the internal orthopedic treatment device 10 to make more room for the batteries and emitter coils 210 at the treatment locations of the internal orthopedic treatment device 10 and still keep the internal orthopedic treatment device 10 as low profile as possible. The internal orthopedic treatment device 10 can also be a sleeve type configuration in which the shape of the body unit 200 mirrors the bone plate 100 to be used for fixation. The circuit boards, electronics, batteries 232, and induction charge receiving coil 204 may be positioned on the top and/or the sides of the body unit 200 positioned above the bone plate 100. The emitter coils 210 may be positioned at a portion in the body unit 200 under the bone plate 100. The bone plate 100 slides into the sleeve portion of the body unit 200 and the holes 110 of the bone plate 100 are lined up with the holes 110 of the body unit 100. The bone plate 100 and body unit 200 are placed on the surface of the bone centered over the fracture 20. The screws 120 are placed though the holes 110 of the body unit 200 and the bone plate 100 into the bone 20. The screws 120 may be used to stabilize the body unit 200, bone plate 100 and bone complex 20. The emitter coils 210 are located between the undersurface of the bone plate 100 and the fractured bone 20. The components of the internal orthopedic treatment device 10 are in a protective covering made of titanium, or other materials that will protect the coils 210 under the bone plate 100. This places the coils 210 in close proximity to the bone fracture 20 for the greatest bioeffect. The re-charger pick-up coil 202 is at the surface of the body unit 200 facing the skin surface so that it can be re-charged by the external generator coil by induction.

In another embodiment, the body unit 200 may be mounted on the bone plate 100 after the bone plate 100 is screwed in place and the fracture 20 is fixated. The internal orthopedic treatment device 10 may include the body unit 200 centered over the bone plate 100. The electronic circuit boards, batteries 232 and pick up coil 202 incorporated in the body unit 200 over the bone plate 100. The body unit may include two wings that extend past the plate on each side of the bone plate 100 that have the emitter coils 210 inside and in contact with the bone surface at the fracture 20 and with the same contour as the bone. The wings of the body unit 200 may include emitter coils 210. The wings may allow the body unit 200 to have a very low profile over the fracture 20. The main portion of the internal orthopedic treatment device 10 with the batteries 232, PC boards, electronics and batteries located in the body unit 200.

In some embodiments, the electromagnetic field emitter 210 may be a coil 210 carried on the bone plate 100. The emitter 210 may be carried on a side of the bone plate 100 that does not contact the bone 20. In some embodiments, the electromagnetic field emitter 210 and other components may be mounted on or contained within the bone plate 100. In other embodiments, an electromagnetic field emitter or emitters 210 may be fixed at predetermined position(s) on the bone plate 100. In some embodiments, the orthopedic surgeon may affix the electromagnetic field emitter 210 during surgery, using known fastening means, such as adhesives or mechanical fasteners. The surgeon will then choose the appropriate bone plate 100, and place the bone plate 100 to ensure that the emitted field is properly aligned with the fracture of the bone 20. The electromagnetic field emitter 210 may be positioned on an edge of the bone plate 100 or the bottom of the plate 100, proximate the bone 20 to which the bone plate 100 is affixed.

In some embodiments, an electromagnetic field emitter 210 may be disposed in a recess formed in a bone plate 100. The bone plate 100 further includes holes 110 for affixation of the bone plate 100. A controller 220 and a power source 232 may also be contained within the recess of the bone plate 100. The recess allows for a lower-profile arrangement than can be achieved by placing the electromagnetic field emitter 210 on top of the bone plate 100. The recessed portion of the bone plate 100 should be configured to provide sufficient rigidity to stabilize the fracture and minimize the formation of stress risers.

In particular embodiments, the controller 220 and a power supply, which may be connected, may be completely encapsulated within an orthopedic plate 100. In this embodiment, a cavity is provided in the bone plate 100 and the components are disposed in the cavity. In some embodiments, the components including the circuit PC boards, electronics, controller 220, batteries 232, induction coil 204 and emitter coils 210 are incorporated into the bone plate 100. To facilitate formation of the bone plate 100, the bone plate 100 may be made of multiple pieces that are assembled after affixation of the electromagnetic field emitter 210 and other components to one of the pieces. For example, the bone plate 100 may have first and second opposing pieces, such as a top and a bottom having facing horizontal surfaces that when assembled define a cavity sized to receive the electromagnetic field emitter 210 and other components, as appropriate. Alternatively, the bone plate 100 may be formed with a recess, the components placed in the recess, and then a cover applied to substantially encapsulate the components in the bone plate 100. In such embodiments, the surgeon will receive a unitary piece in which is embedded the components, such as the electromagnetic field emitter 210, controller 220 and power supply.

In embodiments, the components are positioned within the bone plate 100 so that, as earlier described embodiments, the emitter coils 210 are positioned in close proximity to the fracture 20 for maximum bioeffect. The batteries 232 and PC circuit boards and induction pick up coil 202 are positioned so that the plate 100 construct is a low profile and the soft tissues can be closed without difficulty. The casing for the internal orthopedic treatment device 10 is made of titanium or other material so as not to impede the outward direction of the magnetic field to the fracture 20 and not to impede the induction of the induction coil to re-charge the batteries 232.

FIG. 10A illustrates another embodiment of an orthopedic treatment device 10 implanted on a fractured bone 20. The orthopedic treatment device 10 may include a bone plate 100 and body unit 200. FIG. 10A illustrates the body unit 200 with the cover 202 removed on one side to illustrate the components contained within the body unit 200. The body unit 200 can include batteries 232, electromagnetic field emitters 210, and a controller 220. In this embodiment, the body unit 200 can include four batteries 232, two per side of the body unit 200. The body unit 200 can also include four electromagnetic field emitters 210, two per side. As described, FIG. 7A illustrates the body unit 200 with the cover removed on one side of the body unit 200, showing two electromagnetic field emitters 210.

Figure 10B:
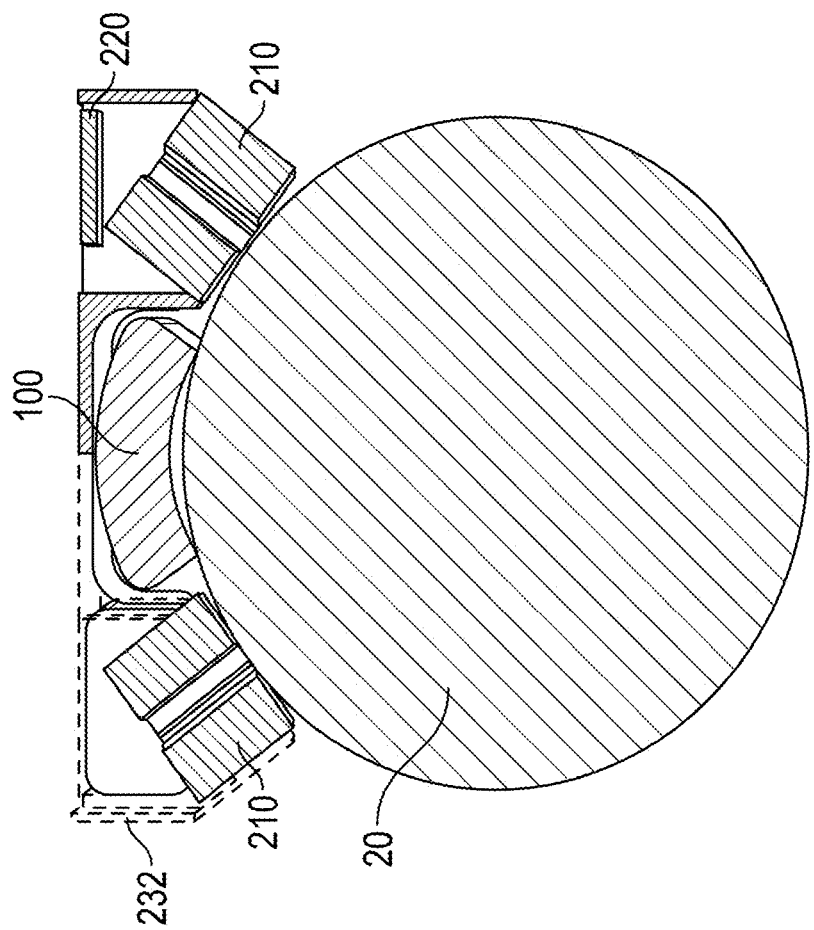
FIG. 10B illustrates a cross sectional view of the orthopedic treatment device of FIG. 10A implanted on a fractured bone.

FIG. 10B illustrates a cross sectional view of the orthopedic treatment device 10 of FIG. 10A implanted on a fractured bone 20. The bone plate 100 positioned and attached to a fractured bone 20 for internal fixation to align the bone 20 for proper healing. The body unit 200 can be positioned and attached to the bone plate 100 such that the electromagnetic field emitters 210 are positioned closely to the fracture of the bone 20. As shown in FIG. 7B, the body unit 200 can be shaped to mate with the bone plate 100. The body unit 200 can contain a curved portion that allows the body unit 200 to mate to the bone plate 100, and the bone allowing the components of the body unit 200 to be positioned closely to the fractured bone 20.

Figure 10C:
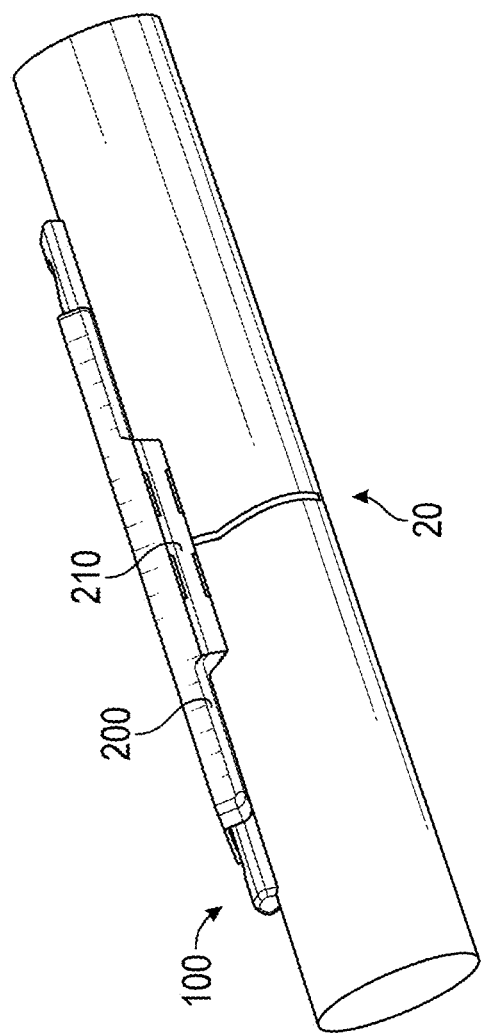
FIG. 10C illustrates a perspective view of the orthopedic treatment device of FIGS. 10A-B implanted on a fractured bone.

FIG. 10C illustrates a perspective view of the orthopedic treatment device 10 of FIG. 10A implanted on a fractured bone 20. The body unit 200 can have the portion containing the electromagnetic field emitters 210 can be angled to minimize the distance from the electromagnetic field emitters 210 to the fractured bone 20.

Figure 10D:
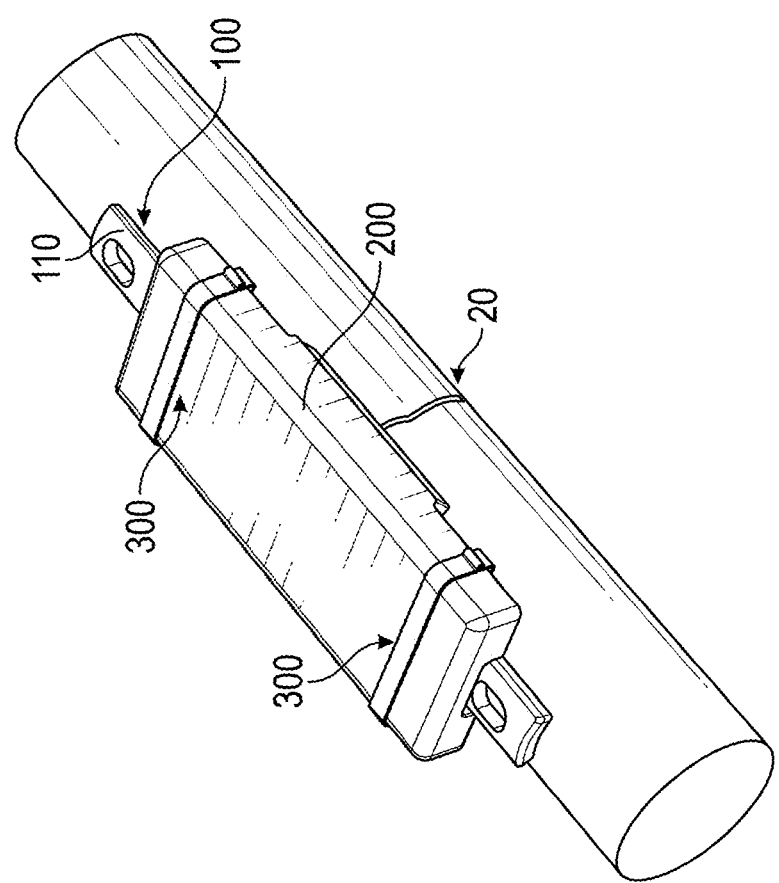
FIG. 10D illustrates the orthopedic treatment device of FIGS. 10A-C implanted on a fractured bone with retaining spring clips.
Figure 10E:
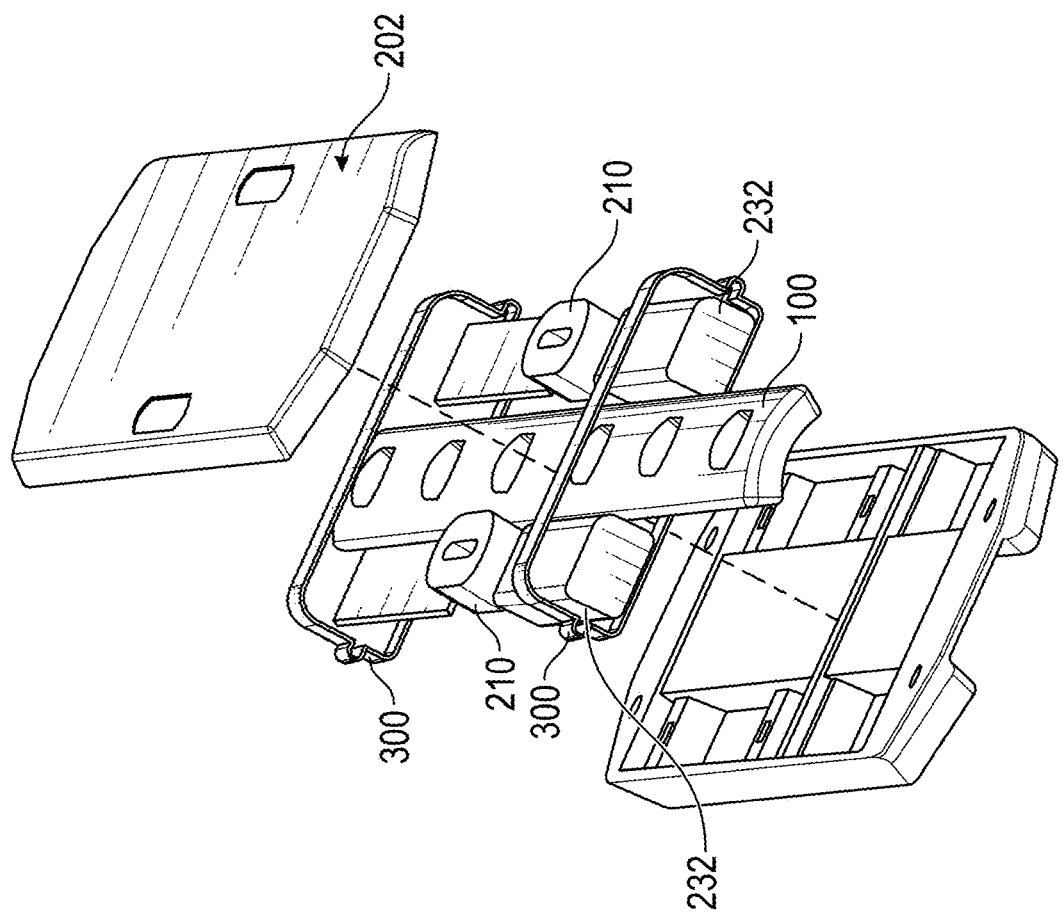
FIG. 10E illustrates a schematic exploded perspective view of the orthopedic treatment device with retaining spring clips.
Figure 10F:
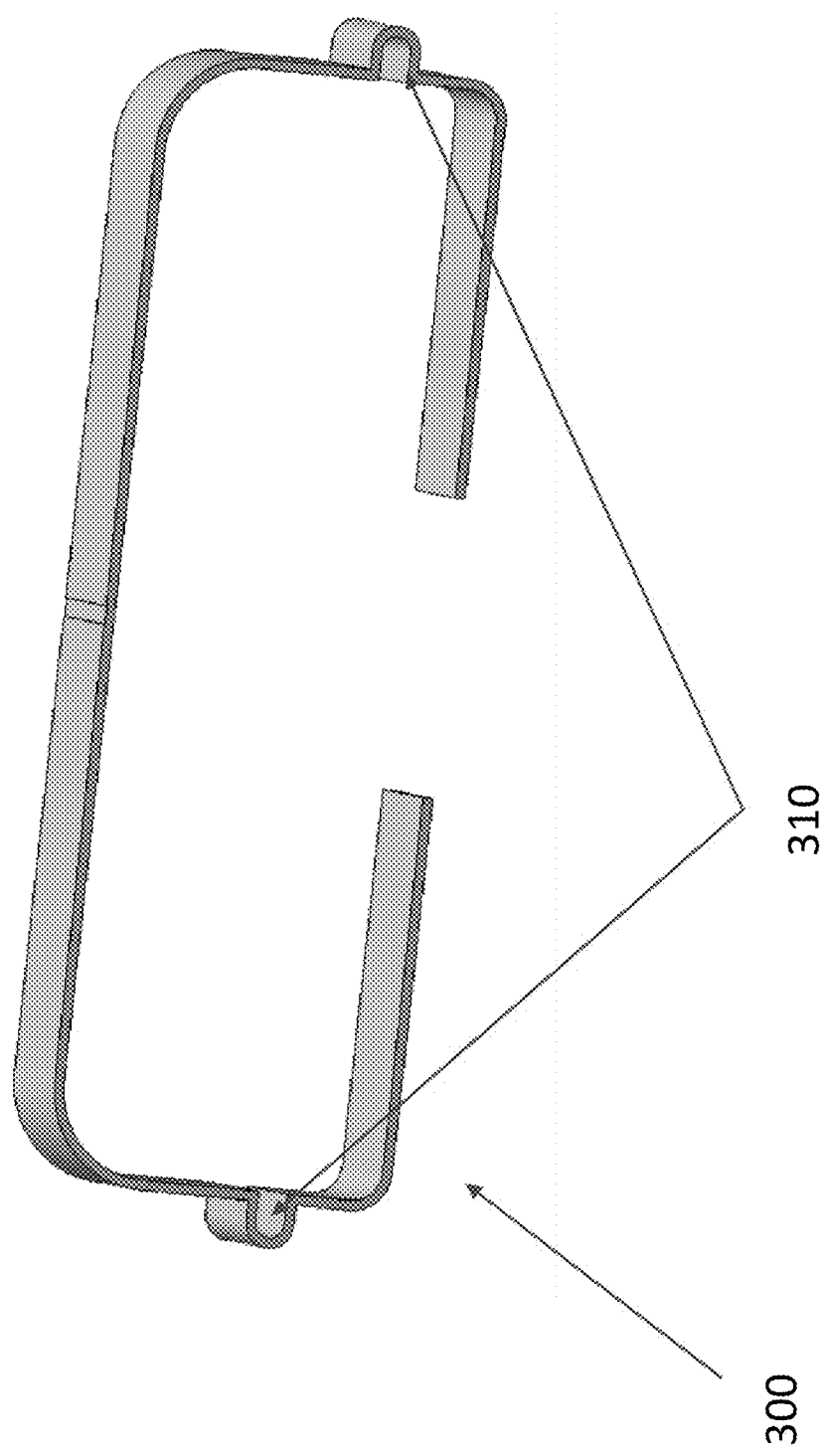
FIG. 10F illustrates an embodiment of a retaining spring clip.

FIG. 10D illustrates the orthopedic treatment device 10 of FIG. 10A implanted on a fractured bone 20 with retaining spring clips 300. FIG. 10E illustrates a schematic exploded perspective view of the orthopedic treatment device 10 with retaining spring clips 300. FIG. 10F illustrates an embodiment of a retaining spring clip 300. The retaining clips 300 can be positioned on the two ends of the body unit 200. The retaining clips 300 can be used to hold together the body unit 200 and retain the body unit 200 in the correct position on the bone plate 100. The retaining clips 300 may secure the body unit 200 to the bone plate 100. The retaining clips 300 can include insertion loops 310. Expansion pliers or a spreader tool can be inserted into the insertion loops 310. The expansion pliers can expand the retaining clip 300 and slide the retaining clip 300 over the end of the bone plate 100. Once spread, the openings of the retaining clips 300 are wider than the bone plate 100. After locating each retaining clip 300 along the body unit 200, the expansion plier is relaxed and the retaining clips 300 are secured between the fractured bone 20 and the bottom edges of the bone plate 100. The expansion pliers can then be removed and the clips 300 will be positioned between the bone plate 100 and the bone 20 and surrounding the body unit 200 as shown in FIGS. 10D and 10E. The body unit 200 may also be attached to the bone plate 100 by clips, fasteners, screws, adhesive or other fastening devices that will stabilize the body unit 200 to the bone plate 100 to create a stable construct. The retaining clips 300 may also be called retention clips or clamps.

Figure 10G:
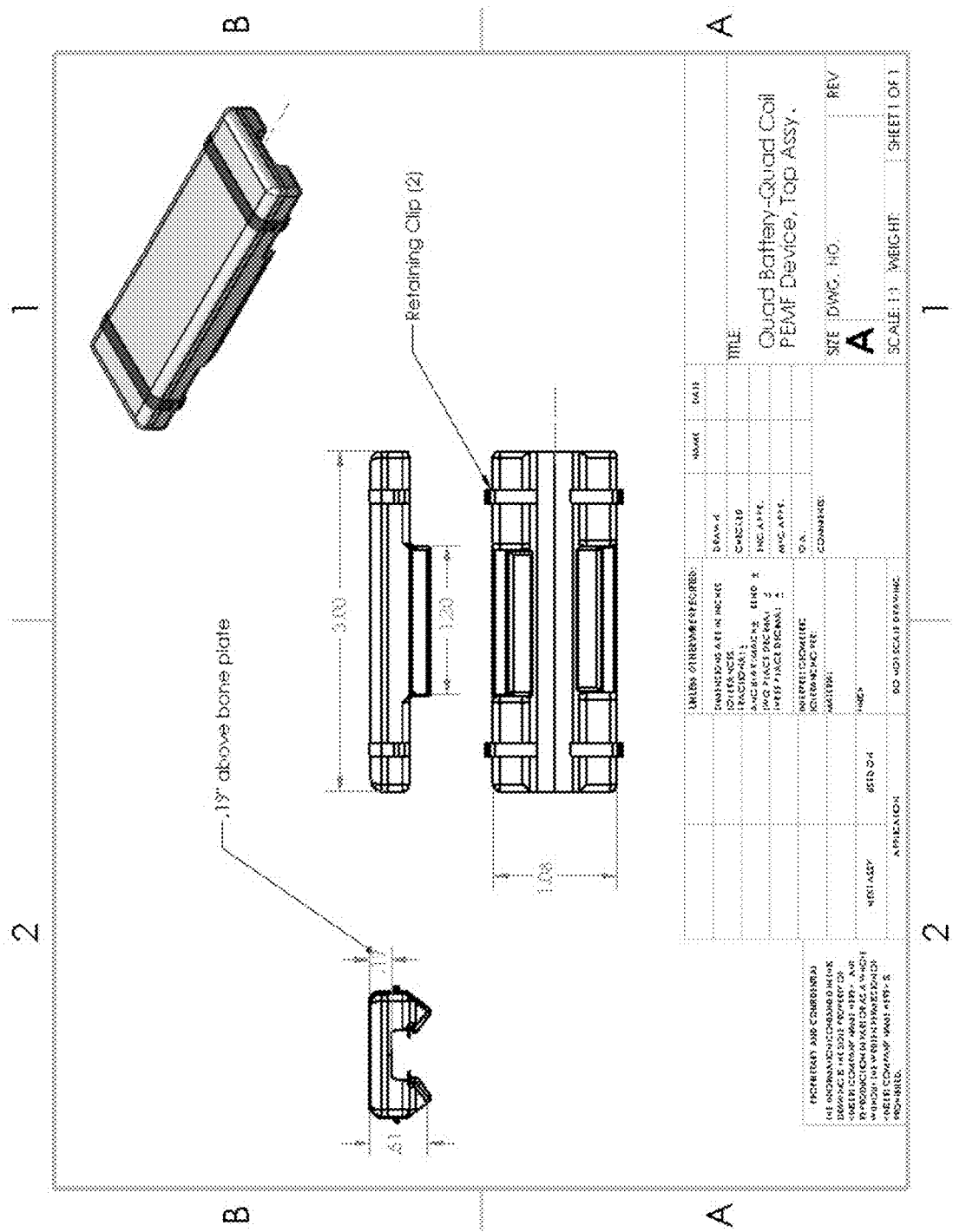
FIG. 10G illustrates an the engineering drawings of the orthopedic treatment device of FIGS. 10A-F.

FIG. 10G illustrates the engineering drawings of the body unit 200 and retaining clips 300. FIG. 10G illustrates an embodiment of the body unit 200 configured for implantation on a fractured bone 20 as shown in FIGS. 10A-F. In some embodiments, the body unit 200 may have a length of approximately 3 inches and a width of approximately 1 inch. In some embodiments, the body unit 200 may have a height ranging approximately 0.2 inches to approximately 0.5 inches. In some embodiments, the body unit 200 may have a height of approximately 0.2 inches above the bone plate 100.

Figure 11A:
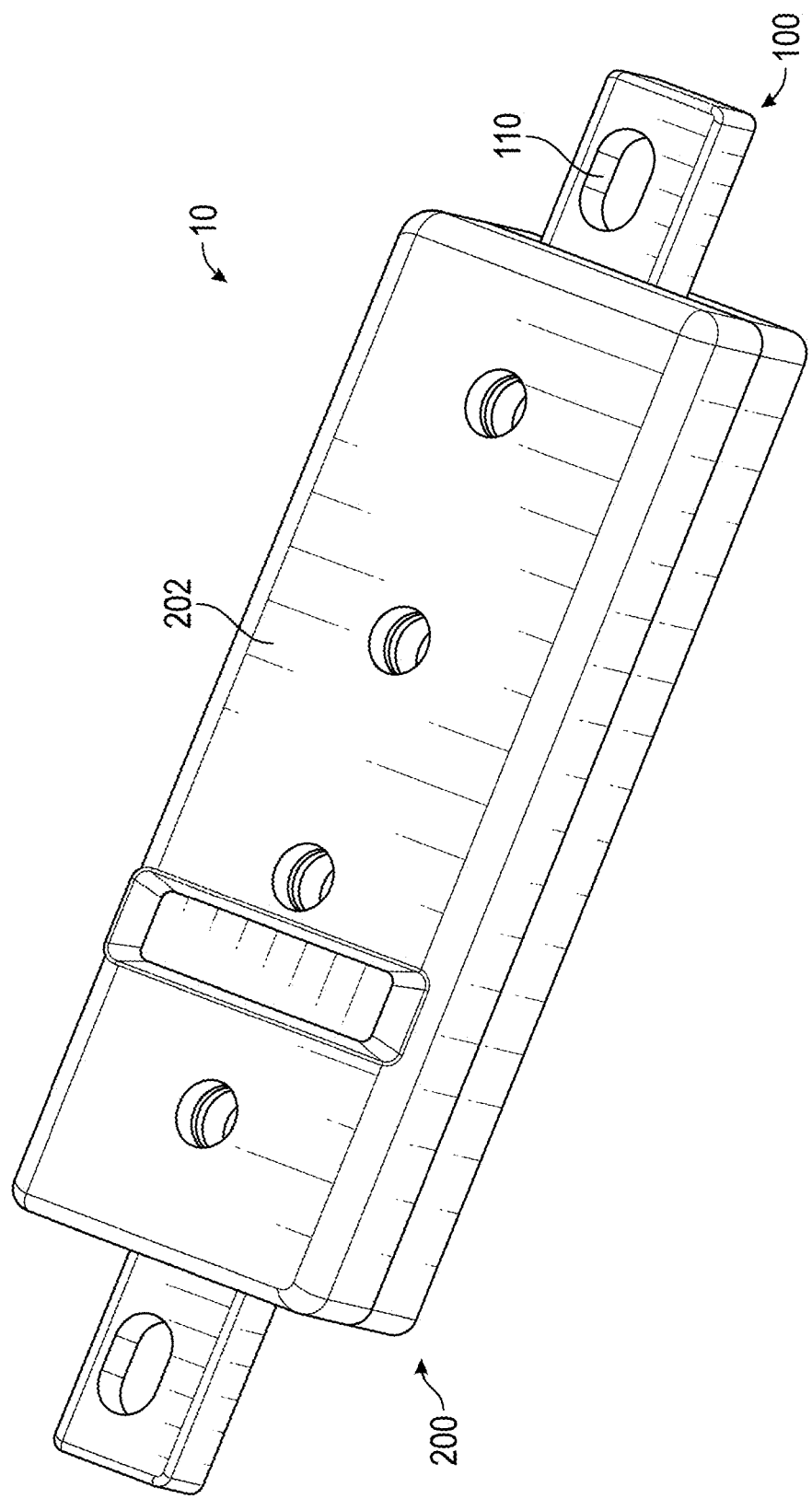
FIG. 11A illustrates another embodiment of an orthopedic treatment device.
Figure 11B:
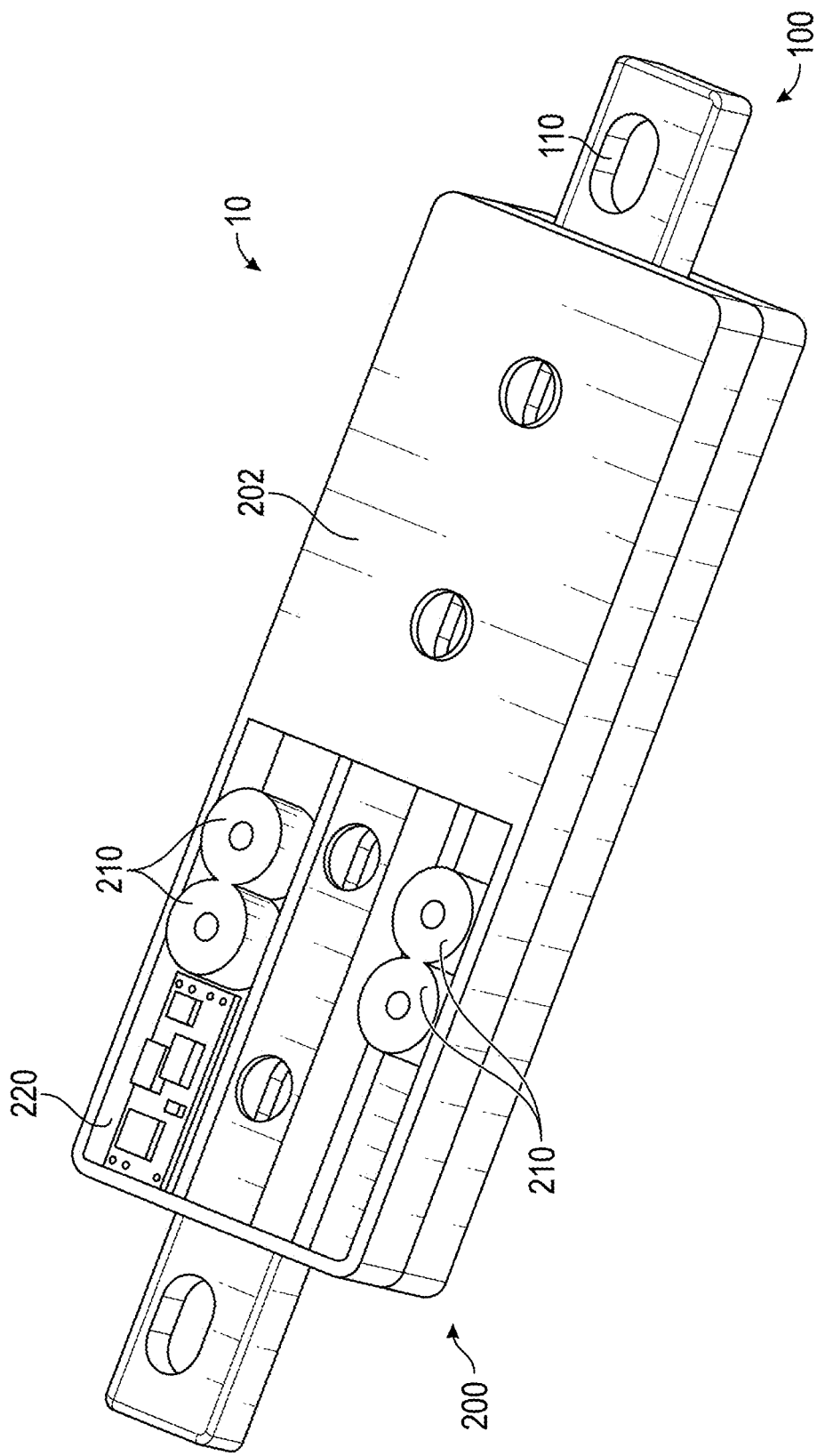
FIG. 11B illustrates an embodiment of the orthopedic treatment device of FIG. 11A with the cover removed on one side.

FIG. 11A illustrates another embodiment of an orthopedic treatment device 10. The orthopedic treatment device 10 may include a bone plate 100 and body unit 200. FIG. 11A illustrates the body unit 200 with the cover 202 enclosing the body unit 200. The components of the body unit 200 can be laser sealed to prevent contact of the components with the patient once the orthopedic treatment device 10 is implanted. FIG. 11B illustrates an embodiment of the orthopedic treatment device 10 of FIG. 11A with the cover 202 removed on one side of the body unit 200 to illustrate the components contained within the body unit 200. The body unit 200 can include electromagnetic field emitters 210 and a controller 220. In this embodiment, the body unit 200 can include four electromagnetic field emitters 210, two per side of the body unit 200.

Figure 11C:
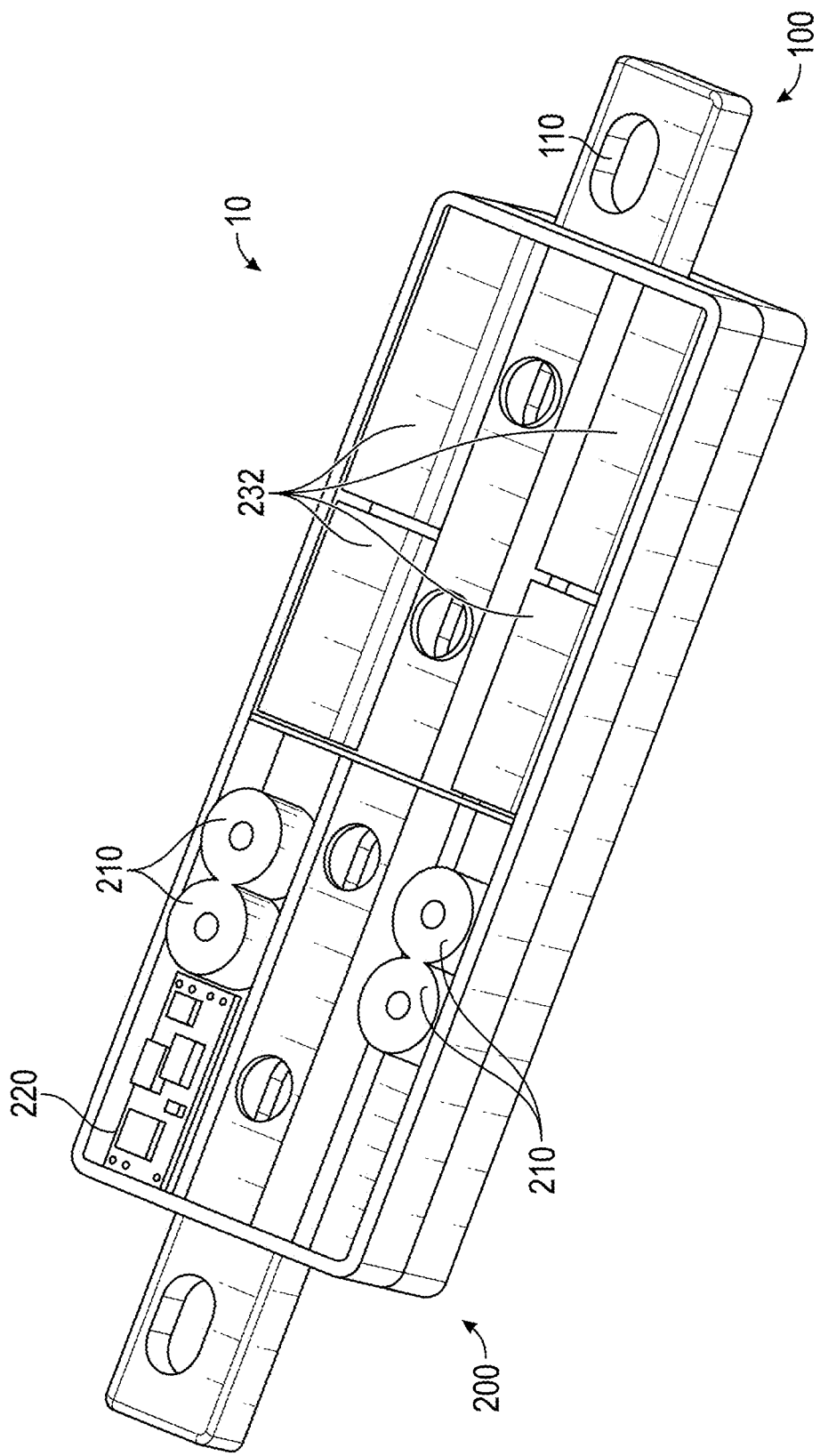
FIG. 11C illustrates an embodiment of the orthopedic treatment device 10 of FIGS. 11A-C with the cover removed on both sides.

FIG. 11C illustrates an embodiment of the orthopedic treatment device 10 of FIGS. 11A-B with the cover 202 removed on both sides of the body unit 200 to illustrate the components contained within the body unit 200. The body unit 200 can include batteries 232, electromagnetic field emitters 210, and a controller 220. In this embodiment, the body unit 200 can include four electromagnetic field emitters 210, two per side of the body unit 200. In this embodiment, the body unit 200 can include four batteries 232, two per side of the body unit 200. The body unit 200 can also include four electromagnetic field emitters 210, two per side. In some embodiments, the batteries 232 may include ENERSYS Product No. QL0020B, 20 mAh implantable lithium-ion batteries. In some embodiments, the electromagnetic field emitters 210 may be round coils or oval coils. In some embodiments, there may be one or two or more electromagnetic field emitters 210 per side of the body unit.

In embodiments, various lithium ion medical cells may be used for powering the device. In some embodiments, a lithium-ion medical cell, Product No. QL0100E2, with a 2.7 V to 4.2 V, and 100 mAh may be used in the body unit 200. In embodiments, such lithium cells may be used in the devices, systems, and methods disclosed herein.

Figure 11D:
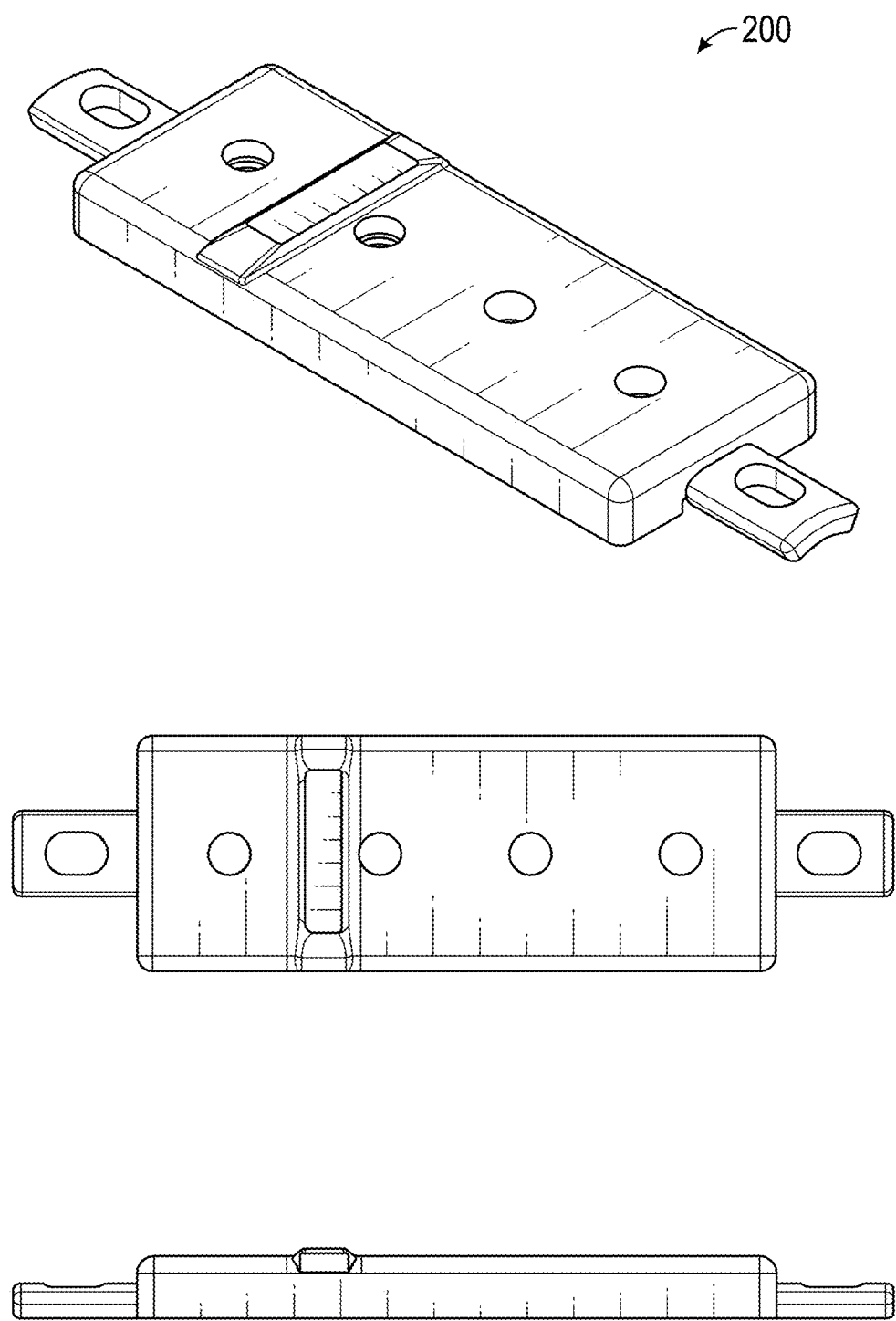
FIG. 11D illustrates an embodiment of the body unit of FIGS. 11A-C.
Figure 11E:
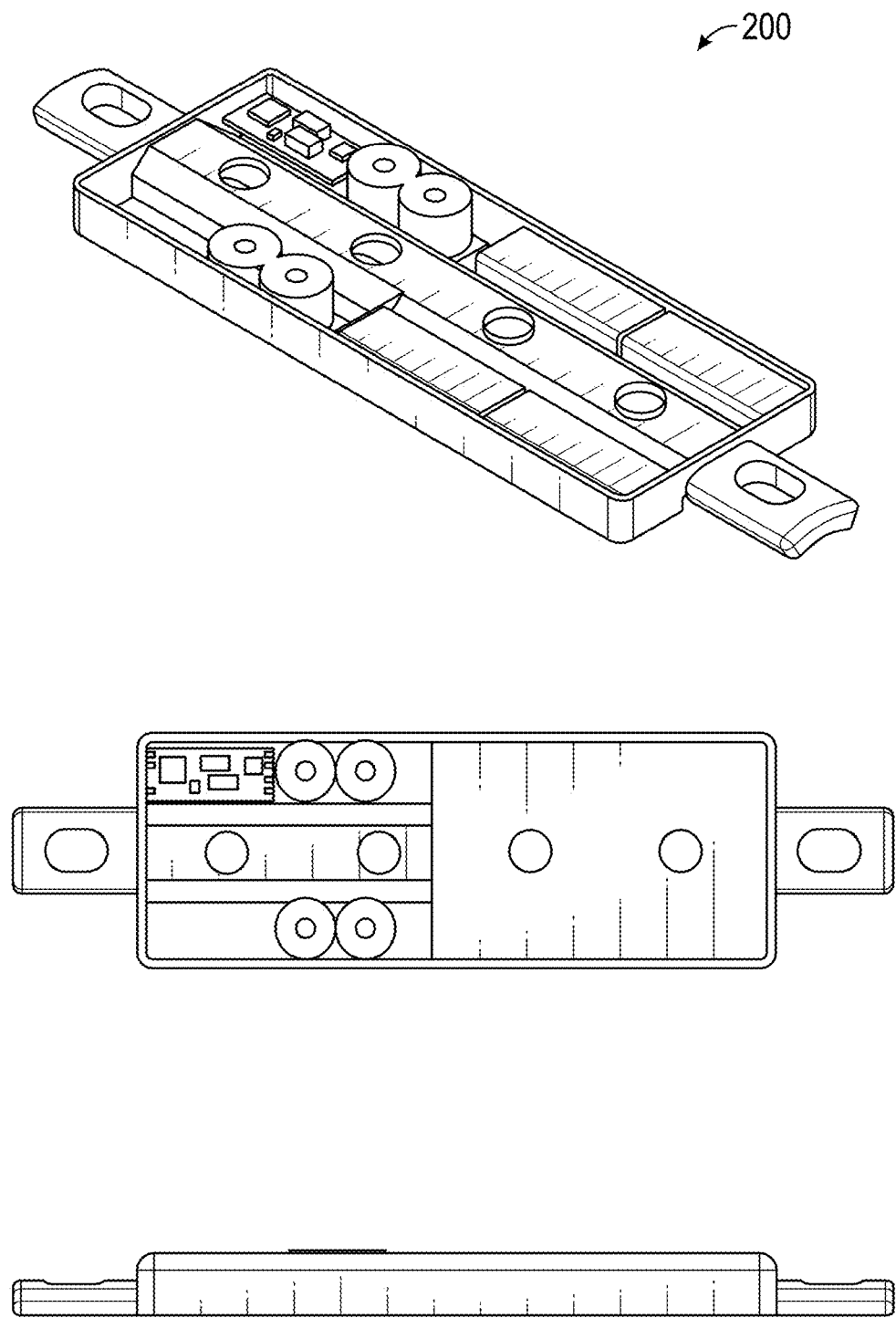
FIG. 11E illustrates an embodiment of the body unit and components contained therein of FIGS. 11A-D.

FIG. 11D illustrates the engineering drawings of an embodiment of a body unit 200. FIG. 11E illustrates an embodiment of the body unit 200 configured for implantation on a fractured bone as shown in FIGS. 11A-C. In some embodiments, the body unit 200 may have a length of approximately 3 inches and a width of approximately 1 inch. In some embodiments, the body unit 200 may have a height ranging approximately 0.2 inches to approximately 0.5 inches. In some embodiments, the body unit 200 may have a height of approximately 0.125 inches above the bone plate 100. In some embodiments, the bone plate 100 may have a diameter of approximately 0.4 inches.

FIG. 11E illustrates the engineering drawings of an embodiment of a body unit 200 with the cover removed to illustrate the components contained therein. FIG. 11E illustrates an embodiment of the body unit 200 and components contained therein configured for implantation on a fractured bone 20 as shown in FIGS. 11A-D.

In some embodiments, the body unit 200 may have a length of approximately 3 inches and a width of approximately 1 inch. In some embodiments, the body unit 200 may have a height ranging approximately 0.2 inches to approximately 0.5 inches. In some embodiments, the body unit 200 may extend past either side of the bone plate 100, ranging approximately 0.1 inches to 0.5 inches. In some embodiments, the diameter of the electromagnetic field emitter 210 may be approximately 0.1 inches to approximately 0.3 inches.

Figure 12A:
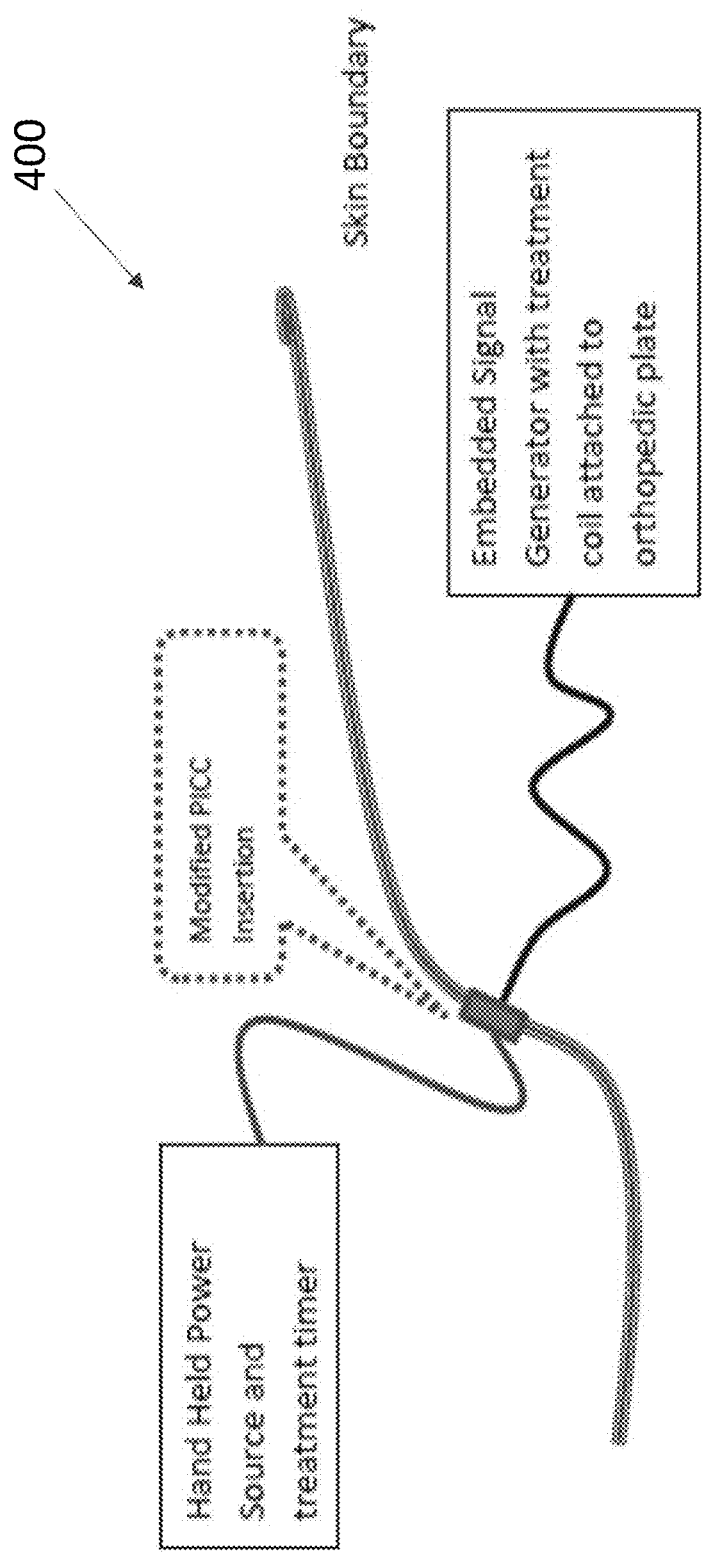
FIG. 12A illustrates an embodiment of a tethered no energy storage system including an external power source, a bone plate, and a peripherally inserted central catheter.

FIGS. 12A-G illustrate an embodiment for a tethered no energy storage system 400. The tethered no energy storage system 400 may include an external power device that may be inserted to and connected using a peripherally inserted central catheter (PICC). FIG. 12A illustrates an embodiment of a tethered no energy storage system 400 including an external power source, a bone plate, and a peripherally inserted central catheter and/or an embedded attached body unit. FIG. 12A illustrates an embodiment of the PICC to connect the external power device to the orthopedic treatment device 100. The external power source may include hand held power source and a treatment timer. The tethered no energy storage solution may also include an embedded signal generator with a treatment coil attached to the orthopedic bone plate 100. The peripherally inserted central catheter (PICC) may include a long insertable tube which may carry a small wire. The PICC may be inserted to deliver the hand held power source and treatment timer through the skin boundary. A tether wire may be inserted into the catheter tubing. The tether wire may plug into the embedded generator after the generator is attached to the fractured bone. The PICC is installed through the skin of the patient at an appropriate location depending on the patient and the location of the fractured bone. In some embodiments, the PICC may include a liquid plug at the end of the PICC line. In some embodiments, the PICC may include an electrical socket which is connected to the embedded generator. The tethered no energy storage solution may include a body unit 200 embedded in a conventional orthopedic bone plate 100 and powering it from an external power source 400. The tethered no energy storage solution may also include a conventional orthopedic bone plate 100 with components for the treatment, powered from the external power source 400. The feeding tube technology breaks through the skin of the patient. Connectors or ports may be embedded into the skin for the PICC tubing. The treatment time may be established by the length of time the embedded generator is powered. The treatment time may be controlled by the treatment timer.

Figure 12B:
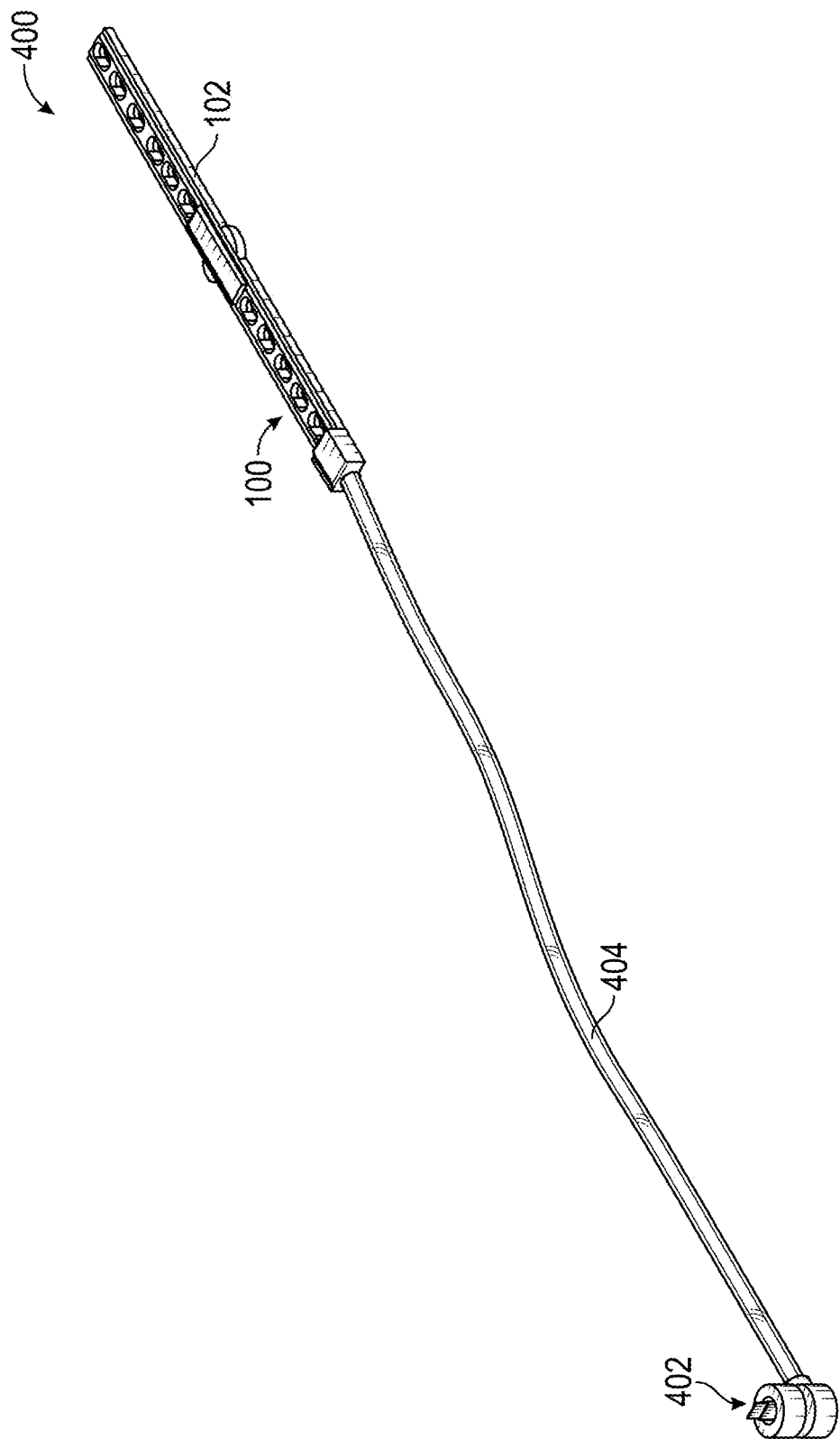
FIG. 12B illustrates an embodiment of the tethered no energy storage system 400 of FIG. 12A including an external power device 400.
Figure 12C:
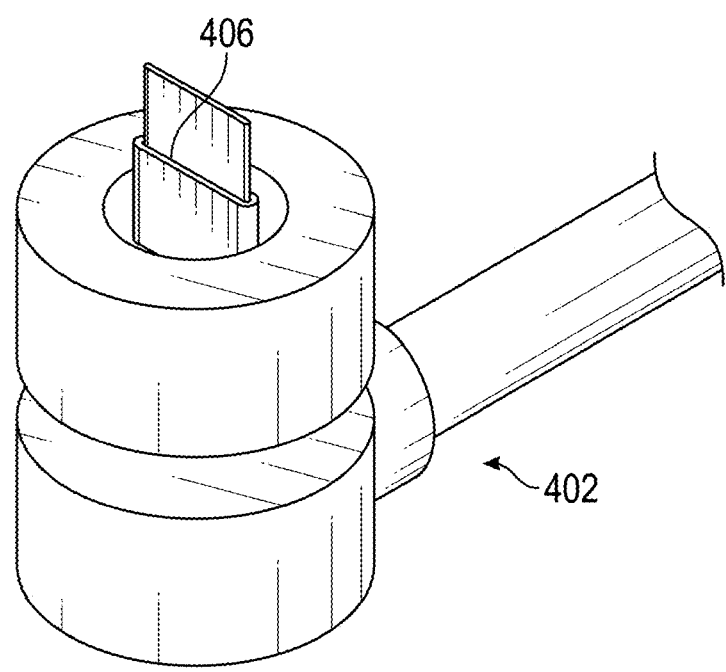
FIG. 12C illustrates an embodiment of a thru skin connector of FIG. 12B.
Figure 12D:
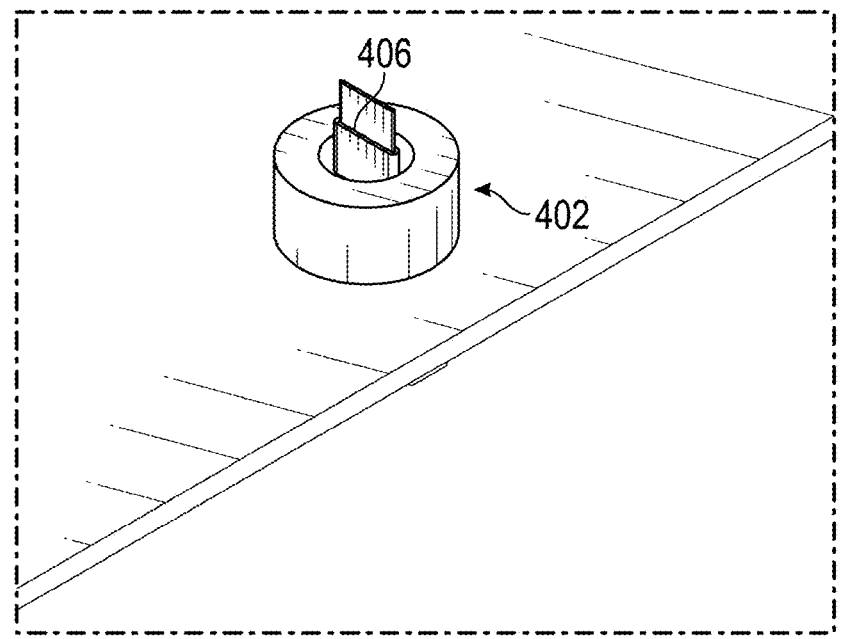
FIG. 12D illustrates an embodiment of a thru skin connector of FIGS. 12B-C mounted in the skin of a patient.
Figure 12E:
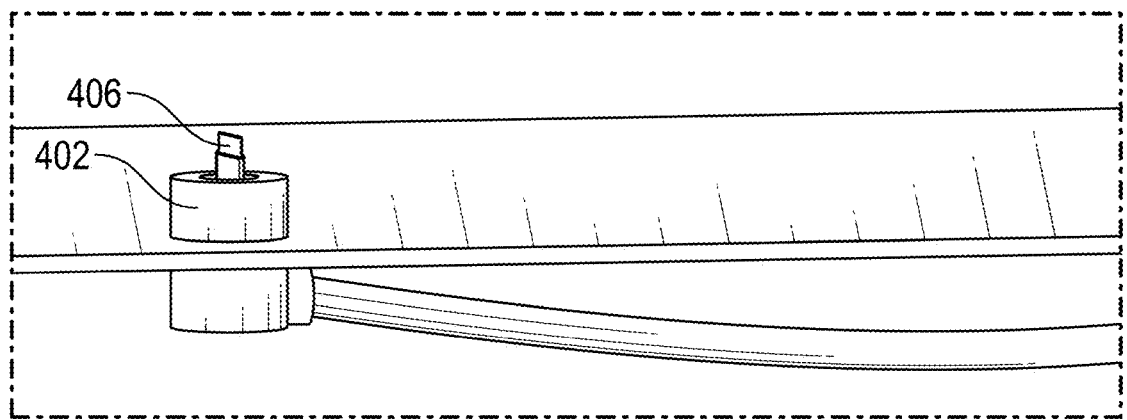
FIG. 12E illustrates a side view of the thru skin connector of FIGS. 12B-D.
Figure 12F:
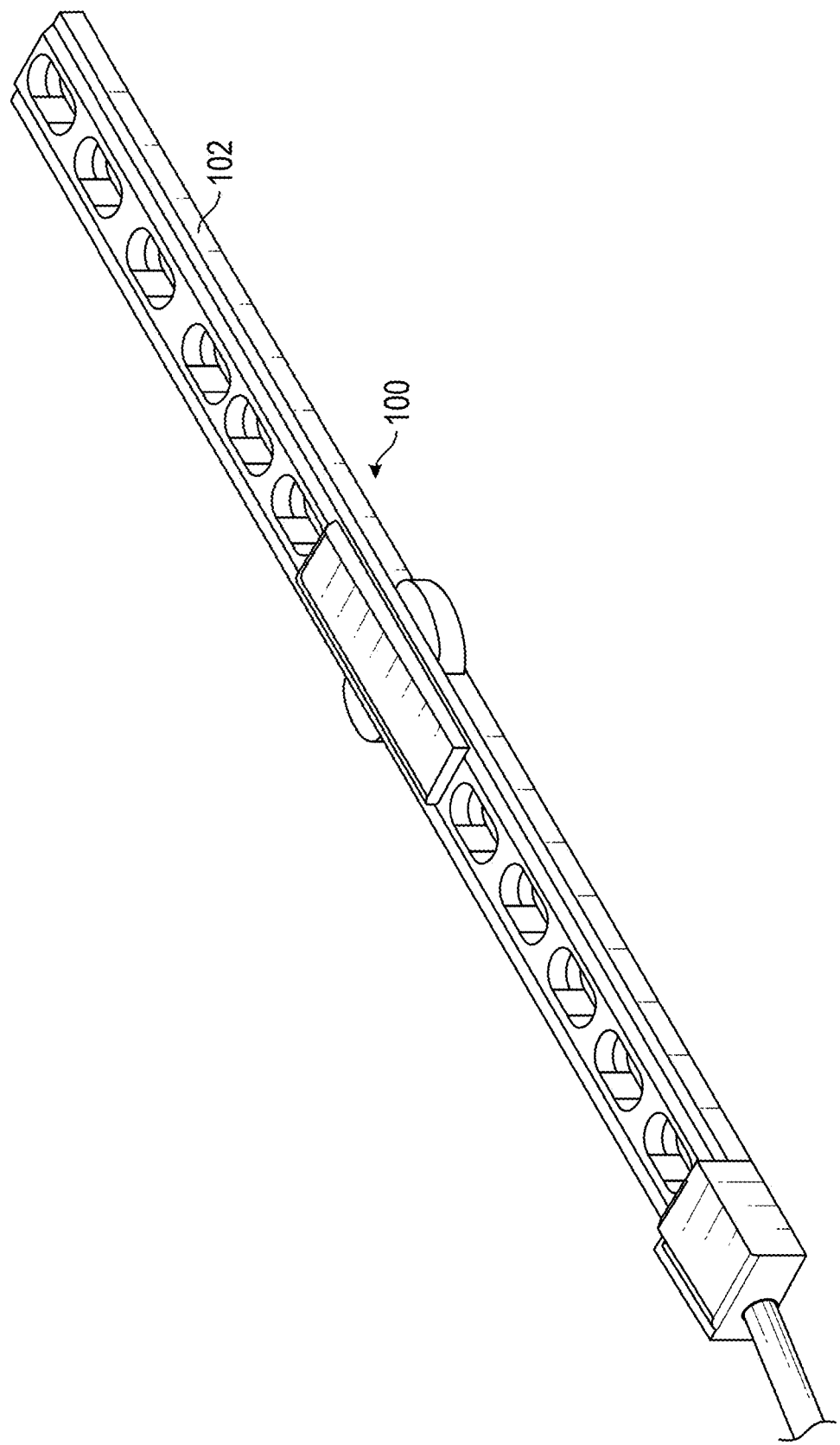
FIG. 12F illustrates an orthopedic bone plate with a cover.
Figure 12G:
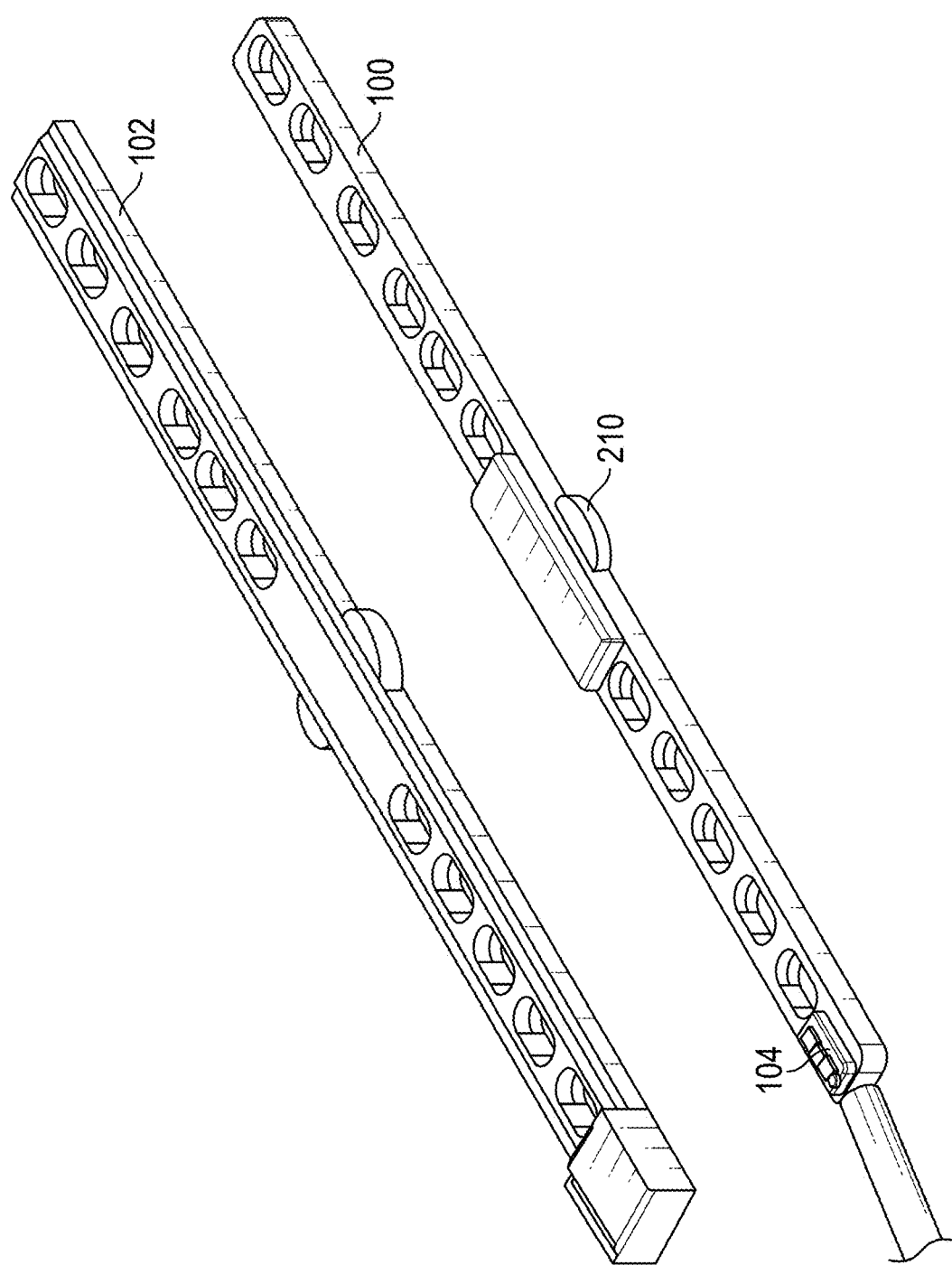
FIG. 12G illustrates the orthopedic bone plate of FIG. 12F with the cover lifted to illustrate the components contained therein.

FIG. 12B illustrates an embodiment of the tethered no energy storage system 400 of FIG. 12A including an external power device 400. The external power device 400 may include a thru skin connector 402 and a bone plate 100. The tethered no energy storage system 400 may include an external power device 400 that may be inserted to and connected using a peripherally inserted central catheter (PICC). The external power device 400 may include a thru skin connector 402 for the wires within PICC tubing 404 as well as an orthopedic bone plate 100 with cover 102. FIG. 12C illustrates an embodiment of a thru skin connector 402 of FIG. 12B. The thru skin connector 402 may include a lightning connector 406 or other appropriate connector. FIG. 12D illustrates an embodiment of a thru skin connector 402 of FIGS. 12B-C that is mounted in the skin of a patient. FIG. 12E illustrates a side view of the thru skin connector 402 of FIGS. 12B-D. FIG. 12F illustrates an orthopedic bone plate 100 with cover 102. The cover 102 may include additional metal to increase the strength and stability of the orthopedic bone plate 100. In certain embodiments a plate may be slid into a body unit like a sleeve, the sleeve comprising any materials or structures described herein. This structure may then be placed or secured to bone. FIG. 12G illustrates the orthopedic bone plate 100 with the cover 102 lifted to illustrate the components of the orthopedic bone plate 100. The components may include a treatment generator 104 and a treatment coil 210. The cover 102 may house the treatment coil 210 and the generator board or treatment generator 104.

Figure 12H:
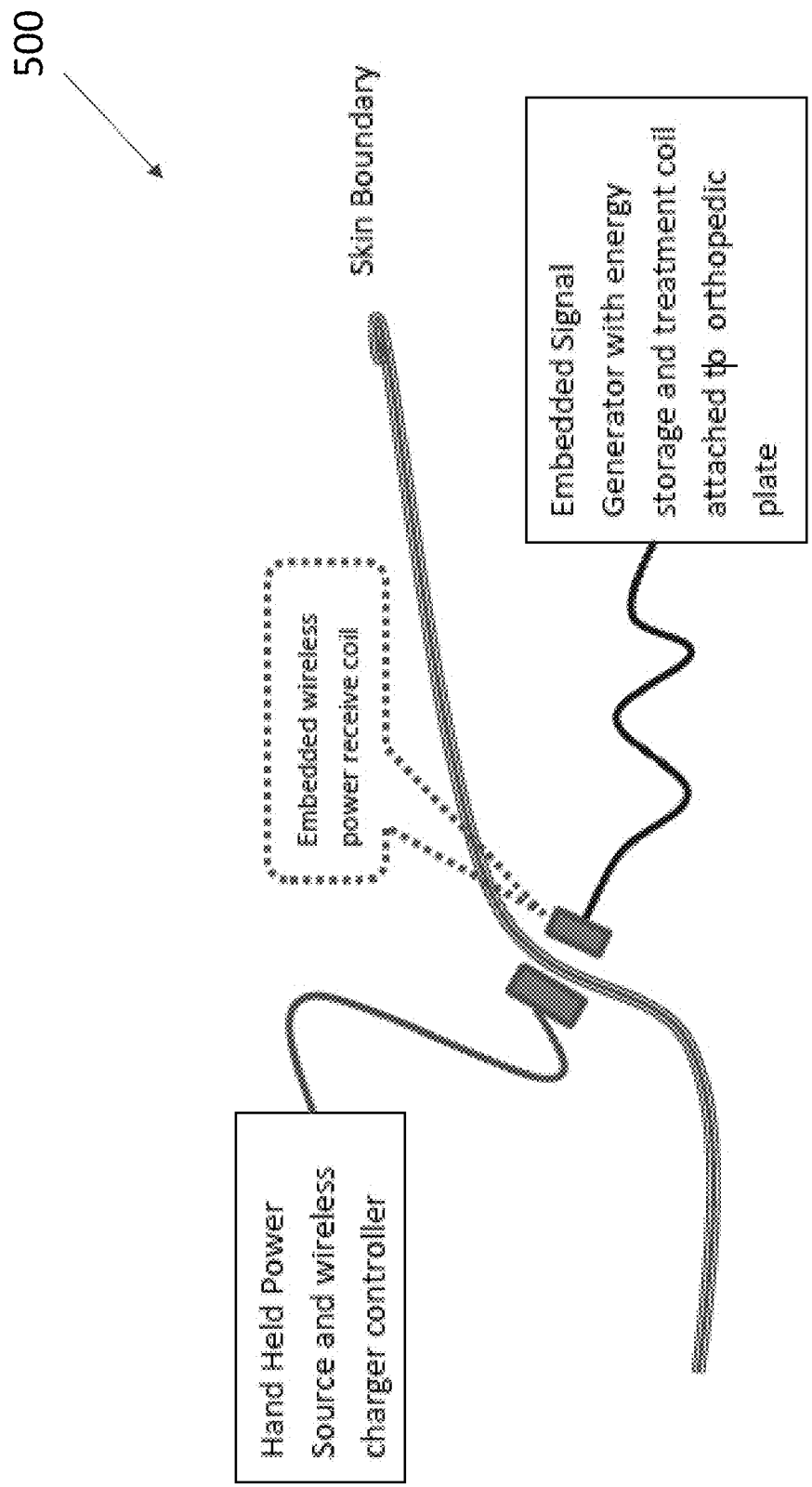
FIG. 12H illustrates an embodiment of the wireless charged with storage system including a wireless charging device, a bone plate, and a peripherally inserted central catheter
Figure 12I:
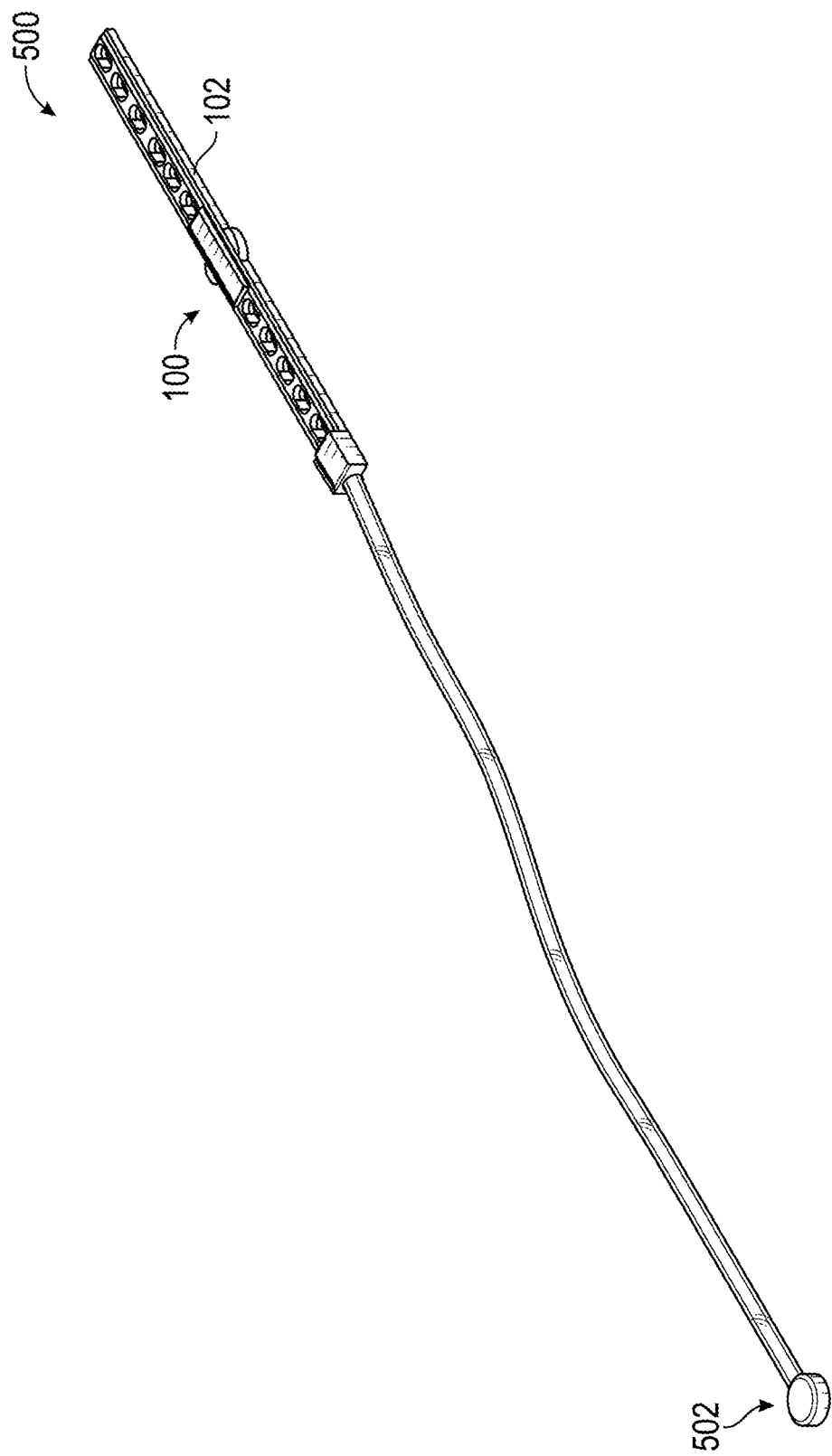
FIG. 12I illustrates an embodiment of the wireless charged with storage system of FIG. 12H including an embedded wireless charging device.
Figure 12J:
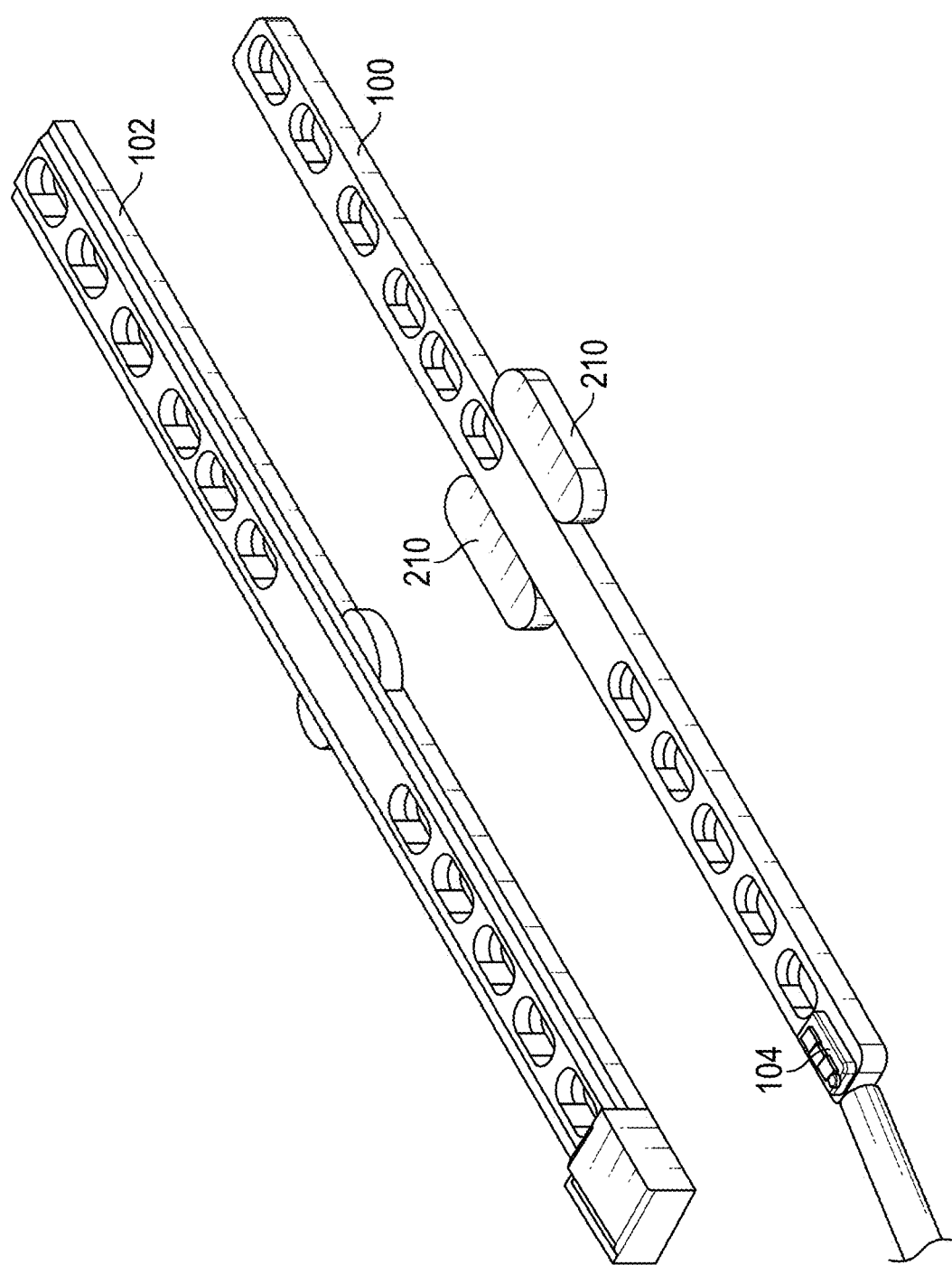
FIG. 12J illustrates the orthopedic bone plate of FIG. 12I with the cover lifted to illustrate the components contained therein.

FIGS. 12H-J illustrate an embodiment for a wirelessly charged storage system 500. The wirelessly charged storage system 500 may include an external power device that may be inserted to and connected using a peripherally inserted central catheter (PICC). The process of insertion and connection may be similar to the tethered no energy storage system 400 of FIGS. 12A-G as described above.

FIG. 12B illustrates an embodiment of the tethered no energy storage system 400 of FIG. 12A including an external power device 400. The external power device 400 may include a thru skin connector 402 and a bone plate 100. The tethered no energy storage system 400 may include an external power device 400 that may be inserted to and connected using a peripherally inserted central catheter (PICC). The external power device 400 may include a thru skin connector 402 for the wires within PICC tubing 404 as well as an orthopedic bone plate 100 with cover 102. FIG. 12C illustrates an embodiment of a thru skin connector 402 of FIG. 12B. The thru skin connector 402 may include a lightning connector 406 or other appropriate connector. FIG. 12D illustrates an embodiment of a thru skin connector 402 of FIGS. 12B-C that is mounted in the skin of a patient. FIG. 12E illustrates a side view of the thru skin connector 402 of FIGS. 12B-D. FIG. 12F illustrates an orthopedic bone plate 100 with cover 102. The cover 102 may include additional metal to increase the strength and stability of the orthopedic bone plate 100. In certain embodiments a plate may be slide into a body unit like a sleeve, the sleeve comprising any materials or structures described herein. This structure may then be placed or secured to bone. FIG. 12G illustrates the orthopedic bone plate 100 with the cover 102 lifted to illustrate the components of the orthopedic bone plate 100. The components may include a treatment generator 104 and a treatment coil 210. The cover 102 may house the treatment coil 210 and the generator board or treatment generator 104.

FIGS. 12H-J illustrate an embodiment for a wirelessly charged storage system 500. The wireless charged with storage system 500 may include an external power device that may be inserted to and connected using a peripherally inserted central catheter (PICC). The process of insertion and connection may be similar to the tethered no energy storage system 400 of FIGS. 12A-G as described above.

FIG. 12I illustrates an embodiment of the wirelessly charged with storage system of FIG. 12H including a wireless charging device, a bone plate 100, and optionally a connector to connect the device to a treatment coil through tissue. The wireless charged with storage system 500 may also include an embedded wireless power receiver coil 502 as well as an embedded signal generator 104 with energy storage and treatment coil 210 attached to the orthopedic bone plate 100.

FIG. 12I illustrates an embodiment of the wireless charged with storage system 500 of FIG. 12H including an embedded wireless charging device 500. The embedded wireless charging device 500 may include a wireless pickup coil 502 and a bone plate 100. The embedded wireless charging device 500 may include a wireless pick up coil 502. The wireless pick up coil 502 may be on a wire which is pre-installed into the embedded generator device. The wireless charging device 500 may be recharged multiple times. In some embodiments, the wireless charging device 500 and the orthopedic plate 100 may be implanted completely under the skin. Therefore the wireless charging device 500 may be connected to and implanted with the bone plate 100 and treatment components which may minimize the stress to the skin and risk of infection to the patient.

FIG. 12J illustrates an embodiment of the orthopedic bone plate 100 with the cover 102 lifted to illustrate the components of the orthopedic bone plate 100. The components may include a treatment generator 104 and dual elongated treatment coils 210. In other embodiments, one or more treatment coils 210 may be included. The multiple treatment coils 210 may be included to disperse the treatment field more efficiently and increase the treatment field strength without modifying the orthopedic bone plate 100.

Figure 13A:
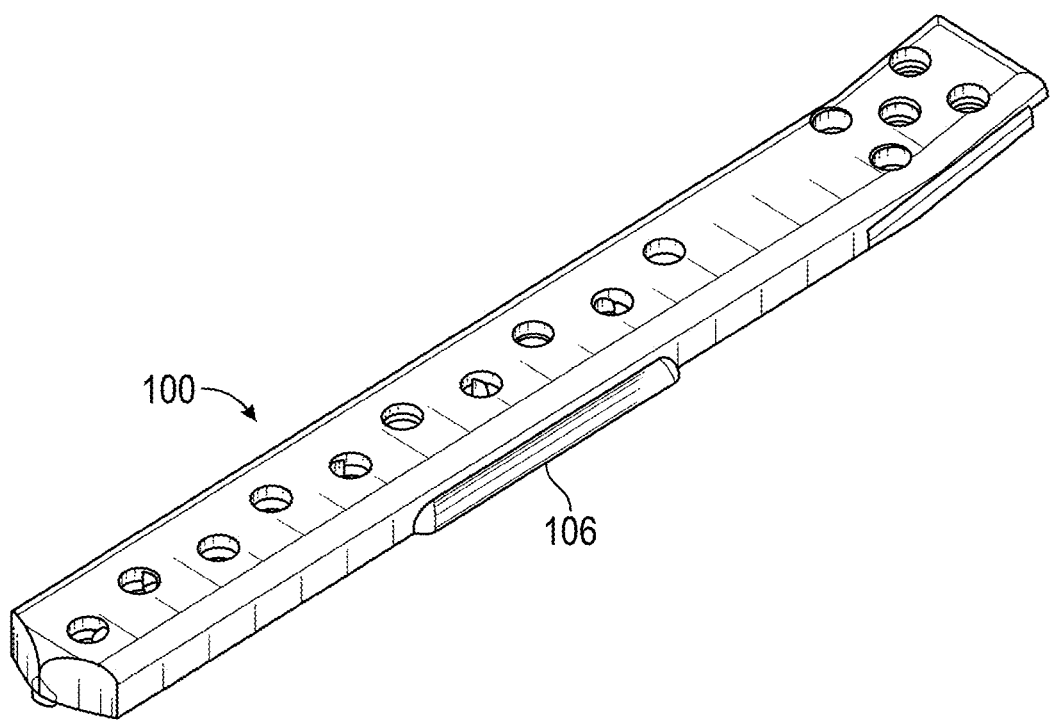
FIG. 13A illustrates another embodiment of a bone plate with a side extension.
Figure 13B:
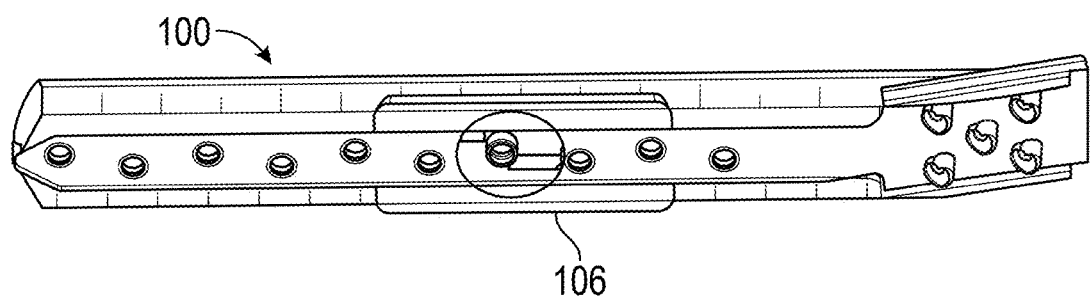
FIG. 13B illustrates a bottom view of the bone plate of FIG. 13A.
Figure 13C:
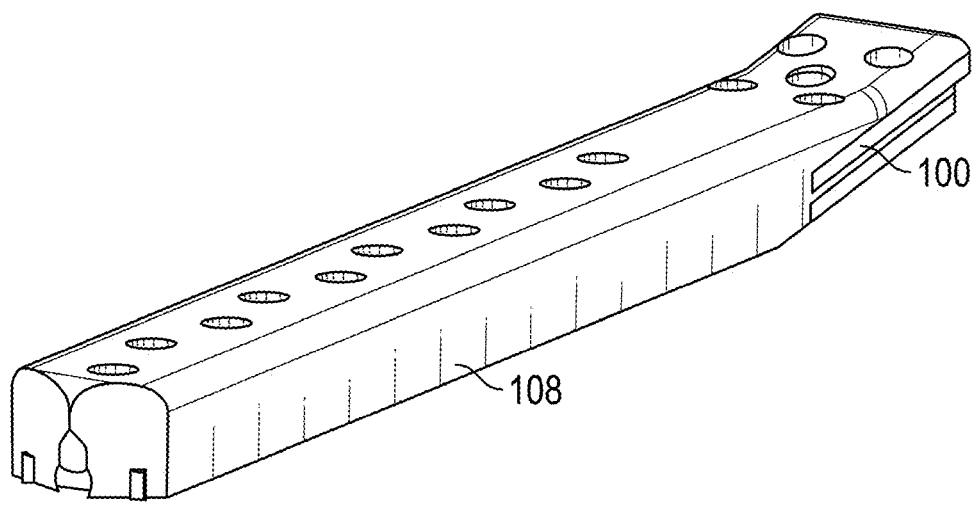
FIG. 13C illustrates the bone plate of FIGS. 13A-B with thicker molding.
Figure 13D:
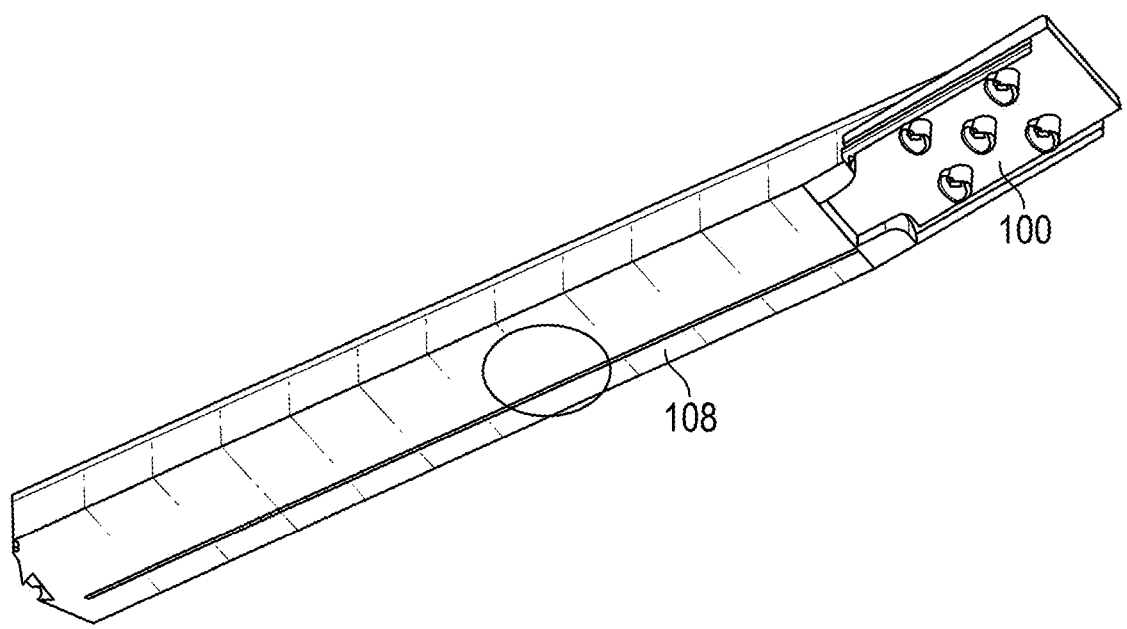
FIG. 13D illustrates the bottom view of the bone plate of FIGS. 13A-C with the thicker molding.

FIG. 13A illustrates another embodiment of an orthopedic treatment device 100 with a side extension 106. The orthopedic treatment device 100 may include a side extension 106 on one side or both sides of the bone plate 100. The side extensions 106 may include one or more treatment coils (not shown). The side extensions 106 may be positioned such that the treatment coils may be positioned as close to the fractured bone (not shown) as possible. FIG. 13B illustrates a bottom view of the bone plate 100 of FIG. 13A. FIG. 13C illustrates the bone plate 100 and body unit 200 of FIGS. 13A-B with thicker molding 108 such that the original bone plate 100 may be inserted into the thicker molding 108 that contains the EMF components. FIG. 13D illustrates the bottom view of the bone plate 100 with the thicker molding 108, illustrating the location of the treatment coil (not shown). In embodiments, the treatment coils may be positioned on the underside of a bone plate, optionally with thicker molding to protect the emitters. In certain embodiments, the body unit may be positioned on top with screw holes aligned with the body unit, such that screws may pass through both components at once.

Figure 14A:
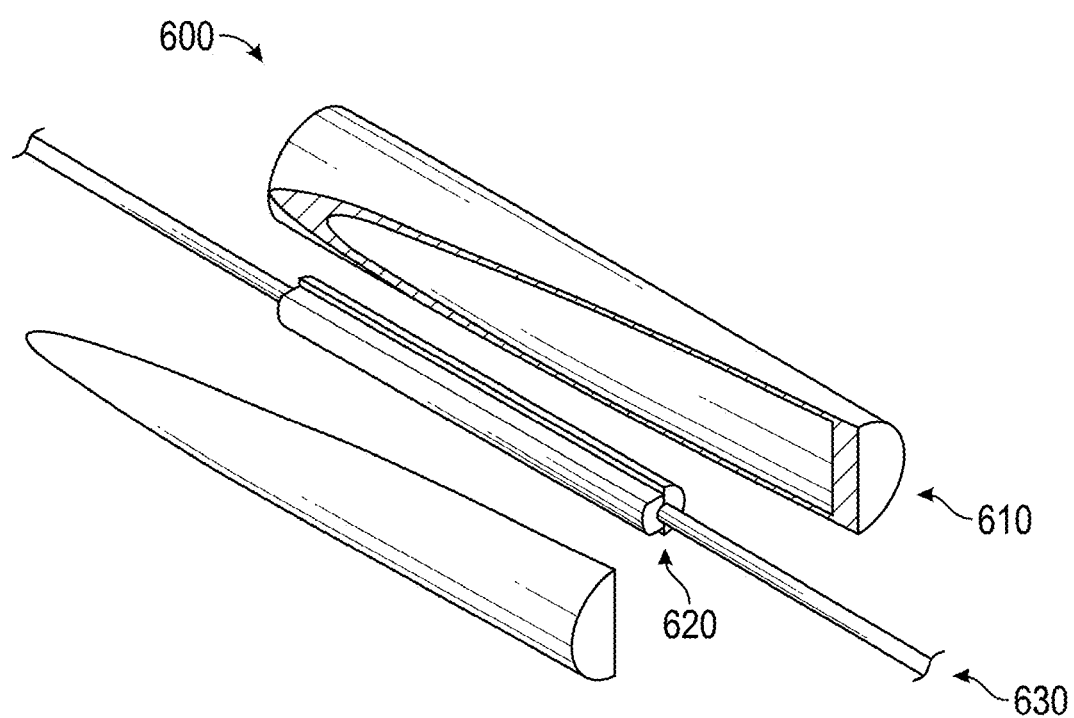
FIG. 14A illustrates an exploded view of an embodiment of a permanent magnet field generator.
Figure 14B:
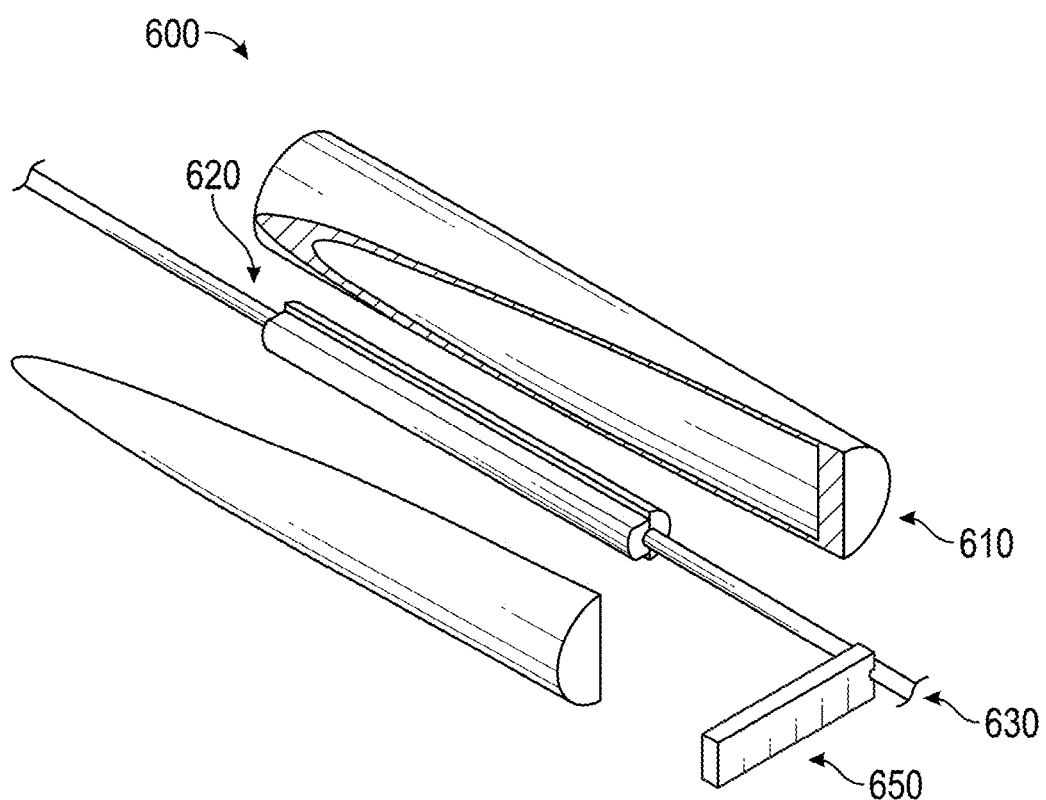
FIG. 14B illustrates an exploded view of the permanent magnet field generator of FIG. 14A with a locking mechanism.

FIGS. 14A-B illustrate an exploded view of an example of a permanent magnet field generator 600, suitable for use with any of the orthopedic treatment devices described herein this section or elsewhere in the specification. The permanent magnet field generator 600 attaches to the implant plate 100 positioned at the fracture of a bone 20 to accelerate fracture healing, similar to the previous embodiments described herein utilizing a coil as an electromagnetic field emitter 200. The permanent magnet field generator 600 may have a permanent magnet 620 emitting a magnetic field strength positioned within a rod 610 such that the permanent magnet field generator 600 could then be rotated or otherwise moved to modulate the field, to apply the desired bioeffect. A permanent magnet 620 of the permanent magnet field generator 600 generates an alternating magnetic field having a known strength and shape by rotation of the permanent magnet 620. By movement of the permanent magnet 620, a fracture in a bone 20 is selectively disposed in and spaced from the alternating field generated. The permanent magnetic field generator 600 may be disposed in the body unit 200. By rotating the permanent magnet 610, the magnet's field is modulated, and the modulation may be optimized for treatment of a broken bone or wound.

In some examples, the permanent magnet 620 may be attached to the rod 610 such that the permanent magnet 620 moves and rotates with the movement of the rod 610. The permanent magnet 620 and the rod 610 may be fixed to each other by nature of the shape of the permanent magnet 620 and corresponding internal shape of the rod 610. For example, the permanent magnet 620 may have a protrusion or may have an edge that is received into a corresponding recess or edge of the internal surface of the rod 610. The permanent magnet 620 may also be fixed or attached to the internal surface of the rod 610 with an appropriate adhesion.

In certain examples, the permanent magnet field generator 600 may have a greater weight on one side along a longitudinal axis 630 of the permanent magnet field generator 600. This weight differential of the permanent magnet field generator 600 may be achieved through a weight differential of the rod 610 or the permanent magnet 620 or both. The rod 610 can have a greater weight on one side along the longitudinal axis 630 of the magnetic field generator 600. The rod 610 may have a greater weight on one side through the use of a different density and/or amount of material on one side. The permanent magnet field generator 600 may also have a non-uniform weight differential along the longitudinal axis 630 of the permanent magnet field generator 600 by the internal permanent magnet 620 having a weight differential. The permanent magnet 610 may have a greater weight on one side of a longitudinal axis 630 through the use of a different density and/or amount of material on one side. The position of the weighted portion of the permanent magnet field generator 600 may determine the motion of the permanent magnet field generator 600. As the patient moves the extremity in which the bone plate 100 and permanent magnet field generator 600 is positioned on, the weighted portion of the rod 610 moves the rod 610 and the permanent magnet 620 positioned within the rod 610 either on a rotational or longitudinal axis 630. Moving the position of the permanent magnet 620 may change the magnetic field generated. The moving permanent magnet field generator 600 will be positioned in close approximation to the fracture to emit the alternating magnetic field towards the fracture to accelerate fracture healing. The use of the permanent magnet field generator 600 passively uses the structure of the permanent magnet 620 and/or the rod 610 and the motion of the patient to generate the magnetic field, without the use of additional electronics or a power source to actuate motion of the permanent magnet field generator 600.

As shown in FIG. 14B, once the fracture is healed and magnetic field stimulation is no longer needed or if it is desirable to stop the magnetic field stimulation, the permanent magnetic field generator 600 can have a locking mechanism 650. An external permanent magnet outside the body (not shown) is used to move the permanent magnetic field generator 600 into a locking mechanism 650 so that the permanent magnet 620 and rod 610 do not move. The permanent magnet field generator 600 can be unlocked at any time by disengaging the permanent magnet 620 and/or rod 610 from the locking mechanism 650 if later magnetic field stimulation is desired.

Figure 15A:
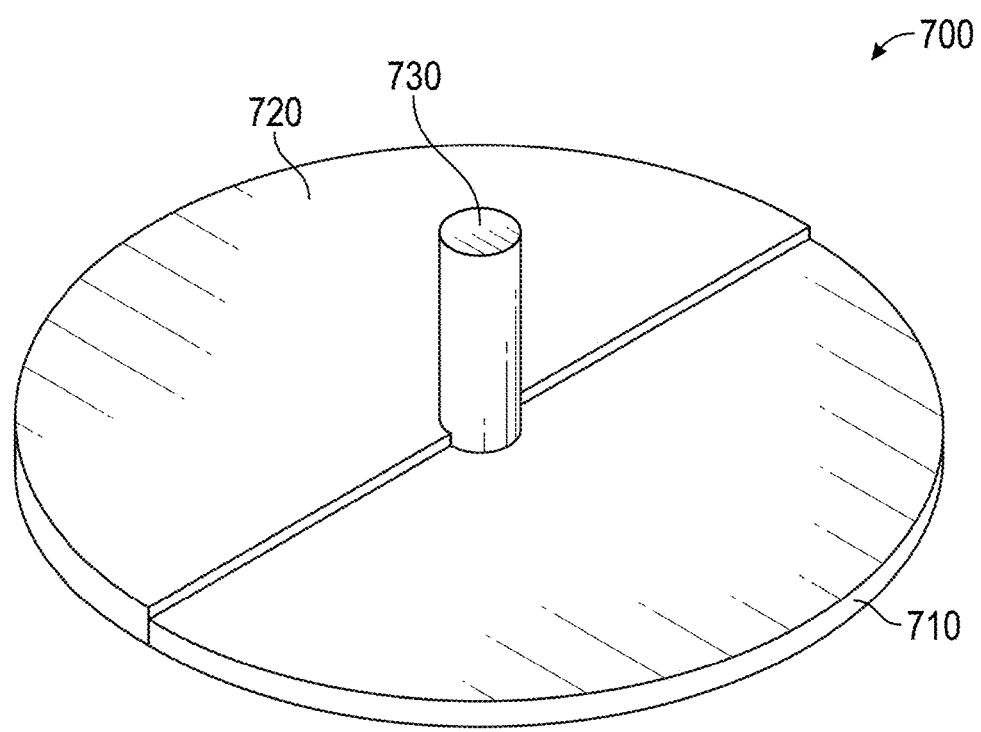
FIG. 15A illustrates another embodiment of a permanent magnet field generator.
Figure 15B:
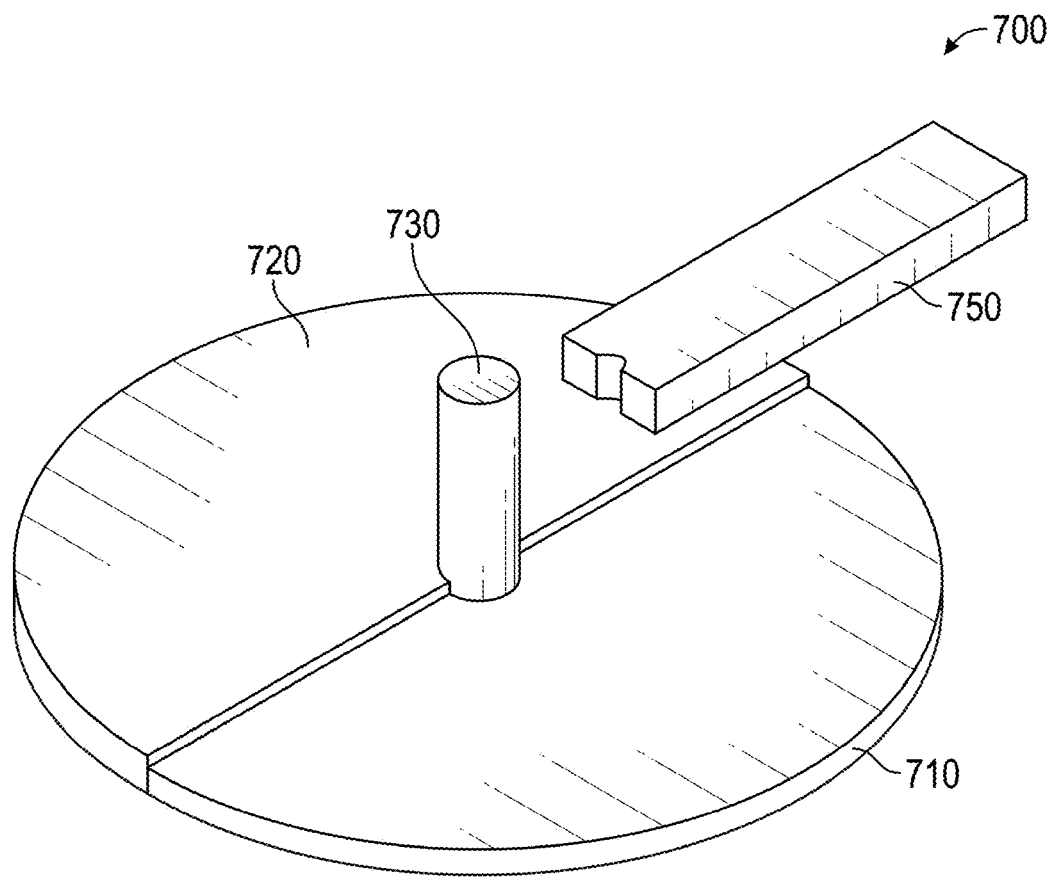
FIG. 15B illustrates the permanent field generator of FIG. 15A with a locking mechanism.

FIGS. 15A-B illustrate an example for a permanent magnet field generator 700. Similar to the permanent magnet generator 600, the permanent magnet field generator 700 attaches to the implant plate 100 positioned at the fracture of a bone 20 to accelerate fracture healing. The permanent magnet field generator 700 has a permanent magnet 720 emitting a magnetic field strength positioned on or within a disc 710. The permanent magnet field generator 700 could then be rotated or otherwise moved to modulate the field, to apply the desired bioeffect. A permanent magnet 720 of the permanent magnet field generator 700 generates an alternating magnetic field having a known strength and shape. By movement of the permanent magnet field generator 700, a fracture in a bone 20 may be selectively disposed in and spaced from the permanent magnet's field. The permanent magnetic field generator 700 may be disposed in the body unit 200. By rotating the permanent magnet 720, the magnet's field is modulated, and the modulation may be optimized for treatment of a broken bone or wound. The permanent magnet field generator 700 may be eccentrically weighted. As the patient moves, the disc 710 and the attached permanent magnet 720 rotate at a frequency determined by the weighted position and by the movement of the patient. As the permanent magnet 720 rotates, the position and polarity of the permanent magnet 720 changes, thereby changing the magnet field. The permanent magnet 720 can be positioned in close proximity to the fracture so that the alternating magnetic field is emitted towards the fracture.

In some examples, the permanent magnet 720 is attached to the disc 710 such that the permanent magnet 720 moves and rotates with the movement of the disc 710. The permanent magnet 720 and the disc 710 are fixed to each other by nature of the shape of the permanent magnet 720 and corresponding internal shape of the disc 710. For example, the permanent magnet 720 may have a protrusion or may have an edge that is received into a corresponding recess or edge of the surface of the disc 710. The permanent magnet 720 may also be fixed or attached to the surface of the disc 710 with an appropriate adhesion.

The permanent magnet field generator 700 can have a greater weight on one side of the permanent magnetic field generator 700. The weight differential allows the permanent field generator 700 to rotate about the rotational axis 730. This weight differential of the permanent magnet field generator 700 may be achieved through a weight differential of the disc 710 or the permanent magnet 720 or both. The permanent magnet field generator 700 may have a greater weight on one side with the permanent magnet 720 positioned on one half of the disc 710. The disc 710 can have a greater weight on one side of the magnetic field generator 700. The disc 710 may have a greater weight on one side through the use of a different density and/or amount of material on one side. The permanent magnet field generator 700 may also have a non-uniform weight differential of the permanent magnet field generator 700 by the permanent magnet 720 having a weight differential. The permanent magnet 710 may have a greater weight on one side through the use of a different density and/or amount of material on one side.

The position of the weighted portion of the permanent magnet field generator 700 may determine the motion of the permanent magnet field generator 700. As the patient moves the extremity in which the bone plate 100 and permanent magnet field generator 700 is positioned on, the weighted portion of the disc 710 moves the disc 710 and the permanent magnet 720 positioned on the disc 710 on a rotational axis 730. Moving the position of the permanent magnet 720 changes the magnetic field generated. The moving permanent magnet field generator 700 may be positioned in close approximation to the fracture to emit the alternating magnetic field towards the fracture to accelerate fracture healing. The use of the permanent magnet field generator 700 may passively use the structure of the permanent magnet 720 and/or the disc 710 and the motion of the patient to generate the magnetic field, without the use of additional electronics or a power source to actuate motion of the permanent magnet field generator 700.

As shown in FIG. 15B, once the fracture is healed and magnetic field stimulation is no longer needed or if it is desirable to stop the magnetic field stimulation, the permanent magnetic field generator 700 may utilize a locking mechanism 750. For example, an external permanent magnet outside the body (not shown) may be used to move the permanent magnetic field generator 700 into a locking mechanism 750 so that the permanent magnet 720 and disc 710 do not move. The permanent magnet field generator 700 can be unlocked at any time by disengaging the permanent magnet 720 and/or disc 710 from the locking mechanism 750 if later magnetic field stimulation is desired In another embodiment of a permanent magnet field generator attached to the bone plate 100, two permanent magnets can be positioned opposite each other in close proximity to the fracture. The opposite poles of the two permanent magnets may be in alignment so the magnetic field moves from the pole of one magnet, transverses the fracture and goes to the opposite pole of the second magnet. The two permanent magnets can be stationary or they can move and change alignment on a weighted rod or disc, creating alternating magnetic fields as the embodiment described previously.

OTHER EMBODIMENTS

In some embodiments, sensors can be incorporated in the internal orthopedic treatment device 10 either on the sides or the undersurface in the protective layer to relay information to the external remote control receiver. The sensors may be linked to a computer, tablet, smart phone or other device for analysis such as information of the internal environment such as temperature, magnetic field strength at the fracture, and the stage or percentage of healing of the fracture from internal sensor device such as a strain gauge.

Embodiments disclosed herein may include Bluetooth communication between the internal orthopedic treatment device 10 and an external remote control receiver. Internal sensors can be incorporated with-in the internal orthopedic treatment device 10 that will send information from the internal environment such as temperature, magnetic field characteristics, and strength at the fracture sight to the external remote control. In addition, a strain gauge can be placed within the orthopedic treatment device 10 that can provide information on the amount of stress on the plate and the fracture. This information can be relayed to the external remote control. The external remote control can provide the information to a computer to calculate the stage of healing of the fracture. The external remote control can send information through Bluetooth or other communication signal to the internal receiver to modify treatment regimen, temperature, and other treatment modalities.

In some embodiments, to assist in providing useful information about the orthopedic treatment device 10 implanted into the body, the orthopedic treatment device 10 may further include sensory coils. Such coils are spaced from the electromagnetic field emitters 210 to receive the generated electromagnetic field at a known distance from the generating coil. The receiver coil is placed at a position, such as a position spaced along the implanted device away from the electromagnetic field emitter 210 or an opposite side of a fracture to be treated, to measure the magnitude and duration of the generated electromagnetic field. Using a transmitter, the results measured by the sensor coil are then forwarded to the remote device, for interpretation by a doctor or technician.

In some embodiments, the internal orthopedic treatment device 10 can communicate with an external electronic device through bluetooth or any other communication vehicle. The external devices can be computers, phone, tablet or other electronic device of the same character that can demonstrate the information relayed from the internal orthopedic treatment device concerning the internal environment of the soft tissues and fracture 20 to the user or surgeon in real time. The information can be analyzed and conclusions can be made by the surgeon or other healthcare professional to make decisions to continue the current treatment regimen and adjust the treatment regimen accordingly. In some embodiments, an application can be downloaded and installed on a phone or tablet to show the relayed internal information in real time on a graph, table or other information display form. The user can have up to date information concerning the internal environment of the patient's body in real time.

The embodiments have been generally described herein as utilizing a coil as an electromagnetic field emitter 210. Other embodiments may include different field generators. In some embodiments, a series of permanent magnets on an actuator can generate an alternating magnetic field. The actuator can be powered by the power source and the characteristics of the treatment regimen such as the rate of the actuator are controlled by the microprocessor controller 220. For example, an alternative embodiment may include a permanent magnet, having a known field strength and shape. The magnet could then be vibrated, rotated or otherwise moved to modulate the field, to apply the desired bioeffect. There, a permanent magnet generates an alternating magnetic field having a known strength and shape. The magnet is disposed on a shaft, rotatable by a rotary actuator, such as a piezoelectric actuator. By rotating the magnet, the magnet's field is modulated, and the modulation may be optimized for treatment of a broken bone or wound. Thus, the actuator/permanent magnet combination forms a controllable magnetic field emitter. The actuator/permanent magnet field emitter may be carried on an orthopedic treatment device 10.

In embodiments, a rotary actuator may be used. In some embodiments, the magnet is provided on a linear actuator, such as a piezoelectric actuator, disposed to move along a direction. By actuating the actuator, a fracture in a bone 20 is selectively disposed in and spaced from the magnet's field. A signal generator may drive the actuator. The magnet and the actuator may be disposed in the body unit 200.

In certain embodiments, the internal orthopedic treatment device 10 can be turned on upon implantation prior to soft tissue closure. In another embodiment, the internal orthopedic treatment device 10 can be turned on remotely by the remote control unit after the soft tissue is closed immediately after surgery or at any time in the healing process remotely, when the surgeon desires to turn on the internal orthopedic treatment device 10 to accelerate healing of the fracture of the bone 20. The internal orthopedic treatment device 10 can be turned off once the fracture of the bone 20 has healed and kept internally for as long as the bone plate 100 and screws 120 are in place. Alternatively, the internal orthopedic treatment device 10 can be removed once the fracture of the bone 20 has healed by a second small outpatient procedure. In some embodiments, only the body unit can be removed at a later date and the bone plate may be maintained to provide structural support. The internal orthopedic treatment device 10 can also be turned on at a later date if necessary if the fracture of the bone 20 is healing in a delayed fashion or is at risk of developing a non-union.

While the internal orthopedic treatment device 10 has been described in connection with several presently preferred embodiments thereof, those skilled in the art will appreciate that many modifications and changes may be made therein without departing from the true spirit and scope of the invention which accordingly is intended to be defined solely by the appended claims.

Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated.

Furthermore, it should be understood when referring to direction of electromagnetic field or signals, it does not necessarily mean that there is no electromagnetic field outside of the axis of transmission. Thus, when direction of the electromagnetic field is discussed with respect to transmitting elements, it may be in relation to where a receiving element may experience highest electromagnetic field.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, terms such as "above," "below," "top," and "bottom" are used throughout the specification. These terms should not be construed as limiting. Rather, these terms are used relative to the orientations of the applicable figures.

In some embodiments, the computing systems described herein may include one or more computing devices, for example, a server, a laptop computer, a mobile device (for example, smart phone, smart watch, tablet, personal digital assistant), a kiosk, automobile console, or a media player, for example. In embodiments, the computing devices may include one or more central processing units (CPUs), which may each include a conventional or proprietary microprocessor. Computing devices may further includes one or more memory, such as random access memory (RAM) for temporary storage of information, one or more read only memory (ROM) for permanent storage of information, and one or more mass storage devices, such as a hard drive, diskette, solid state drive, or optical media storage device. In certain embodiments, the processing device, cloud server, server or gateway device, may be implemented as a computing system. In one embodiment, the modules of the computing systems are connected to the computer using a standard based bus system. In different embodiments, the standard based bus system could be implemented in Peripheral Component Interconnect (PCI), Microchannel, Small Computer computing system Interface (SCSI), Industrial Standard Architecture (ISA) and Extended ISA (EISA) architectures, for example. In addition, the functionality provided for in the components and modules of the computing devices disclosed herein may be combined into fewer components and modules or further separated into additional components and modules.

The computing devices disclosed herein may be controlled and coordinated by operating system software, for example, iOS, Windows XP, Windows Vista, Windows 7, Windows 8, Windows 10, Windows Server, Embedded Windows, Unix, Linux, Ubuntu Linux, SunOS, Solaris, Blackberry OS, Android, raspberry Pi, Arduino, or other operating systems. In Macintosh systems, the operating system may be any available operating system, such as MAC OS X. In other embodiments, the computing device 13000 may be controlled by a proprietary operating system. Conventional operating systems control and schedule computer processes for execution, perform memory management, provide file system, networking, I/O services, and provide a user interface, such as a graphical user interface (GUI), among other things.

The computing devices disclosed herein may include one or more I/O interfaces and devices, for example, a touchpad or touchscreen, but could also include a keyboard, mouse, and printer. In one embodiment, the I/O interfaces and devices 13110 include one or more display devices (such as a touchscreen or monitor) that allow visual presentation of data to a user. More particularly, a display device may provide for the presentation of GUIs, application software data, and multimedia presentations, for example. The computing systems disclosed herein may also include one or more multimedia devices, such as cameras, speakers, video cards, graphics accelerators, and microphones, for example.

In general, the word "module," as used herein, refers to logic embodied in hardware or firmware, or to a collection of software instructions, possibly having entry and exit points, written in a programming language, such as, for example, Python, Java, Lua, C and/or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The block diagrams disclosed herein may be implemented as modules. The modules described herein may be implemented as software modules, but may be represented in hardware or firmware. Generally, the modules described herein refer to logical modules that may be combined with other modules or divided into sub-modules despite their physical organization or storage.

Each of the processes, methods, and algorithms described in the preceding sections may be embodied in, and fully or partially automated by, code modules executed by one or more computer systems or computer processors comprising computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A method of treating an injury comprising:
   positioning an orthopedic treatment device in association with a bone fracture in a mammal,
   the orthopedic treatment device comprising an orthopedic bone plate, a body unit, a first electromagnetic field emitter and a second electromagnetic field emitter,
   the body unit configured to attach to the orthopedic bone plate;
   the first electromagnetic field emitter positioned on a first extension portion extending from the body unit and the second electromagnetic field emitter positioned on a second extension portion extending from the body unit;
   the first and second electromagnetic field emitters positioned adjacent the orthopedic bone plate, the first electromagnetic field emitter positioned on the first extension portion at an angle relative to the orthopedic bone plate toward the bone fracture, the second electromagnetic field emitter positioned on the second extension portion opposite the first electromagnetic field emitter at an angle relative to the orthopedic bone plate toward the bone fracture, the angle comprising less than 180 degrees; projecting at least a portion of the electromagnetic field directly to the bone fracture and not through the orthopedic bone plate;
   the electromagnetic field emitters configured to project opposing electromagnetic fields, the opposing magnetic fields configured to create a Helmholtz effect that increases the magnetic field strength at an orthopedic fracture site;
   and
   activating the electromagnetic field emitters to deliver an electromagnetic field proximate the bone fracture, the electromagnetic field delivered according to a treatment regimen.

2. The method of claim 1, wherein the treatment regimen includes one or more predetermined electromagnetic frequencies and durations.

3. The method of claim 1, further comprising powering the electromagnetic field emitters from a power supply positioned external to the mammal.

4. An orthopedic treatment system, comprising:
   a body unit configured to attach to an orthopedic bone plate;
   a first electromagnetic field emitter positioned on a first extension portion extending from the body unit and a second electromagnetic field emitter positioned on a second extension portion extending from the body unit;
   the first and second electromagnetic field emitters configured to project an electromagnetic field at a therapeutic frequency for a therapeutic duration;
   the first and second electromagnetic field emitters positioned adjacent the orthopedic bone plate, the first electromagnetic field emitter positioned on the first extension portion at an angle relative to the orthopedic bone plate toward the bone fracture, the second electromagnetic field emitter positioned on the second extension portion opposite the first electromagnetic field emitter at an angle relative to the orthopedic bone plate toward the bone fracture, the angle comprising less than 180 degrees;
   wherein the electromagnetic field emitters are configured to project at least a portion of the electromagnetic field directly to the bone fracture and not through the orthopedic bone plate;
   the electromagnetic field emitters configured to project opposing electromagnetic fields, the opposing magnetic fields configured to create a Helmholtz effect that increases the magnetic field strength at an orthopedic fracture site;
   an internal power source positioned within the body unit, the internal power source configured to provide electrical current to the electromagnetic field emitters; and
   a receiving coil positioned within the body unit, the receiving coil configured to receive power from an external power source, the external power source positioned outside the body unit.

5. The orthopedic treatment system of claim 4, wherein the external power source comprises a delivery coil, the delivery coil configured to inductively charge the receiving coil.

6. The orthopedic treatment system of claim 5, wherein the receiving coil is configured to provide electrical current to the internal power source.

7. The orthopedic treatment system of claim 4, further comprising a microprocessor contained within the body unit, the microprocessor in electrical communication with the electromagnetic field emitters, the internal power source, and the receiving coil.

8. The orthopedic treatment system of claim 7, wherein the microprocessor is configured to modify an electrical current delivered from the receiving coil to the internal power source such that the electrical current is in a usable form for the internal power source.

9. The orthopedic treatment system of claim 4, wherein the electromagnetic field emitters comprise a coil wrapped around a ferrite core.

10. The orthopedic treatment system of claim 4, further comprising an antenna positioned within the body unit, the antenna configured to communicate with an external remote control receiver.

11. The orthopedic treatment system of claim 10, further comprising a sensor positioned within the body unit in communication with the antenna, the sensor configured to measure an internal characteristic within an implant site.

12. The orthopedic treatment system of claim 11, wherein the sensor is configured to measure a stress exerted on the orthopedic bone plate.

13. The orthopedic treatment system of claim 4, wherein the external power source is configured to be positioned on the skin of a mammal, the mammal implanted with the orthopedic bone plate.

14. The orthopedic treatment system of claim 4, wherein the microprocessor is configured to direct the electromagnetic field emitters to deliver a therapy regimen.

* * * * *